United States Patent [19]
Gentles et al.

[11] Patent Number: 6,008,398
[45] Date of Patent: Dec. 28, 1999

[54] NON-NUCLEOTIDE PHOSPHORUS ESTER OLIGOMERS

[75] Inventors: Robert Gerard Gentles, Lake Bluff, Ill.; Alan F. Cook, Cedar Grove, N.J.; Morris Jonathan Rudolph, Boonton, N.J.; Reza Fathi, Newark, N.J.

[73] Assignee: Genzyme Corporation, Framingham, Mass.

[21] Appl. No.: 08/595,264

[22] Filed: Feb. 1, 1996

Related U.S. Application Data

[63] Continuation-in-part of application No. 08/374,040, Jan. 18, 1995.

[51] Int. Cl.$^6$ .............................. C07F 9/141; C07F 9/143; C07F 9/145; C07F 9/40
[52] U.S. Cl. ......................... 558/157; 558/156; 558/158; 558/159; 558/160; 558/161; 558/162; 558/163; 558/164; 558/165
[58] Field of Search ................................. 558/157, 158, 558/159, 160, 167, 169, 156

[56] References Cited

FOREIGN PATENT DOCUMENTS

WO 92/02532  2/1992  WIPO .

*Primary Examiner*—Johann Richter
*Assistant Examiner*—Jane C. Oswecki
*Attorney, Agent, or Firm*—Elliot M. Olstein

[57] ABSTRACT

A phosphorus ester oligomer having the structure:

$$B_1-R_1-\left[O-\underset{A}{\overset{\overset{O}{\|}}{P}}-OR_1\right]_n-B_2$$

wherein A can be the same or different in each monomeric unit and each is independently selected from the group consisting of oxygen, sulfur, lower alkyl, substituted or unsubstituted alkylamino, substituted or unsubstituted arylamino and aminoalkyl; $B_1$ and $B_2$ can be the same or different and each is independently selected from hydrogen, lower alkyl, a labeling group, a protecting group, a phosphoramidate or a phosphomonoester; $R_1$ can be the same or different in each monomeric unit, and in at least one of the non-nucleotide monomeric units, $R_1$ is independently selected from the group consisting of (i) a non-vicinal diol attached to a hydrogen bond donor functionality; (ii) a hydrogen bond acceptor selected from an ether; (iii) a non-vicinal diol attached to a hydrophobic functionality or a vicinal diol attached to an aliphatic or alicyclic hydrophobic functionality (iv) a diol attached to a ring substituted anionic functionality and (v) a cationic moiety attached to a non-vicinal or alicyclic diol, any of which can further include a detectable label, and n is at least two. Preferred $R_1$ moieties include condensation products of alicyclic diols and polycyclic diols; also the non-nucleotide monomers thereof, and the use of the oligomers as selective target-binding compounds.

34 Claims, 6 Drawing Sheets a: M = 5'-THYMIDYL
b: M = LIBRARY

NON-NUCLEOTIDE PHOSPHORUS ESTER OLIGOMERS

This application is a continuation-in-part of U.S. Ser. No. 08/374,040, filed on Jan. 18, 1995.

This invention relates to the field of oligomeric molecules ("oligomers") containing non-nucleotide phosphorus esters, which are useful as mixtures, particularly in the form of combinatorial libraries, to screen for binding activity to biologically significant targets, including protein targets. Esters with high affinity have value as drug or diagnostic candidates, and such combinatorial libraries thereof have value as products used to identify such candidates.

A variety of phosphorus ester oligomers have been reported in the literature. Non-nucleotide phosphorus esters have been incorporated into oligonucleotides as linker groups which connect two separate oligonucleotide sequences. For example, oligonucleotides containing a single non-nucleotide hexaethylene glycol phosphodiester have been described (Durand et al., 1990). The oligonucleotide regions of the molecule were base paired to form a duplex structure, and the non-nucleotide phosphorus ester functioned as a loop to connect the two strands. An aromatic non-nucleotide phosphodiester has also been incorporated into an oligonucleotide as a linker group (Salunkhe et al., 1992), and the non-nucleosides 1,2 dideoxyribose and 1-phenyl-1,2-dideoxyribose have been incorporated into oligonucleotides for enzymatic studies.

Molecules containing multiple non-nucleotide phosphorus esters have also been reported. For example, several 1,3-propanediol phosphodiester groups have been incorporated into oligonucleotides (Richardson and Schepartz, 1991) to act as tethers of varying lengths which connect two separate oligonucleotide sequences. The tethers enabled the oligonucleotide sequences to bind to non-contiguous regions of an RNA target. Diethylene-glycol phosphodiester and decaethylene-glycol phosphodiester moieties have also been incorporated into oligonucleotides for similar purposes (Cload and Schepartz, 1991).

Non-nucleotide phosphorus ester oligomers have been used for other functions. For example, oligomeric phosphorus esters possessing substituted alkyl substituents have been synthesized and used as fire retardants (Hardy and Jaffe 1980). Oligomeric phosphorus esters of phenolic compounds have also been described as fireproofing agents (Sase et al., 1988).

In relation to drug discovery, non-nucleotide compounds have been used in combination with nucleotides in a combinatorial manner to search for compounds which bind to biological targets. Compounds possessing various backbone elements such as ethylene glycol phosphate, hydroxyproline phosphate, or PNA ("peptide nucleic acid") have been used, and a twelve residue pentamer combinatorial library containing substituted ethylene glycol phosphate residues in combination with nucleotide residues was reported (Ecker, 1994). Other groups have described the assembly of combinatorial libraries of oligomers made from a set of monomers consisting of a side chain and a uniform backbone element (Zuckermann et al., 1994). The application of combinatorial libraries to drug discovery has recently been extensively reviewed (Gallop et al., 1994, Gordon et al., 1994).

The desirability of introducing conformational constraint into potential drug candidates is a well understood principle in medicinal chemistry. The concept of designing combinatorial libraries of constrained molecules has recently been described, wherein rigid small molecules act as a frame onto which various pendant functions can be attached. Alternatively, the flexibility of members of an oligomer library can be limited by the use of intrinsically constrained amide linking groups, as in the case of PNA or N-substituted glycine libraries (Zuckerman et al., 1994). In the area of antisense oligonucleotides, the phosphodiester linkages have been substituted with acetal groups (Matteucci et al., 1993), and the regular deoxyribose element of the backbone has been replaced with a 5-3-ethano-bridged rigid analog, both with the objective of introducing conformational constraint. In the latter case, the oligonucleotides bound with higher affinity to their cognate sequences than did conventional oligonucleotides (Leumann et al., 1993).

A rapidly growing new industry has developed around the preparation and use of combinatorial libraries of a wide variety of compounds, including polypeptides, small molecules and oligonucleotides. Companies in this industry sell such combinatorial libraries to pharmaceutical, diagnostic and other markets as research reagents suitable for screening and also provide services for companies which do not have the facilities for in house screening of such libraries. The market demand for these combinatorial libraries has been an encouraging demonstration that their utility is well recognized by those skilled in the art.

Combinatorial libraries of oligomers having potential for binding to proteins and other biological targets are valuable products for use in drug screening and other research by pharmaceutical and diagnostic industry members and by investigators in the biological and medical arts. They provide a convenient and rich source of candidates for modulating biologically active agents, particularly proteins, through their binding potential. Thus these products constitute a pool of readily accessible and sophisticated oligomeric constructs and libraries that satisfies this market and thereby makes structures available to research programs which would not otherwise have access to the broad spectrum of candidates they provide.

One aspect of the invention provides a phosphorus ester oligomer of monomeric units, which oligomer has the structure:

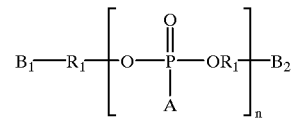

wherein
A can be the same or different in each monomeric unit and each is independently selected from the group consisting of oxygen, sulfur, lower alkyl, substituted or unsubstituted alkylamino, substituted or unsubstituted arylamino and aminoalkyl;

$B_1$ and $B_2$ can be the same or different and each is independently selected from hydrogen, lower alkyl, a labeling group, a protecting group, a phosphoramidate or a phosphomonoester;

$R_1$ can be the same or different in each monomeric unit, and in at least one of the non-nucleotide monomeric units, $R_1$ is independently selected from the group consisting of a condensation product of (i) a non-vicinal diol attached to a hydrogen bond donor functionality; (ii) a hydrogen bond acceptor selected from an ether, a purine- or pyrimidine-substituted 1,2-diol or a disubstituted heterocycle; (iii) a non-vicinal diol attached to a hydrophobic functionality or a vicinal diol attached to an aliphatic or alicyclic hydrophobic functionality (iv) a diol attached to a ring substituted-anionic functionality and (v) a cationic moiety attached to a non-vicinal or alicyclic diol, any of which can further include a detectable label; and n is at least one.

Preferred embodiments of the above aspect include the following. Preferably n=2–20, and more preferably 1–6. Preferably the hydrogen bond donor contains a hydroxyl, amide, imide or thiol group or is a basic compound. The basic compound can contain an amine moiety or a substituted or unsubstituted thiazole. Preferred hydrogen bond acceptors include an amine or ether moiety. Examples include the 5-substituted 2-hydroxymethyl-3-hydroxy-tetrahydrofurans and bis(hydroxyalkyl)-substituted heterocycles or substituted or unsubstituted theophyllines. Preferred hydrophobic functionalities are selected from aromatic rings, alkanes, cycloalkanes and aromatic rings fused to alkanes. Particularly preferred hydrophobic functionalities include those wherein $R_1$ is selected from a substituted alkane, a 3,3-disubstituted 3-amino-1,2-propanediol, a substituted or unsubstituted alicyclic ring wherein the ring size is from 4–12, a 3-substituted indole, a substituted or unsubstituted hydroxyalkyl phenol and an alicyclic dicarboxylic acid. Preferred anionic functionalities include those wherein the anionic functionality is a mono- or dicarboxylic acid moiety. More particularly preferred moieties include tricyclononene dicarboxylic acids and cyclopentane acetic acids. Preferred cationic functionalities include bis(hydroxyalkyl)-substituted nitrogen-containing heterocycles. More particularly preferred cationic functionalities include substituted alkanes and 3,3-disubstituted 3-amino-1,2-propanediols. Another preferred embodiment of the above aspect is an oligomer wherein in at least one of the monomeric units $R_1$ is a heterocyclic, an alicyclic or a polycyclic ring system, preferably containing an indole, thiazole, imidazole, pyridine, purine or pyrimidine ring. The alicyclic ring system preferably contains a cyclopentane or cyclooctane ring, and can be substituted with at least one carboxylic acid moiety. The polycyclic ring system preferably contains a bicyclic or tricyclic ring or is a polycyclic arene. The bicyclic ring system is preferably a bicyclic alkane, such as tricyclononene. The polycyclic arene is preferably diphenyl bicyclooctane.

Another aspect of the invention provides a phosphorus ester oligomer of monomeric units, which oligomer has the structure:

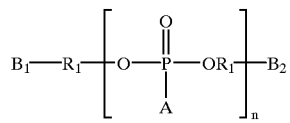

wherein

A can be the same or different in each monomeric unit and each is independently selected from the group consisting of oxygen, sulfur, lower alkyl, substituted or unsubstituted alkylamino, substituted or unsubstituted arylamino and aminoalkyl;

$B_1$ and $B_2$ can be the same or different and each is independently selected from hydrogen, lower alkyl, a labeling group, a protecting group, a phosphoramidate or a phosphomonoester;

$R_1$ can be the same or different in each monomeric unit and in at least one of the monomeric units is independently selected from the group consisting of (i) an aliphatic acyclic hydrocarbon diol wherein the diol groups are non-vicinal or are substituted;

(ii) a purine- or pyrimidine-substituted variant of the diols of (i) or of aliphatic acyclic hydrocarbon vicinal diols;

(iii) an acyclic aliphatic diol having an amino group with at least one hydrogen substitution moiety;

(iv) an alicyclic or polycyclic diol, optionally substituted with a carboxy or carboxyalkyl substituent;

(v) a hydroxy or hydroxyalkyl substituted tetrahydrofuran;

(vi) an indole-substituted acyclic aliphatic diol;

(vii) an aromatic ring or ring system having two substitutions independently selected from the group consisting of hydroxy or hydroxyalkyl;

(viii) a heterocyclic compound having two substitutions independently selected from the group consisting of hydroxy or hydroxyalkyl; and (ix) a dihydroxyalkyl thiazole or dihydroxyalkyl oxazoline, any of which can further include a detectable label; and n is at least 1, preferably 2–20, and more preferably 2–6.

Another aspect of the invention provides a non-nucleotide monomeric unit having the structure:

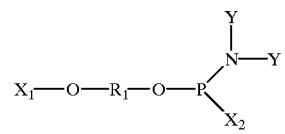

wherein $X_1$ is a protecting group;

$X_2$ is a branched or unbranched lower alkyl group or a substituted or unsubstituted alkoxy group;

Y is a branched or unbranched lower alkyl group; and $R_1$ is independently selected from the group consisting of a condensation product of (i) a non-vicinal diol attached to a hydrogen bond donor functionality; (ii) a hydrogen bond acceptor selected from an ether, a purine- or pyrimidine-substituted 1,2-diol or a disubstituted heterocycle; (iii) a non-vicinal diol attached to a hydrophobic functionality or a vicinal diol attached to an aliphatic or alicyclic hydrophobic functionality (iv) a diol attached to a ring substituted anionic functionality and (v) a cationic moiety attached to a non-vicinal or alicyclic diol, any of which can further include a detectable label.

Another aspect of the invention provides a non-nucleotide monomeric unit having the structure:

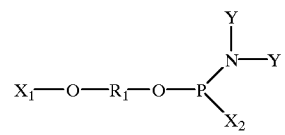

wherein $X_1$ is a protecting group;

$X_2$ is a branched or unbranched lower alkyl group or a substituted or unsubstituted alkoxy group;

Y is a branched or unbranched lower alkyl group; and $R_1$ is a condensation product of:

(i) an aliphatic acyclic diol wherein the diol hydroxyl groups are non-vicinal or are substituted;

(ii) a purine- or pyrimidine-substituted variants of the diols of (i) or of aliphatic acyclic hydrocarbon vicinal diols;
(iii) an acyclic aliphatic diol having an amino group with at least one hydrogen substitution moiety;
(iv) an alicyclic or polycyclic diol, optionally substituted with a carboxy or carboxyalkyl substituent;
(v) a hydroxy or hydroxyalkyl substituted tetrahydrofuran;
(vi) an indole substituted acyclic aliphatic diol;
(vii) an aromatic ring or ring system having two substitutions independently selected from the group consisting of hydroxy or hydroxyalkyl;
(viii) a heterocyclic compound having two substitutions independently selected from the group consisting of hydroxy or hydroxyalkyl; and
(ix) a dihydroxyalkyl thiazole or dihydroxyalkyl oxazoline, any of which can further include a detectable label.

Another aspect of the invention provides a non-nucleotide monomeric unit having the structure:

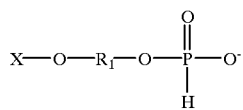

wherein
X is a protecting group;
$R_1$ is independently selected from the group consisting of a condensation product of (i) a non-vicinal diol attached to a hydrogen bond donor functionality; (ii) a hydrogen bond acceptor selected from an ether, a purine- or pyrimidine-substituted 1,2-diol or a disubstituted heterocycle; (iii) a non-vicinal diol attached to a hydrophobic functionality or a vicinal diol attached to an aliphatic or alicyclic hydrophobic functionality (iv) a diol attached to a ring-substituted anionic functionality and (v) a cationic moiety attached to a non-vicinal or alicyclic diol, any of which can further include a detectable label.

Another aspect of the invention provides a non-nucleotide monomeric unit having the structure:

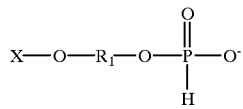

wherein
X is a protecting group;
$R_1$ is a condensation product of:
(i) an aliphatic acyclic hydrocarbon diol wherein the diol hydroxyl groups are non-vicinal or are substituted;
(ii) a purine- or pyrimidine-substituted variant of the diols of (i) or of aliphatic acyclic vicinal diols;
(iii) an acyclic aliphatic diol having an amino group with at least one hydrogen substitution moiety;
(iv) an alicyclic or polycyclic diol, optionally substituted with a carboxy or carboxyalkyl substituent;
(v) a hydroxy- or hydroxyalkyl-substituted tetrahydrofuran;
(vi) an indole-substituted acyclic aliphatic diol;
(vii) an aromatic ring or ring system having two substitutions independently selected from the group consisting of hydroxy or hydroxyalkyl;
(viii) a heterocyclic compound having two substitutions independently selected from the group consisting of hydroxy or hydroxyalkyl; and
(ix) a dihydroxyalkyl thiazole or dihydroxyalkyl oxazoline, any of which can further include a detectable label.

Another aspect of the invention provides a phosphorus ester oligomer of monomeric units, which oligomer has the structure:

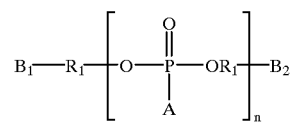

wherein
A can be the same or different in each monomeric unit and each is independently selected from the group consisting of oxygen, sulfur, lower alkyl, substituted or unsubstituted alkylamino, substituted or unsubstituted arylamino and aminoalkyl;
$B_1$ and $B_2$ can be the same or different and each is independently selected from hydrogen, lower alkyl, a labeling group, a protecting group, a phosphoramidate or a phosphomonoester;
$R_1$ can be the same or different in each monomeric unit, and is selected from the group of a nucleoside moiety and, in at least one monomeric unit, $R_1$ is independently selected from the group consisting of a condensation product of (i) a non-vicinal diol attached to a hydrogen bond donor functionality; (ii) a hydrogen bond acceptor selected from an ether, a purine or pyrimidine substituted 1,2-diol or a disubstituted heterocycle; (iii) a non-vicinal diol attached to a hydrophobic functionality or a vicinal diol attached to an aliphatic or alicyclic hydrophobic functionality (iv) a diol attached to a ring substituted anionic functionality and (v) a cationic moiety attached to a non-vicinal or alicyclic diol, any of which can further include a detectable label; and
n is at least one.

Another aspect of the invention provides a combinatorial mixture of the above oligomers. Preferred embodiments of combinatorial mixtures of oligomers include those wherein A is 1–20, and particularly preferred embodiments include those wherein A is 1–6. Preferred embodiments include combinatorial mixtures wherein the oligomers are labeled with $_{32}$phosphorus, $^{35}$sulfur, tritium, fluorescein or biotin.

A large, highly diverse set of structurally unrelated, derivatized monomers is prepared for incorporation into oligomeric libraries. The libraries are synthesized using combinatorial techniques from subsets of available monomers to generate molecular ensembles from which can be selected those with maximum affinity for the target protein. The number of monomers used in the library synthesis is chosen to exploit the full capability of the screening technology used to identify the best ligand.

There is no uniform element in the monomer corresponding to the sugar group of an oligonucleotide, or the amide backbone of peptides, PNA's, hydroxyproline or N-substituted glycine derivatives, or similar types of oligomers. Therefore, there is a high degree of variability in the molecular geometries that can be introduced into the product oligomers.

The nature of the phosphorus linking group in these compounds can be varied at any position to create a greater diversity per unit length of the oligomer than would otherwise be achieved with one type of linkage, such as a phosphodiester or amide. The flexibility of this linkage is also controllable by changing between freely rotatable phosphodiesters, and rotationally constrained phosphoramidates or other esters with bulky groups directly attached to phosphorus. In addition, the gross physical characteristics of the molecules can be varied from anionic to neutral to cationic, with all intermediate cases represented.

Experiments have shown that representative oligomers of this invention are very stable in serum under conditions which rapidly degrade oligonucleotides. Therefore, any lead compound selected from an oligomeric phosphorus ester library is potentially a drug candidate, as compared to oligonucleotide or peptide leads which are readily degraded and therefore most likely require chemical modification to serve as a legitimate drug candidate.

The unique and advantageous aspects of the present invention lie principally in the highly variant set of monomers employed for the synthesis of combinatorial libraries, and the choice of the linking groups in the product oligomers. The monomers fulfill two roles: a structural function whereby the molecular geometry and flexibility of the oligomer are controlled, and secondly, they contain appropriate functional groups to bind to protein or other biological targets. As stated above, the monomers do not contain the sugar or sugar analog element that is found in most other types of oligomers. Instead, any molecule containing two hydroxyl functions may be considered a suitable monomer candidate. By employing such variant compounds to construct oligomers, large ensembles of molecules with highly variant geometries can be generated. In addition, control can be excercised over the degree of flexibility in these compounds. For example, constraints can be introduced by either using intrinsically inflexible monomers, or monomers in which the two hydroxy groups are vicinal and the resultant steric congestion limits certain bond rotations. Alternatively, it may be desirable to introduce a flexible element into some portion of a molecule, and this could be easily achieved by employing a suitably derivatized α,ω-aliphatic diol. The importance of being able to modulate the conformational freedom of potential drug candidates in order to optimize their binding and selectivity profiles is a well understood principal in medicinal chemistry. Also, conformationally-constrained compounds are desirable as lead molecules in any rational drug design program.

In relation to the ability of the monomers to present appropriate binding groups to protein targets, essentially all common organic functional groups, when suitably protected, are compatible with the condensation chemistry that is employed for synthesizing the oligomers. The monomers used for the synthesis of a library directed against a particular biological target are chosen to contribute to the affinity for the target. To this end, the monomers can be subdivided into a range of different categories describing their principal mode of binding, examples being; hydrophobic, hydrogen bond donor, hydrogen bond acceptor, electrostatic cation, and electrostatic anion. Obviously, many monomers contain multiple binding elements and can be assigned to more than one category.

In this invention, each phosphorus linking element connecting the monomer units can be independently modified to both introduce additional binding functionality, and also control the structural flexibility of the oligomers. These linkages can exist either as phosphates, phosphorothioates or phosphoramidates, depending on the oxidation conditions employed for their synthesis. Additional binding groups can be introduced into the oligomers by the oxidation of intermediate H-phosphonate linkages using a diverse range of primary and secondary, simple or highly functionalized amines, an obvious example being amino acids. By using secondary and α-branched amines, significant rotational constriction of the phosphorus linkage can be achieved, and this constitutes another mechanism for introducing conformational constraint.

To complement the above methods for the introduction of conformational constraints, an extension is the synthesis of libraries of cyclic analogs of oligomeric phosphorus esters. These compounds can be prepared via oxidation reactions of thiol groups to produce cyclic disulfides, such as is described in commonly assigned copending U.S. patent application Ser. No. 08/004,284. This creates structures such as the disulfide-bridged cyclic oligomer as described in Example 45 herein. Other methods for cyclization can be employed, using methods known to those skilled in the art.

A primary utility of oligomeric phosphate ester libraries is the screening of such mixtures for binding activity to particular biological targets, including but not limited to proteins, with the objective of identifying therapeutically important molecules. The structures of the oligomers of the present invention that bind with high affinity to a biological target can be deduced using procedures such as that described in commonly assigned, copending U.S. patent application Ser. No. 08/223,519, or by the use of encoded libraries similar to those described in Gallop et al., 1994, or by other methods obvious to those skilled in the art.

Another application of this invention is the use of these compounds as glycosaminoglycan mimetics. Glysoaminoglycans are large sulfated oligosaccharides that bind to a range of important regulatory proteins. Work directed at the synthesis of mimetics of these compounds has focused on the preparation of structurally defined heparin oligosaccarides and sulfated dextrans (Lander 1994).

A particular example of this application is in the area of glycosaminoglycan mimetics. Glycosaminoglycans are multiply charged, anionic, sulfated polysaccarides that are typically around 250 saccharide units in length. They are known to modulate a series of biochemical processes by binding to certain polycationic receptor sites on proteins, and play key roles in a conditions as diverse as cancer and Alzheimer's disease. The interaction between the protein and the glycosaminoglycan is mostly electrostatic in nature, and consequently the dissociation constant for these interactions is comparatively large, typically in the range $10^{-5}$ to $10^{-8}$ M. One approach to the design of mimetics of this class of compound which would have therapeutic application, would require the synthesis of much lower molecular weight anionic molecules, containing certain hydrophobic binding groups. (Lander, 1994). These criteria are met in the oligomeric phosphorus ester libraries of the type discussed in Example 43.

In another aspect, the oligomers of the present invention can be used in a method for detecting the presence or absence of a target molecule in a sample, or determining the number of such molecules in a sample. In such methods, the oligomer can be labeled, exposed to target, and the amount of labeled oligomer which is bound to the target is quantified by measurement of the signal derived from the label. The label can be radioactive or non-radioactive. Radioactive labels include phosphorus-32, sulfur-35, tritium, and heavy metal isotopes which can be trapped by chelating groups attached to the oligomer. Non-radioactive labels include, but are not limited to, biotin and its analogs, fluorescein, tetramethyl-rhodamine, substrates for enzymes such as alkaline phosphatase or horseradish peroxidase, haptens such as dinitrophenyl or digoxigenin and other labels known to those experienced in the art. Thus, oligomers of the present invention can be used for diagnostics in a manner similar to methods employed for antibody-based diagnostics. The same labeling techniques may also be employed in the protocols for the identification of protein ligands, discussed above.

Figure 1:
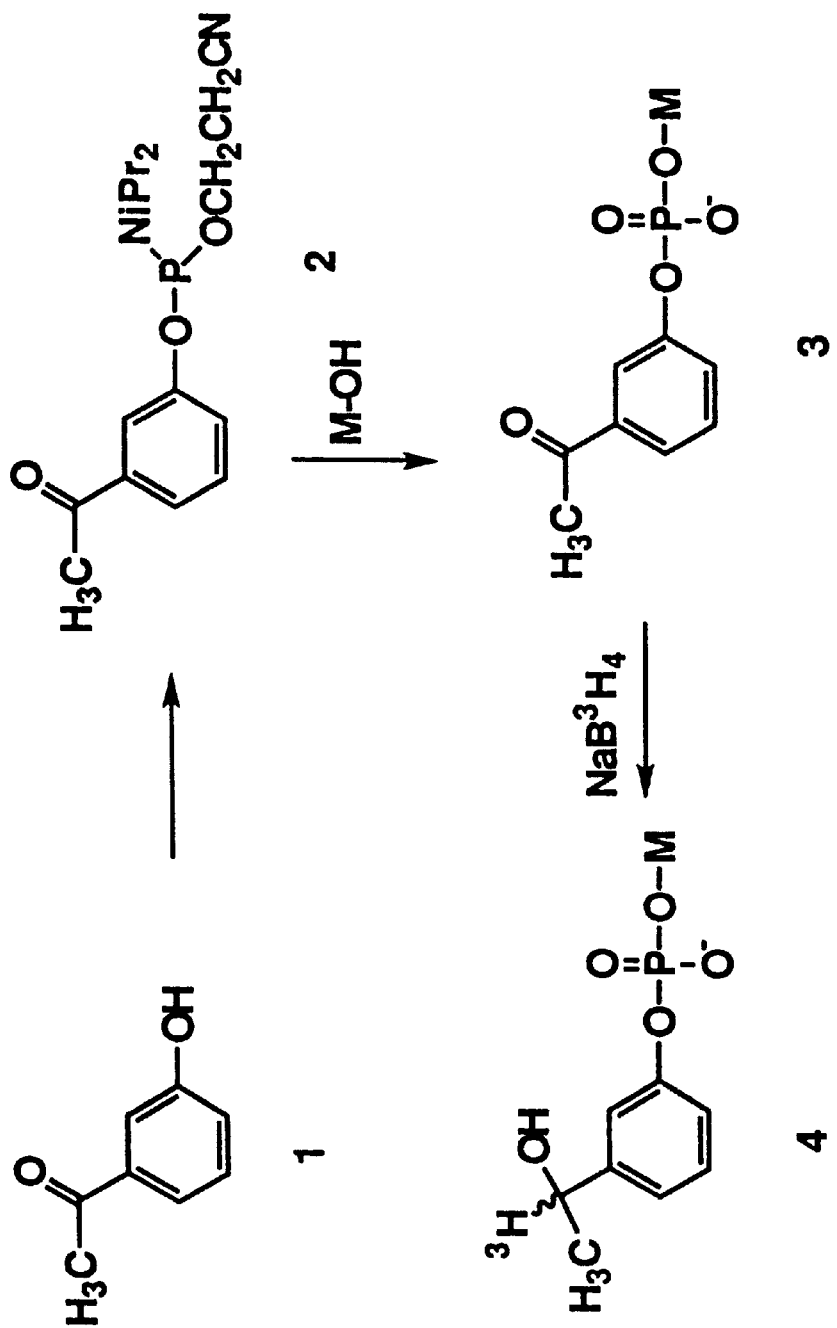
FIG. 1 shows a method for introduction of a tritium label by reduction of a hydroxyacetophenone functionality.

Preferred hydrogen bond donors are functionalities containing amine, amide, imide, alcohol and thiol moieties. Examples of such compounds are those wherein $R_1$ is a 3-substituted dihydroxyalkyl indole (e.g., indolyl-dihydroxypropane), or a bis(hydroxyalkyl)-substituted heterocycle (e.g., 1,2-dihydroxyethylthiazole and pyridoxine) or a 2-amino-1,3-propandiol (e.g.; thiomicamine).

Preferred hydrogen bond acceptor compounds include those containing amine or ether moieties. Examples of such compounds are those wherein $R_1$ is a purine or pyrimidine substituted 1,2-diol (e.g., theophylline) or a bis (hydroxyalkyl)-substituted heterocycle (e.g., 1,2-dihydroxyethylthiazole and pyridine dimethanol) or a 5-substituted 2-hydroxymethyl 3-hydroxy-tetrahydrofuran (e.g., 1,2 dideoxy-D-ribose).

Preferred hydrophobic groups are alkyl groups and aromatic rings. Examples of such compounds are those wherein $R_1$ is a substituted 1,3-dihydroxyalkane (e.g. 4-methoxyphenoxy-1,3-propanediol), a substituted 1,2-dihydroxy alkene (e.g.; 1,2-dihydroxy-3-butene), a 3,3-disubstituted 3-amino-1,2-propanediol (e.g., 3-benzyl-3-methylamino-1,2-propanediol and 3,3-diethylamino-1,2-propanediol), a substituted or unsubstituted alicyclic diol wherein the ring size is from 4–12 (e.g. cyclooctanediol and cyclopentanediol), a 3-substituted dihydroxyalkyl indole (e.g., indolyl-dihydroxypropane) or a substituted or unsubstituted hydroxyalkyl phenol (e.g., tetralin and hydroxybenzyl alcohol) or a 1,2-dihydroxy alicyclic, dicarboxylic acid (e.g., tricyclononene dicarboxylic acid).

Preferred electrostatically charged functionalities include anionic functionalities, such as carboxylic, sulfonic and phosphoric acid and tetrazole moieties. Examples of such compounds are those wherein $R_1$ is a dihydroxy-substituted carboxylic acid (e.g., cyclopentanediol acetic acid) or a 1,2-dihydroxy alicyclic dicarboxylic acid (e.g., tricyclononene dicarboxylic acid).

Preferred electrostatically charged functionalities also include cationic functionalities. Examples of such compounds are those wherein $R_1$ is a substituted 1,3-dihydroxyalkane (e.g., 2-amino-1,3-propanediol, 1-phenyl-2-amino-1,3-propanediol and thiomicamine), a 3,3-disubstituted 3-amino-1,2-propanediol (e.g., 3,3-diethylaminopropanediol and 3-benzyl-3-methylamino-1,2-propanediol) or a bis(hydroxyalkyl)-substituted heterocycle (e.g., 1,2-dihydroxyethyl-thiazole and pyridine dimethanol).

Preferred heterocyclic dihydroxy alcohols are those containing an indole, thiazole, imidazole, purine or pyrimidine ring structure. Examples of such compounds are those wherein $R_1$ is a 3-substituted dihydroxyalkyl indole (e.g., indolyl-dihydroxypropane) or a purine or pyrimidine substituted 1,2-diol (e.g., 2,3-dihydroxypropyl-theophylline) or a bis(hydroxyalkyl)-substituted heterocycle (e.g., thiazole and pyridine dimethanol) or a 5-substituted 2-hydroxymethyl 3-hydroxy-tetrahydrofuran (e.g., 1,2 dideoxy-D-ribose).

Preferred alicyclic dihydroxy alcohols are those containing a cyclopentane or cyclooctane ring structure, including those which are diols and which are substituted with at least one carboxylic acid moiety. Examples of such compounds are those wherein $R_1$ is a substituted or unsubstituted alicyclic diol wherein the ring size is from 4–12 (e.g. cyclooctanediol and cyclopentanediol) and those wherein $R_1$ is a dihydroxy-substituted carboxylic acid (e.g., cyclopentanediol acetic acid).

Preferred polycyclic dihydroxy alcohols are those containing a bicyclic or tricyclic ring structure, including alkanes such as a bicycloheptane, alkenes such as tricyclonene diol and polycyclic arenes such as diphenyl bicyclooctane diol. Examples of such compounds are those wherein $R_1$ is a dihydroxy substituted polycyclic compound (e.g. tricyclononene diol dicarboxylic acid and pinanediol).

Examples of non-nucleotide phosphorus oligomers where $R_1$ is a condensation product of an aliphatic acyclic hydrocarbon diol wherein the diol hydroxyl groups are non-vicinal or are substituted include those formed from monomers wherein $R_1$ is 1,3-propanediol or 2-amino-1,3-propanediol.

Examples of non-nucleotide phosphorus oligomers where $R_1$ is a condensation product of a purine or pyrimidine substituted variant of the diols of (i) or of aliphatic acyclic hydrocarbon vicinal diols include those formed from monomers wherein $R_1$ is a purine substituted 1,2-diol (e.g. 2,3-dihydroxypropyl theophylline).

Examples of non-nucleotide phosphorus oligomers where $R_1$ is a condensation product of an acyclic aliphatic diol having an amino group with at least one hydrogen substitution moiety include those formed from monomers wherein $R_1$ is 3-diethylamino-1,3-propanediol.

Examples of non-nucleotide phosphorus oligomers where $R_1$ is a condensation product of an alicyclic or polycyclic diol, optionally substituted with a carboxy or carboxyalkyl substituent include those formed from monomers wherein $R_1$ is cyclopentanediol, cyclooctanediol, and those formed from monomers wherein $R_1$ is a dihydroxy-substituted carboxylic acid (e.g., cyclopentane diol acetic acid) or a 1,2-dihydroxy alicyclic dicarboxylic acid (e.g., tricyclononene diol dicarboxylic acid).

Examples of non-nucleotide phosphorus oligomers where $R_1$ is a condensation product of a hydroxy or hydroxyalkyl substituted tetrahydrofuran include those formed from monomers wherein $R_1$ is 1,2-dideoxy-D-ribose.

Examples of non-nucleotide phosphorus oligomers where $R_1$ is a condensation product of an indole substituted acyclic aliphatic diol include those formed from monomers wherein $R_1$ is indolyl-dihydroxypropane.

Examples of non-nucleotide phosphorus oligomers where $R_1$ is a condensation product of an aromatic ring or ring system having two substitutions independently selected from the group consisting of hydroxy or hydroxyalkyl include those formed from monomers wherein $R_1$ is 2,6-bis-hydroxymethyl-pyridine.

Examples of non-nucleotide phosphorus oligomers where $R_1$ is a condensation product of a heterocyclic compound having two substitutions independently selected from the group consisting of hydroxy or hydroxyalkyl include those formed from monomers wherein $R_1$ is 1,2,3,4-tetrahydro-1,5-dihydroxy-naphthalene.

Examples of non-nucleotide phosphorus oligomers where $R_1$ is a condensation product of a dihydroxyalkyl thiazole or dihydroxyalkyl oxazoline include those formed from monomers wherein $R_1$ is 2-amino-4-(1,2-dihydroxyethyl)-1,3-thiazole.

The structures of the oligomers of the present invention that bind with high affinity to a protein target can be deduced using procedures including, but not limited to, those described in commonly assigned, copending U.S. patent application Ser. No. 08/223,519, or by the use of encoded libraries similar to those described in Gallop et al., 1994.

The libraries are typically synthesized from a diverse pool of about 20 to 30 of such monomer units which are chosen to ensure sufficient diversity with regard to chemical functionality, shape and physical properties, such as charge and hydrophobicity. However, larger or smaller numbers of such monomers can be employed. For the purpose of synthesizing the libraries, these monomers are prepared as 4,4'-dimethoxytrityl (DMT)-protected phosphoramidites and condensed together using known techniques (see Andrus et al., 1988) to produce oligomers with negative charges on the phosphorus backbone. Phosphodiester or phosphorothioate backbones can be produced by these methods. Alternatively, the monomers can be prepared as H-phosphonate derivatives which can be coupled together to produce oligomers using standard procedures (Milligen/Biosearch Inc., Novato Calif., H-phosphonate Synthesis Information). The oligomer H-phosphonate intermediates can be subsequently oxidized with iodine and water to produce phosphodiester or with a sulfur reagent to give phosphorothioate linkages.

An example of a simple oligomeric phosphodiester compound of this type which has already been synthesized is as follows:

Another aspect of the present invention is the introduction of additional diversity into the backbone of the oligomers by oxidation of the H-phosphonate intermediates with a diverse set of amines to produce phosphoramidate derivatives. The amines can be selected so as to introduce aliphatic groups, aromatic groups, uncharged polar groups such as hydrogen bond donor or acceptor groups, negatively charged groups and/or positively charged groups. Thus the overall structural diversity of the oligomer can be greatly increased above that which can be achieved when the backbone is comprised exclusively of phosphodiester groups. Examples of amines which can be reacted with oligomer H-phosphonate intermediates to produce oligomer phosphoramidates are as follows: 2-(2-aminoethyl)pyridine; 1-(2-aminoethyl)piperidine; 2-(3,4-dimethyloxyphenyl)ethylamine; 4-(2-aminoethyl)-morpholine; 1-(3-aminopropyl)-4-methylpiperazine; 1-(3-aminopropyl)-2-pyrrolidinone; 1-(3-aminopropyl)imidazole; 1-(2-aminoethyl)pyrrolidine; 3-aminopropionitrile; 2-(2-aminoethyl)-1-methyl-pyrrolidine; 4-fluorophenethylamine; 4-bromophenethylamine; aminomethyl-cyclopropane; 3,3-diphenylpropylamine; formylpiperazine; trifluoromethylphenylpiperazine; thiomorpholine; 1-(2-pyridyl)piperazine; homopiperazine; hexamethyleneimine; cis-2,6-dimethylmorpholine; 2,5-dimethylphenylpiperazine; 3,5-dimethylpiperidine; 1-(4-fluorophenyl(piperazine; N-(3,4-dichlorophenyl)piperazine; 2-(4-chlorophenyl)ethylamine; 4-piperazineacetophenone; 4-piperidinopiperidine; 2-thiophenemethylamine; furfurylamine; heptamethyleneimine; and 1-(4-methoxyphenyl)piperazine.

Other amines can be employed for this purpose as will be evident to those skilled in the art, and amino acid derivatives can also be used in the same way. Thus oligomers can be constructed that can be either anionic, neutral or cationic in character. Using this method, a highly diverse library of molecules with lower molecular weights can be produced.

An example of an oligomeric phosphoramidate of this type which can be synthesized is as follows:

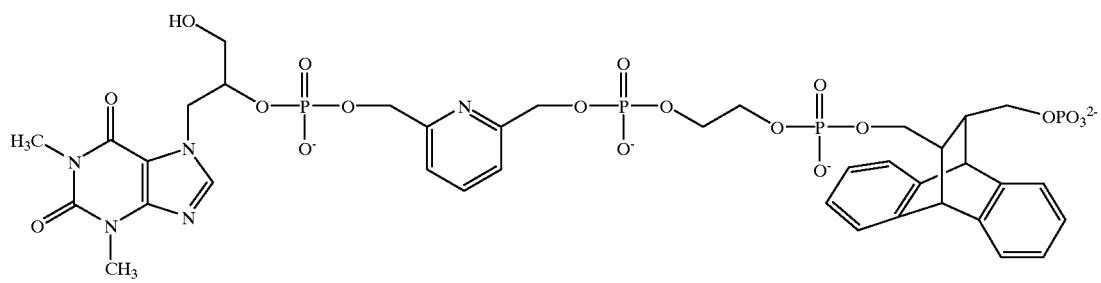

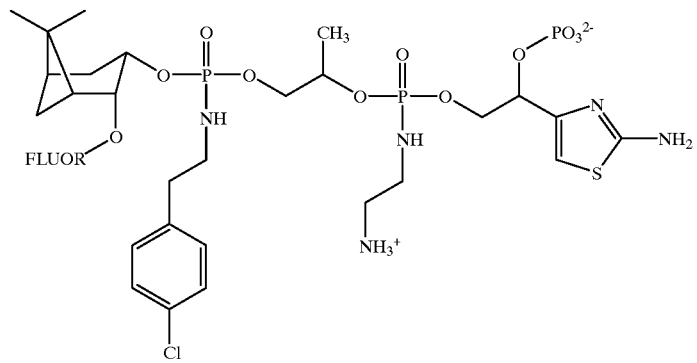

Another aspect of the invention relates to the use of preferred labeling and protecting groups, for example as $B_1$ and/or $B_2$. In one embodiment $B_1$ and/or $B_2$ is a group containing at least one tritium atom for the purposes of detection. This approach to tritium labeling employs a "labeling monomer" which introduces a reactive aldehyde or ketone group at a late stage of synthesis, followed by reduction with labeled borohydride to introduce the tritium label. In the resulting compound at least one of $B_1$ and $B_2$ is a phosphodiester attached to a tritium-labeled p- or m-1-hydroxy ($C_1$–$C_6$ alkyl)phenyl. An important consideration requires that the labeling group should also be stable to the alkaline conditions used to cleave the material from the solid support. Simple glycol groups with flexible backbones were therefore ruled out since Fontanel et al. have shown that oligonucleotides terminated with glycol moieties undergo degradation in concentrated ammonia at 55° C., presumably by attack of the free hydroxyl group, on the adjacent phosphate group followed by cyclization and elimination of the terminal unit. For these reasons hydroxyacetophenone was selected as a commercially available starting material for the labeling monomer approach, since the possibility of attack of the hydroxyl group produced by reduction on the adjacent phosphorus atom was eliminated because of the rigidity of the benzene ring. A comparison of reductions of the ketone group of both p- and m-hydroxyacetophenone indicated that the meta isomer was more easily reduced using sodium borohydride, this isomer was selected for further studies. The phosphoramidite derivative 2 was prepared by a conventional procedure (Beaucage et al.) and trial experiments with model reactions indicated that this could be coupled to support-bound thymidine and oxidized to produce the diester 3a. Other methods can be used to prepare 3a. For example, 1 can be converted into an H-phosphonate derivative which can be coupled to a support bound nucleoside using standard chemistry known to those in the art.

The reduction of 3a with sodium borohydride was investigated to determine the minimum amount of reagent needed for the tritiation experiment and to confirm the identity of the reduction product. Reduction was studied both in solution and on a solid support. Complete reduction in solution could be obtained using one equivalent of borohydride in ethanol, and evidence for the structure of the reduced product 4a was obtained from electrospray MS, which showed a molecular ion at 441 for the reduced compound as expected, versus 439 for the ketone starting material 3a. Upon reduction, proton NMR indicated the disappearance of signals assigned to the acetophenone methyl group at 2.5 ppm as expected for the conversion of a ketone to an alcohol group.

In another embodiment relating to nucleotides as labeling/protecting groups $B_1$ and $B_2$, libraries of non-nucleotide phosphorus ester oligomers were prepared using a conventional thymidine derivatized solid support, which after cleavage from the support results in each member of the library having a thymidylate protecting group attached to its terminus at $B_2$. This thymidine group plays a role as a protecting group in stabilizing the libraries to degradation by the concentrated ammonia conditions required for cleavage from the support. In addition to thymidine, a wide variety of other nucleosides can be used as protecting groups for this purpose. In the absence of such a protecting group, compounds with flexible terminal groups might be expected to undergo degradation by attack of the terminal hydroxyl group on the neighboring phosphoryl group to produce a cyclic phosphate intermediate followed by elimination of the remainder of the molecule. Degradation of this type has been demonstrated with oligonucleotides which terminated in ethylene glycol units (Fontanel et al.).

Figure 2:
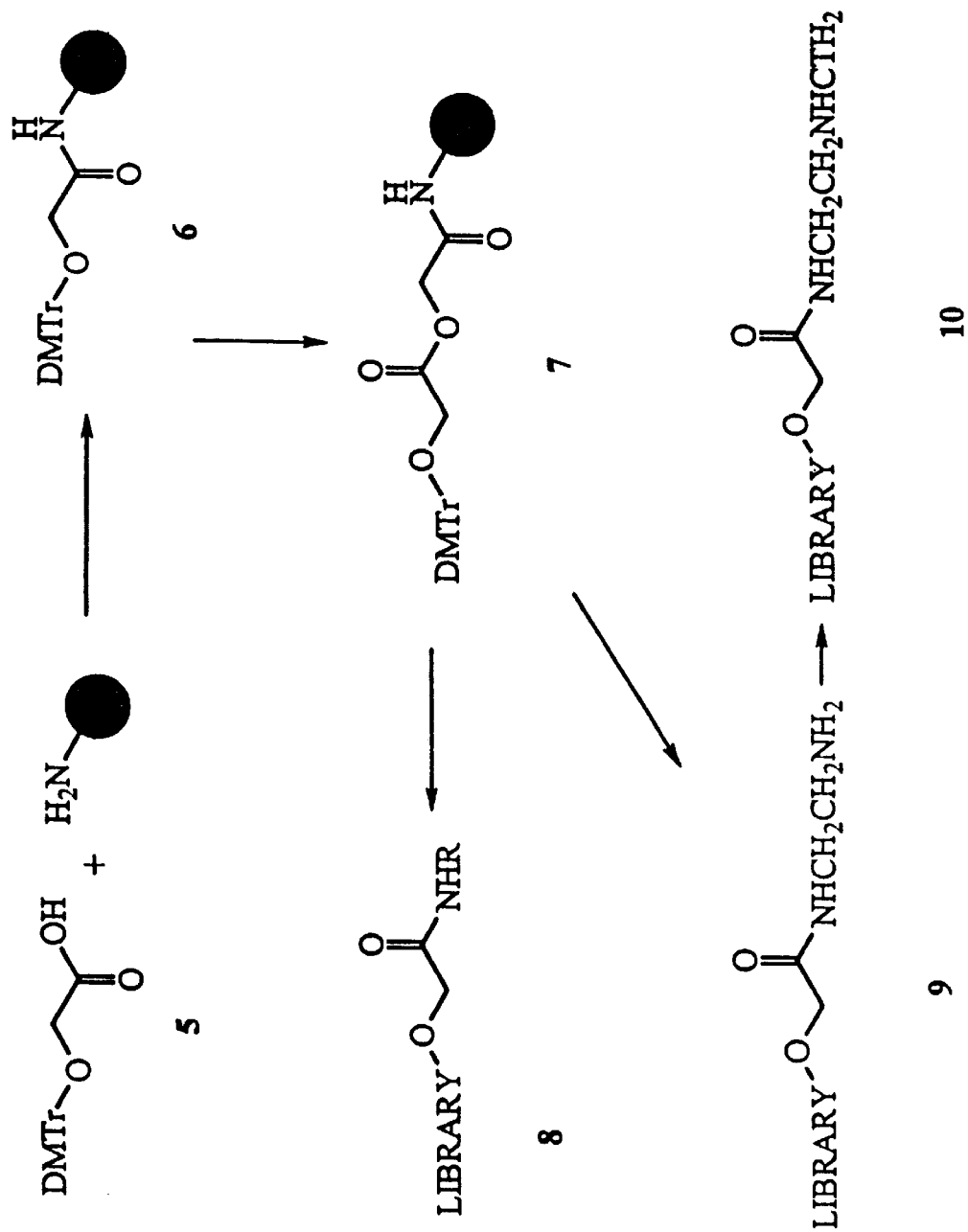
FIG. 2 shows a method for the introduction of glycolic amide groups at the terminus of a library (Structure 8), including a method for the introduction of a radioactive label (Structure 10).

Another embodiment provides glycolic amide protecting groups $B_1$ and $B_2$. Methods have been developed for the synthesis of other protecting groups which impart stability to the libraries when subjected to alkaline degradation. One approach was to prepare a support which, when treated with ammonia, generates an amide group, and is similar to a reported method for generating 3'-endcapped oligonucleotides (Hovinen et al.). Amino-derivatized controlled pore glass was treated with O-dimethoxytrityl glycolic acid (5, FIG. 2) to give the solid supported amide derivative 6, which was detritylated and coupled to a second molecule of 5 to give the diglycolic ester derivative 7. This support was used as a replacement for the thymidine derivatized support for the synthesis of libraries. After completion of the synthesis, the library was cleaved from the support by reaction with ammonia, which cleaved the ester group to produce compounds which terminated with glycolic amide functionalities 8, where R=H. Removal of the thymidine groups and substitution with glycolic amide groups in this way results in libraries of smaller molecular weight without bulky protecting groups.

This glycolic acid derivatized support as discussed above can be used to introduce another element of diversity into combinatorial libraries by cleavage using a variety of primary or secondary amines to produce substituted amides. This is achieved by treatment of the oligomer attached to the solid support with a variety of amines to produce oligomers of structure 8, (FIG. 2), where R=a wide range of substituted or unsubstituted aliphatic or aromatic groups.

In another variation, the glycolic acid derivatized support can be treated with a diamine such as ethylenediamine to produce a glycolic amide of structure 9, which can be used to introduce a radioactive label by reductive amination with formaldehyde and tritium labeled borohydride to give a labeled library such as 10, where T is a tritium atom.

The diversity in this type of oligomer is derived from both the monomer units as described in Examples 1–41, as well as the amines which are attached to the phosphorus atoms. The library can be prepared by solid-phase synthesis on a solid support, using a pool and divide strategy employing techniques already reported (Furka et al., 1991).

Known chemical and physical properties of the target can be used to dictate the choice of monomers that are used in the construction of the library. The libraries can be assembled from a monomer subset which is weighted to have a high likelihood of affinity for the binding site on the target as possible, thereby increasing the probability of identifying a suitable ligand. The weighting of the subset can be achieved through the use of molecular modeling techniques. In the absence of such information, a monomer subset is chosen to be as diverse as is considered desirable. The number of monomers that may be employed for the synthesis of a library is limited by the screening technology used in identifying potential ligands.

EXAMPLE 1

Synthesis of 5'-O-(4,4'-dimethoxytrityl)-1,2-dideoxy-D-ribose-3'-O-(N,N-diisopropylamino-2-cyanoethyl)-phosphoramidite 5'-(4,4'-dimethoxytrityl)-1,2-dideoxy-D-ribose (10.7 g) was prepared according to the method of (Grollman et al., 1987). This DMT derivative (10.7 g, 25 mmol) was dried over $P_2O_5$ under high vacuum, dissolved in dry dichloromethane (60 mL) under nitrogen, then treated with diisopropylethylamine (13.2 g, 102 mmol) and 2-cyanoethoxy-(N,N-diisopropylamino)chlorophosphine (9 g, 38 mmol). After stirring for 2 hours dry methanol (0.5 mL) was added and the reaction mixture was stirred for 20 minutes, poured into 5% aqueous sodium bicarbonate (250 mL), and extracted with ethyl acetate (2×200 mL). The organic layers were washed with saturated aqueous sodium chloride (200 mL), dried overnight over anhydrous sodium sulfate, concentrated to an oil and coevaporated with toluene (20 mL), followed by methanol (20 mL), hexane (20 mL), and dichloromethane (20 mL). The crude product (13.79 g) was purified by Normal Phase High Pressure Liquid Chromatography (NP-HPLC) eluting with a gradient of dichloromethane/hexane (10 to 0%) and then eluting with a gradient of dichloromethane/methanol (0 to 2%). The purities of the fractions were monitored by TLC and fractions containing pure material were combined and evaporated to dryness to give 5'-O-(4,4'-dimethoxytrityl)-1,2-dideoxy-D-ribose-3'-O-(N,N-diisopropylamino-2-cyanoethyl)-phosphoramidite (13.8 g) as an oil having the following structure:

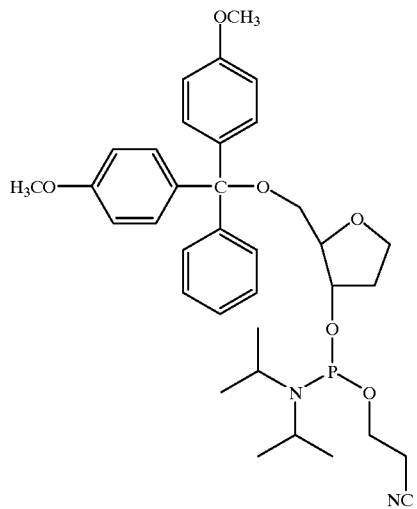

$^1$H NMR (500 MHz) DMSO δ (ppm) 7.38–6.86 (m, 13H, aromatic), 5.74 (s, 1H), 4.32–4.26 (m, 1H), 3.94–3.44 (m, 3H), 3.72 (s, 6H, $OCH_3$), 3.04–2.93 (m, 2H), 2.75–2.71 (m, 2H, $CH_2$), 2.64–2.61 (m, 2H, $CH_2$), 2.09–2.03 (m, 2H, CH), 1.95–1.91 (m, 1H, H-2"), 1.87–1.83 (m, 1H, H2'), 1.15–0.95 (m, 12H, 4×$CH_3$). $^{31}$P NMR (202 MHz) DMSO δ (ppm) 147.5, 147.3.

EXAMPLE 2

Synthesis of 1-(4,4'-dimethoxytrityl)-propanediol-3-(N,N-diisopropylamino-2-cyanoethyl)-phosphoramidite 1-(4,4'-dimethoxytrityl)-1,3-propanediol (6.8 g) was prepared by the method of Seela and Kaiser (1987). This DMT derivative (6.8 g, 18 mmol) was dissolved in dry dichloromethane (35 mL) under nitrogen and treated with diisopropylethylamine (9.3 g, 72 mmol), and 2-cyanoethoxy-(N,N-diisopropylamino)chlorophosphine (6.4 g, 27 mmol). After stirring for 30 minutes, the mixture was concentrated and 5% aqueous sodium bicarbonate (250 mL) was added. The mixture was extracted with ethyl acetate (3×200 mL), the organic layers were washed with saturated aqueous sodium chloride (200 mL), dried over anhydrous sodium sulfate, and concentrated to give the crude product (12 g) as an oil. This was purified by NP-HPLC eluting with a gradient of dichloromethane/hexane (50 to 25%). The purities of the fractions were monitored by TLC and fractions containing pure material were combined and evaporated to dryness to give 1-(4,4'-dimethoxytrityl)-1,3-propanediol-3-(N,N-diisopropylamino-2-cyanoethyl)-phosphoramidite (10.3 g) as a yellow oil having the following structure:

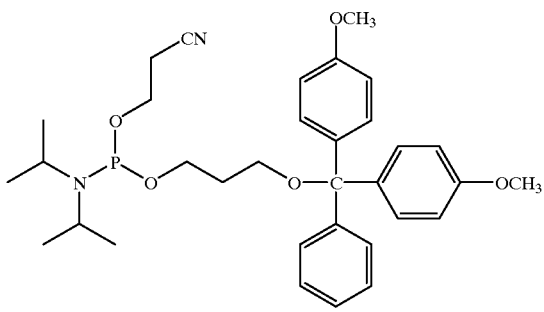

¹H NMR (500 MHz) DMSO δ (ppm) 7.37–6.83 (m, 13H, aromatic), 3.72 (s, 6H, OCH₃), 3.69–3.60 (m, 2H, CH₂-3), 3.50–3.44 (m, 2H, CH₂), 3.09–3.01 (m, 2H, CH₂), 2.68 (t, 2H, J=5.8 Hz, CH₂-1), 1.84–1.79 (m, 2H, CH₂-2), 1.10 (d, 6H, J=6.8 Hz, 2×CH₃), 1.03 (d, 6H, J=6.8 Hz, 2×CH₃). ³¹P NMR (202 MHz) DMSO δ (ppm) 146.9.

EXAMPLE 3

Synthesis of 1-(4,4'-dimethoxytrityl)-3-(4-methoxyphenoxy)-1,2-propanediol-2-(N,N-diisopropylamino-2-cyanoethyl-phosphoramidite 3-(4-Methoxyphenoxy)-1,2-propanediol (4 g, 20 mmol) in dry pyridine (50 mL) was treated with DMT chloride (8.2 g, 24 mmol), triethylamine (2.9 g, 28 mmol), and dimethylaminopyridine (120 mg, 1 mmol) and stirred at room temperature for 16 hours. The mixture was poured into 5% aqueous sodium bicarbonate (250 mL), extracted with dichloromethane (3×200 mL). The combined organic layers were washed with saturated aqueous sodium chloride (250 mL) and dried over anhydrous sodium sulfate. The solid was filtered off and the filtrate was evaporated to dryness and coevaporated with toluene, methanol, hexane, and dichloromethane to give crude product which was purified by NP-HPLC eluting with a gradient of dichloromethane/hexane (90 to 0%). The purities of the fractions were monitored by TLC and fractions containing pure material were combined and evaporated to dryness to give 1-(4,4'-dimethoxytrityl)-3-(4-methoxyphenoxy)-1,2-propanediol (9.7 g) as a pale yellow oil having the following structure:

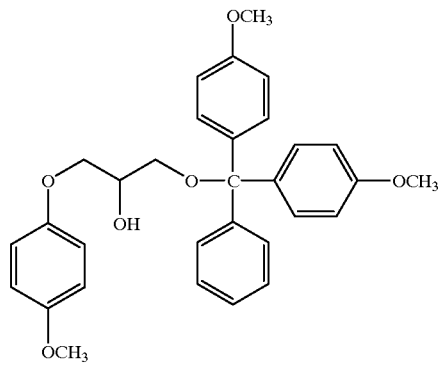

¹H NMR (500 MHz) DMSO δ (ppm) 7.39–6.80 (m, 13H, aromatic), 5.09 (d, 1H, J=4.7, OH), 3.96–3.87 (m, 3H, CH₂ & CH), 3.72 (s, 6H, 2×OCH₃), 3.68 (s, 3H, OCH₃), 3.06–3.03 (m, 2H, CH₂). TLC Rf 0.16 (9:1 dichloromethane/methanol).

This DMT derivative (3.25 g, 6.5 mmol) was dissolved in dry dichloromethane (20 mL) under nitrogen and treated with diisopropylethylamine (2.5 g, 19.5 mmol), and 2-cyanoethoxy-(N,N-diisopropylamino)chlorophosphine (2.3 g, 9.7 mmol). After stirring for 1 hour, the mixture was poured into 5% aqueous sodium bicarbonate (200 mL). The mixture was extracted with ethyl acetate (3×200 mL), the organic layers were washed with saturated aqueous sodium chloride (200 mL), dried over anhydrous sodium sulfate, and concentrated to give the crude product (4.8 g) as an oil. This was purified by NP-HPLC eluting with a gradient of dichloromethane/hexane (90 to 0%). The purities of the fractions were monitored by TLC and fractions containing pure material were combined and evaporated to dryness to give 1-(4,4'-dimethoxytrityl)-3-(4-methoxyphenoxy-1,2-propanediol-2-(N,N-diisopropylamino-2-cyanoethyl)-phosphoramidite (3.4 g, 4.9 mmol) as a colorless oil having the following structure:

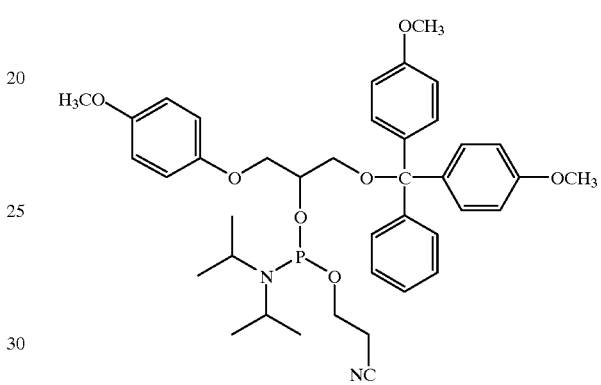

¹H NMR (500 MHz) DMSO δ (ppm) 7.40–6.77 (m, 13H, aromatic), 4.21–3.95 (m, 4H,), 3.72 & 3.71 (s, 6H, OCH₃, 2 diastereomers), 3.68 & 3.67 (s, 3H, OCH₃, 2 diastereomers) 3.66–3.46 (m, 4H, CH₂-3), 3.22–3.09 (m, 3H, CH₂), 2.72 (t, 1H, J=5.8 Hz,), 2.63 (t, 1H, J=5.6 Hz), 1.22–0.92 (m, 12H, 4×CH₃). ³¹P NMR (202 MHz) DMSO δ (ppm) 149.6, 149.2.

EXAMPLE 4

Synthesis of 1-(4,4'-dimethoxytrityl)-3-(diethylamino)-1,2-propanediol-2-(N,N-diisopropylamino-2-cyanoethyl)-phosphoramidite 3-(Diethylamino)-1,2-propanediol (5 g, 34 mmol) in dry pyridine (100 mL) was treated with DMT chloride (13.8 g, 41 mmol), triethylamine (4.8 g, 48 mmol), and dimethylaminopyridine (207 mg, 1.7 mmol) and stirred at room temperature for 4 hours. The mixture was concentrated by rotary evaporation, dissolved in dichloromethane (200 mL) and poured into 5% aqueous sodium bicarbonate (250 mL). The layers were separated and the aqueous layer was extracted with dichloromethane (2×200 mL) and the combined organic layers were washed with saturated aqueous sodium chloride (250 mL) and dried over anhydrous sodium sulfate. The solid was filtered off and the filtrate was evaporated to dryness and coevaporated with toluene, methanol, hexane, and dichloromethane to give crude product (20 g) which was purified by column chromatography on silica gel (300 g) eluting with a gradient of dichloromethane/methanol (0 to 4%). The purities of the fractions were monitored by TLC and fractions containing pure material were combined and evaporated to dryness to give 1-(4,4'-dimethoxytrityl)-3-(diethylamino)-1,2-propanediol (14.9 g) as a brown oil having the following structure:

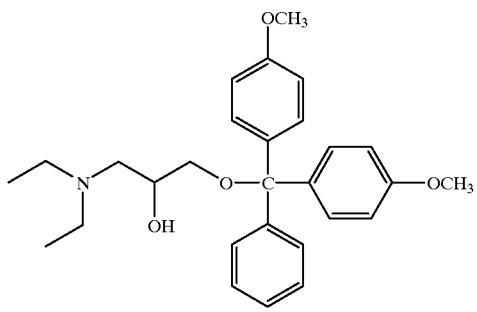

¹H NMR (500 MHz) DMSO δ (ppm) 7.42–6.50 (m, 13H, aromatic), 4.47 (br s, 1H, OH), 3.72 (s, 6H, 2×OCH₃), 3.65 (br s, 1H, CH-2) 2.95–2.88 (m, 2H, CH₂-3), 2.40–2.39 (m, 4H, 2×N—CH₂), 2.35–2.28 (m, 2H, CH₂-1), 0.84 (t, 6H, J=6.9 Hz, 2×CH₃). TLC Rf 0.4 (9:1 dichloromethane/methanol).

This DMT derivative (0.5 g, 1.1 mmol) was dissolved in dry dichloromethane (4 mL) under nitrogen and treated with diisopropylethylamine (0.43 g, 3.3 mmol), and 2-cyanoethoxy-(N,N-diisopropylamino)chlorophosphine (0.39 g, 1.7 mmol). After stirring for 2.5 hours, dry methanol (0.5 mL) was added and the mixture was evaporated to dryness, dissolved in 5% aqueous sodium bicarbonate, and extracted with ethyl acetate (3×75 mL). The organic layers were washed with saturated aqueous sodium chloride (100 mL) and dried over anhydrous sodium sulfate. The solid was filtered off and the mixture evaporated to dryness to give crude 1-(4,4'-dimethoxytrityl)-3-(diethylamino)-1,2-propanediol-2-(N,N-diisopropylamino-2-cyanoethyl)-phosphoramidite (0.79 g) as an oil having the following structure:

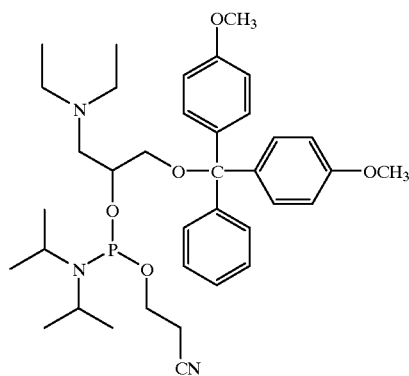

¹H NMR (500 MHz) DMSO δ (ppm) 7.48–6.95 (m, 13H, aromatic), 4.57–2.26 (m, 11H,), 3.72 (s, 6H, 2×OCH₃), 2.43–2.26 (m, 4H, 2×CH₂), 1.25–1.06 (m, 12H, 4×CH₃), 0.86–0.73 (m, 6H, 2×CH₃). ³¹P NMR (202 MHz) DMSO δ (ppm) 148.3, 17.3, 16.7, 10.3, 3.7. TLC Rf 0.71 (9:1 dichloromethane/methanol).

EXAMPLE 5

Synthesis of 4,4'-dimethoxytrityl-trans-9,10-ethanoanthracene-11,12-dimethanol-(N,N-diisopropylamino-2-cyanoethyl)-phosphoramidite trans-9,10-Ethanoanthracene-11,12-dimethanol (2 g, 7.5 mmol) in dry pyridine (30 mL) was treated with DMT chloride (2.5 g, 7.4 mmol), triethylamine (0.9 g, 8.9 mmol), and dimethylaminopyridine (45 mg, 0.4 mmol) and stirred at room temperature for 1 hour. The mixture was poured into 5% aqueous sodium bicarbonate (200 mL). The mixture was extracted with dichloromethane (4×50 mL) and the combined organic layers were washed with saturated aqueous sodium chloride (2×50 mL) and dried over anhydrous sodium sulfate. The solid was filtered off and the filtrate was evaporated to dryness and coevaporated with toluene to give crude product (4.9 g) which was purified by column chromatography on silica gel (200 g) eluting with a gradient of dichloromethane/methanol (0 to 3%). The purities of the fractions were monitored by TLC and fractions containing pure material were combined and evaporated to dryness to give 4,4'-dimethoxytrityl-trans-9,10-ethanoanthracene-11,12-dimethanol (2.4 g) as foam having the following structure:

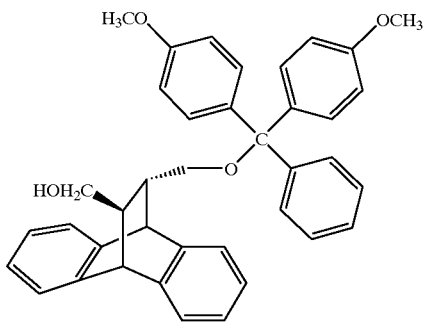

¹H NMR (500 MHz) DMSO δ (ppm) 7.36–6.82 (m, 21H, aromatic), 4.59 (d, 1H, J=5.3, OH), 4.40 (d, 1H, J=2.1 Hz, H-9 or 10), 4.26 (d, 1H, J=2.0 Hz, H-10 or 9), 3.713 & 3.707 (s, 6H, 2×OCH₃), 3.01 (m, 1H), 2.83 (m, 1H), 2.68 (m, 1H), 2.29 (m, 1H), 1.39 (m, 1H), 1.16 (m, 1H), 0.92 (m, 1H). TLC Rf 0.5 (99:11 dichloromethane/methanol).

This DMT derivative (2.3 g, 4 mmol) was dissolved in dry dichloromethane (15 mL) under nitrogen and treated with diisopropylethylamine (2.1 g, 16 mmol), and 2-cyanoethoxy-(N,N-diisopropylamino)chlorophosphine (1.3 g, 5.6 mmol). After stirring for 1 hour, dry methanol (0.5 mL) was added and the mixture evaporated to dryness. The resulting oil was dissolved in 5% aqueous sodium bicarbonate (300 mL), extracted with ethyl acetate (300 mL, then 100 mL). The organic layers were washed with saturated aqueous sodium chloride (300 mL), dried over anhydrous sodium sulfate, and concentrated to give the crude product as an oil. This was purified by NP-HPLC eluting with a gradient of dichloromethane/hexane (80 to 0%). The purities of the fractions were monitored by TLC and fractions containing pure material were combined and evaporated to dryness to give 4,4'-dimethoxytrityl-trans-9,10-ethanoanthracene-11, 12-dimethanol-(N,N-diisopropylamino-2-cyanoethyl)-phosphoramidite (2 g) as a colorless foam having the following structure:

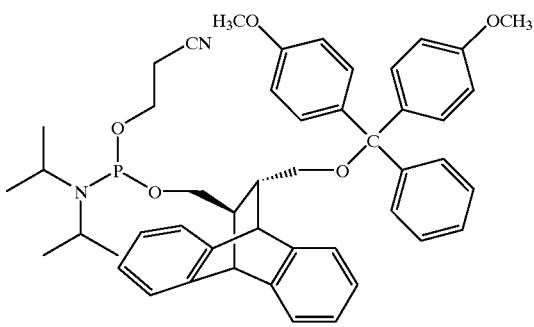

¹H NMR (500 MHz) DMSO δ (ppm) 7.36–6.80 (m, 21H, aromatic), 4.41–4.25 (m, 2H, H-9, 10), 3.71 & 3.70 (s, 6H, 2×OCH₃), 3.69–3.63 (m, 2H) 3.56–3.48 (m, 3H), 3.27–3.25 (m, 1H), 3.18–3.16 (m, 1H), 2.85–2.80 (m, 2H), 2.76–2.68 (m, 3H), 2.39 (m, 1H), 1.42 (m, 1H), 1.36 (m, 2H), 1.22–0.98 (m, 12H, 4×CH₃). ³¹P NMR (202 MHz) DMSO δ (ppm) 147.1, 146.7.

EXAMPLE 6

Synthesis of 1-(4,4'-dimethoxytrityl)-3-(N-benzyl-N-methylamino)-1,2-propanediol-2-(N,N-diisopropylamino-2-cyanoethyl)-phosphoramidite 3-(N-Benzyl-N-methylamino)-1,2-propanediol (5 g, 26 mmol) in dry pyridine (50 mL) was treated with DMT chloride (10.4 g, 31 mmol), triethylamine (3.6 g, 36 mmol), and dimethylaminopyridine (160 mg, 1.3 mmol) and stirred at room temperature for 2 hours. The mixture was poured into 5% aqueous sodium bicarbonate (300 mL). The layers were separated, the aqueous layer was extracted with dichloromethane (3×200 mL), the combined organic layers were washed with saturated aqueous sodium chloride (300 mL), and dried over anhydrous sodium sulfate. The solid was filtered off, the filtrate was evaporated to dryness, and coevaporated with toluene and dichloromethane to give crude product (14 g) which was purified by column chromatography on silica gel (300 g) eluting with a gradient of dichloromethane/methanol (0 to 4%). The purities of the fractions were monitored by TLC and fractions containing pure material were combined and evaporated to dryness to give 1-(4,4'-dimethoxytrityl)-3-(N-benzyl-N-methyl)-1,2-propanediol (12.1 g) as a brown oil having the following structure:

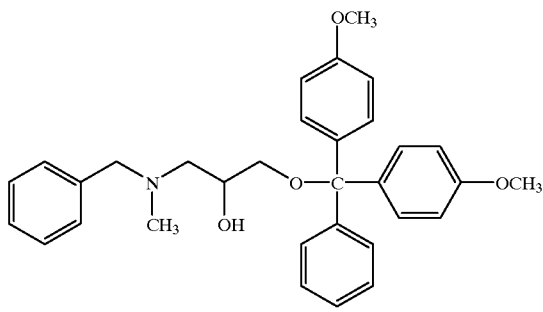

¹H NMR (500 MHz) DMSO δ (ppm) 7.40–6.85 (m, 18H, aromatic), 4.64 (d, 1H, J=4.8 Hz, OH), 3.81 (q, 1H, J=5.3 Hz, CH—O), 3.71 & 3.70 (s, 6H, OCH₃, 2 diastereomers), 3.72 (s, 6H, OCH₃), 3.46 (AB quartet, 1H, J$_{AB}$=13.3 Hz, benzylic H), 3.38 (AB quartet, 1H, J$_{AB}$=13.3 Hz, benzylic H), 2.94 (m, 2H, CH₂—N), 2.36 (m, 2H, CH₂—O), 2.08 (s, 3H, N—CH₃). TLC Rf 0.6 (9:1 dichloromethane/methanol).

This DMT derivative (2.4 g, 4.8 mmol) was dissolved in dry acetonitrile (5 mL) under nitrogen and treated with diisopropylamine (0.73 g, 7.2 mmol), tetrazole (340 mg, 4.8 mmol), and 2-cyanoethoxy-(N,N,N,N-tetraisopropylamino) phosphine (3.63 g, 12.5 mmol). After stirring for 16 hours at room temperature, the mixture was evaporated to dryness, dissolved in ethyl acetate (200 mL) and washed with 5% aqueous sodium bicarbonate (200 mL). The layers were separated and the organic layer was washed with saturated aqueous sodium chloride (200 mL) and dried over anhydrous sodium sulfate. The solid was filtered off and the mixture evaporated to dryness to give the crude product (5.4 g) as a yellow oil which was purified by NP-HPLC eluting with a gradient of dichloromethane/hexane (20 to 0%). The purities of the fractions were monitored by TLC and fractions containing pure material were combined and evaporated to dryness to give 1-(4,4'-dimethoxytrityl)-3-(N-benzyl-N-methylamino)-1,2-propanediol-2-(N,N-diisopropylamino-2-cyanoethyl)-phosphoramidite (3.3 g) as an oil having the following structure:

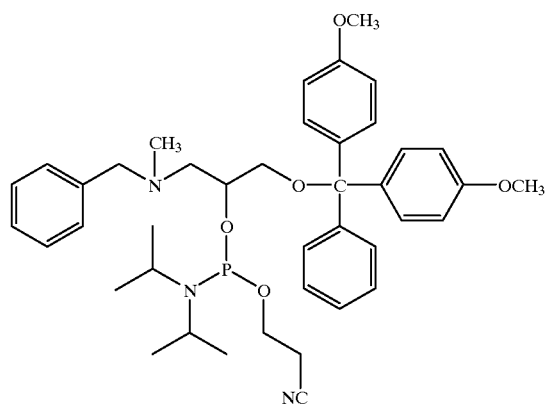

¹H NMR (500 MHz) DMSO δ (ppm) 7.42–6.77 (m, 18H, aromatic), 4.08–3.06, (m, 11H), 3.73 (s, 6H, 2×OCH₃), 2.78–2.42 (m, 4H, 2×CH₂), 1.25–1.06 (m, 12H, 4×CH₃), 0.86–0.73 (m, 6H, 2×CH₃). ³¹P NMR (202 MHz) DMSO δ (ppm) 148.6, 148.5, 140.2, 139.5, 124.1 TLC Rf 0.92, 0.82 (9:1 dichloromethane/methanol).

EXAMPLE 7

Synthesis of 2-(4,4'-dimethoxytrityl)-2,6-bis-hydroxymethylpyridine-6-(N,N-diisopropylamino-2-cyanoethyl)-phosphoramidite 2,6-bis-hydroxymethylpyridine (2.1 g, 15 mmol) in dry pyridine (50 mL) was treated with DMT chloride (1 g, 3 mmol), triethylamine (0.37 g, 3.6 mmol), and dimethylaminopyridine (20 mg, 0.15 mmol) and stirred at room temperature for 16 hours. The mixture concentrated by rotary evaporation and poured into 5% aqueous sodium bicarbonate (200 mL), then extracted with dichloromethane (3×200 mL) and the combined organic layers were washed with saturated sodium chloride solution (200 mL) and dried over anhydrous sodium sulfate. The solid was filtered off and the filtrate was evaporated to dryness and coevaporated with toluene and dichloromethane to give crude product which was purified by column chromatography on silica gel (300 g) eluting with a gradient of dichloromethane/methanol (0 to 4%). The purities of the fractions were monitored by TLC and fractions containing pure material were combined and evaporated to dryness to give 2-(4,4'-dimethoxytrityl)-2,6-bis-hydroxymethylpyridine (3.8 g) as an oil having the following structure:

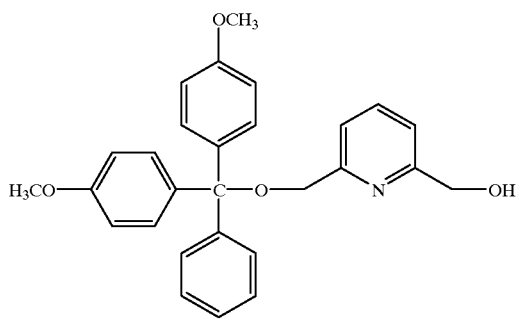

$^1$H NMR (500 MHz) DMSO δ (ppm) 7.87–6.90 (m, 16H, aromatic), 5.29 (s, 1H, OH), 4.44 (s, 2H, CH$_2$), 4.06 (s, 2H, CH$_2$), 3.73 (s, 6H, 2×OCH$_3$). TLC Rf 0.68 (9:1 dichloromethane/methanol).

This DMT derivative (3.3 g, 5.2 mmol) was dissolved in dry acetonitrile (65 mL) under nitrogen and treated with tetrazole (0.33 g, 4.6 mmol), diisopropylamine (0.68 g, 6.7 mmol), and 2-cyanoethoxy-(N,N,N,N-tetraisopropylamino) phosphine (3.3 g, 10.9 mmol). After stirring for 30 minutes, additional diisopropylamine (0.7 g, 6.7 mmol), and 2-cyanoethoxy-(N,N,N,N-tetraisopropylamino)-phosphine (1.8 g, 6.2 mmol) was added and the reaction mixture was stirred for 1 hour. The mixture was poured into 5% aqueous sodium bicarbonate (250 mL), extracted with dichloromethane (2×100 mL, 2×200 mL, 6×50 mL), the organic layers were washed with saturated aqueous sodium chloride (250 mL), dried over anhydrous sodium sulfate, and concentrated to give the crude product (7 g) as an oil. This was purified by NP-HPLC eluting with a gradient of dichloromethane/hexane (10 to 0%). The purities of the fractions were monitored by TLC and fractions containing pure material were combined and evaporated to dryness to give 2-(4,4'-dimethoxytrityl)-2,6-bis-hydroxymethylpyridine-6-(N,N-diisopropylamino-2-cyanoethyl)-phosphoramidite (5.4 g) as a pale yellow oil having the following structure:

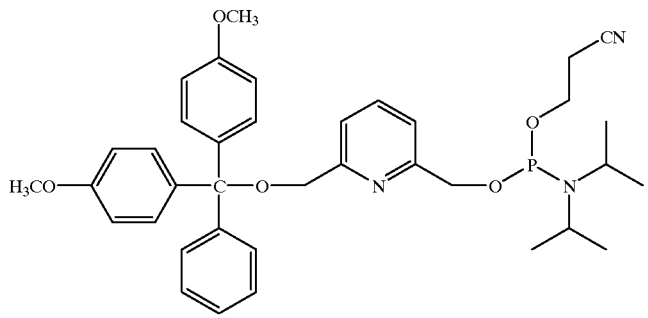

$^1$H NMR (500 MHz) DMSO δ (ppm) 7.91–6.20 (m, 16H, aromatic), 4.64 (m, 2H, CH$_2$-6), 4.09 (s, 2H, CH$_2$-2), 3.73 (s, 6H, 2×OCH$_3$), 3.82–3.46 (m, 6H, CH$_2$ & CH), 1.24–1.10 (m, 12H, 4×CH$_3$). $^{31}$P NMR (202 MHz) DMSO δ (ppm) 148.6, 139.1, 123.6. TLC Rf 0.77, 0.68 (1:1 ethyl acetate/dichloromethane).

EXAMPLE 8

Synthesis of 1-(4,4'-dimethoxytrityl)-2-N-trifluoroacetyl-2-amino-1,3-propanediol-3-(N,N-diisopropylamino-2-cyanoethyl)-phosphoramidite Serinol (1 g, 11 mmol) in dry dichloromethane (10 mL) and dry pyridine (2.7 mL) was cooled to −78° C. on a dry ice/acetone bath and treated with trifluoroacetic anhydride for 1 hour. The reaction mixture was evaporated to dryness and coevaporated with toluene, methanol, hexane, and dichloromethane to give crude 2-N-trifluoroacetamido-serinol (4.2 g) as an oil with the following structure:

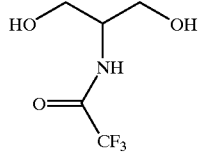

An analytical sample (100 mg) was purified by column chromatography on neutral alumina eluting with isocratic methanol.

$^1$H NMR (500 MHz) DMSO δ (ppm) 4.69 (t, 2H, J=5.7 Hz, OH), 3.80 (m, 1H, CH), 3.46 (m, 2H, 2×CH$_2$) 3.17 (d, 1H, J=5.2 Hz, NH). TLC Rf 0.44 (7:3 dichloromethane/methanol) visualized with ninhydrin spray.

This material (10.3 g, 55 mmol) in dry pyridine (200 mL) was treated with DMT chloride (16.7 g, 49 mmol), triethylamine (7.8 g, 77 mmol), and dimethylaminopyridine (335 mg, 2.7 mmol). Additional DMT chloride (3.35, 9.9 mmol), triethylamine (1.8 g, 18 mmol), and dimethylaminopyridine (70 mg, 0.6 mmol) was added after 18 hours and at 26 hours, and the reaction mixture was stirred at room temperature for a total of 90 hours. The mixture was poured into 5% aqueous sodium bicarbonate (400 mL) and extracted with dichloromethane (500 mL) and the combined organic layers were washed with saturated aqueous sodium chloride (300 mL) and dried over anhydrous sodium sulfate. The solid was filtered off and the filtrate was evaporated to dryness and coevaporated with toluene, methanol, hexane, and dichloromethane to give crude product (25 g) which was purified by column chromatography on silica gel (280 g) eluting with a gradient of dichloromethane/methanol (0 to 3%). The purities of the fractions were monitored by TLC and fractions containing pure material were combined and evaporated to dryness to give 1-(4,4'-dimethoxytrityl)-2-N-trifluoroacetamido-serinol (13.5 g) as an having the following structure:

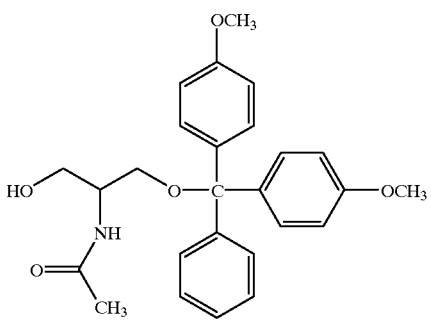

¹H NMR (500 MHz) DMSO δ (ppm) 9.16 (d, 1H, J=8.4 Hz, NH), 7.77–6.82 (m, 13H, aromatic), 4.70 (t, 1H, J=5.5 Hz, OH), 4.08 (m, 1H, CH), 3.73 (s, 6H, 2×OCH₃), 3.14–3.11 (m, 2H, CH₂), 3.01–2.98 (m, 2H, CH₂). TLC Rf 0.37 (99:1 dichloromethane/methanol).

This DMT derivative (4.4 g, 9 mmol) was dissolved in dry dichloromethane (20 mL) under nitrogen and treated with diisopropylethylamine (3.5 g, 27 mmol), and 2-cyanoethoxy-(N,N-diisopropylamino)chlorophosphine (3.2 g, 13.5 mmol). After stirring for 45 minutes the mixture was poured into 5% aqueous sodium bicarbonate (200 mL), and extracted with ethyl acetate (200 mL). The organic layers were washed with saturated aqueous sodium chloride (200 mL) and dried over anhydrous sodium sulfate. The solid was filtered off and the mixture evaporated to dryness to give crude product (7.2 g) which was purified by NP-HPLC using a gradient of dichloromethane/hexane (40 to 0%). The purities of the fractions were monitored by TLC and fractions containing pure material were combined and evaporated to dryness to give 1-(4,4'-dimethoxytrityl)-2-N-trifluoroacetamido-serinol-3-(N,N-diisopropylamino-2-cyanoethyl)-phosphoramidite (5.2 g) as an oil having the following structure:

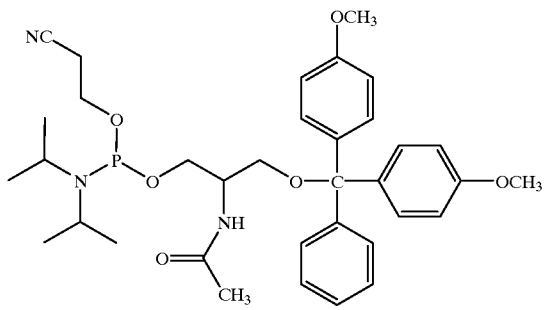

¹H NMR (500 MHz) DMSO δ (ppm) 9.40 (m, 1H, NH), 7.36–6.83 (m, 13H, aromatic), 4.22 (m, 1H, CH), 3.72 (s, 6H, 2×OCH₃), 3.67–2.62 (m, 10H, 4×CH₂, 2×CH), 1.24–0.85 (m, 12H, 4×CH₃), 0.86–0.73 (m, 6H, 2×CH₃). ³¹P NMR (202 MHz) DMSO δ (ppm) 150.3. TLC Rf 0.71 (9:1 trichloroethane/ethyl acetate).

EXAMPLE 9

Synthesis of 7-(4,4'-dimethoxytrityl)-trans-7,8-dihydroxy-dimethyl-exo-tricyclononene[4.2.1.0$^{2,5}$]nona-3-ene-3,4-dicarboxylate-8-(N,N-diisopropylamino-2-cyanoethyl)-phosphoramidite Dimethyl-exo-tricyclo[4.2.1.0$^{2,5}$]-3,7-diene-3,4-dicarboxylate (1 g, 4.3 mmol) was added dropwise to a mixture of 88% formic acid (2.6 mL, 59 mmol) and 30% hydrogen peroxide (0.6 mL, 6 mmol) that had been cooled on an ice bath. The ice bath was removed and the mixture was stirred for 18 hours. The mixture was evaporated to dryness, coevaporated with methanol, toluene, methanol, and dichloromethane. This residue was dissolved in methanol (10 mL), Amberlite® IR-120 strongly acidic ion-exchange resin (1 g) was added, and the mixture was refluxed for 2 hours. The solid was filtered off and the filtrate evaporated to give crude trans-dimethyl-exo-tricyclo[4.2.1.0$^{2,5}$]-3-ene-7,8-diol-3,4-dicarboxylate (1.4 g) as a brown oil having the following structure:

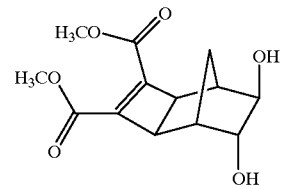

¹H NMR (500 MHz) DMSO δ (ppm) 5.06 (d, 1H, J=5.6 Hz, OH), 4.39 (d, 1H, J=7.0 Hz, OH), 3.93 (m, 1H, CHO), 3.714 (s, 3H, OCH₃), 3.710 (s, 3H, OCH₃), 3.65 (m, 1H, CHO), 3.02 (m, 1H, CH-1 or 6), 2.92 (m, 1H, CH-6 or 1), 2.37 (m, 1H, CH-2 or 5), 2.21 (m, 1H, CH-5 or 2), 1.65 (m, 2H, CH₂).

This material (1.4 g, 4.3 mmol) in dry pyridine (20 mL) was treated with DMT chloride (1.3 g, 3.9 mmol), triethylamine (290 mg, 5.2 mmol), and dimethylamino-pyridine (2 mg, 0.02 mmol) and stirred at room temperature for 4 hours. The mixture was poured into 5% aqueous sodium bicarbonate (100 mL). The layers were separated and the aqueous layer was extracted with dichloromethane (6×30 mL) and the combined organic layers were washed with saturated aqueous sodium chloride (2×30 mL) and dried over anhydrous sodium sulfate. The solid was filtered off and the filtrate was evaporated to dryness and coevaporated with toluene, methanol, and dichloromethane to give crude product (2.4 g) which was purified by column chromatography on silica gel (100 g) eluting with a gradient of dichloromethane/methanol (0 to 1%). The purities of the fractions were monitored by TLC and fractions containing pure material were combined and evaporated to dryness to give 7-(4,4'-dimethoxytrityl)-trans-7,8-dihydroxy-dimethyl-exo-tricyclononene[4.2.1.0$^{2,5}$]nona-3-ene-3,4-dicarboxylate (1.2 g) as a yellow foam having the following structure:

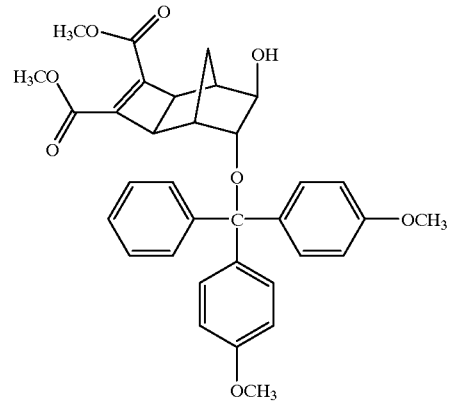

¹H NMR (500 MHz) DMSO δ (ppm) 7.36–6.82 (m, 13H, aromatic), 4.65 (d, 1H, J=5.0 Hz, OH), 3.76 (m, 1H, OCH), 3.724 & 3.721 (s, 6H, 2×OCH₃, 2 diastereomers), 3.63 (s, 3H, OCH₃), 3.47 (m, 1H, OCH), 3.38 (s, 3H, OCH₃), 2.90 (m, 1H, CH-1 or 6) 2.77 (m, 1H, CH-6 or 1), 2.09 (m, 1H, CH-2 or 5), 2.02 (m, 1H, CH-5 or 2), 1.44 (m, 1H, CH₂), 0.82 (m, 1H, CH₂). TLC Rf 0.28 (dichloromethane).

This DMT derivative (1.2 g, 2.1 mmol) was dissolved in dry acetonitrile (20 mL) under nitrogen and treated with tetrazole (150 mg, 2.1 mmol), diisopropylamine (0.32 g, 3.15 mmol), and 2-cyanoethoxy-(N,N,N,N-tetraisopropylamino)phosphine (1.6 g, 5.3 mmol). After stirring for 21 hours the mixture was evaporated to dryness, dissolved in 5% aqueous sodium bicarbonate (125 mL), and extracted with dichloromethane (2×100 mL). The organic layers were washed with water (125 mL) and dried over anhydrous sodium sulfate. The solid was filtered off and the mixture evaporated to dryness to give crude product (2.6 g) which was purified by NP-HPLC eluting with a gradient of dichloromethane/hexane (60 to 0%). The purities of the fractions were monitored by TLC and fractions containing pure material were combined and evaporated to dryness to give 7-(4,4'-dimethoxytrityl)-trans-7,8-dihydroxy-dimethyl-exo-tricyclo[4.2.1.0²,⁵]nona-3-ene-3,4-dicarboxylate-8-(N,N-diisopropylamino-2-cyanoethyl)-phosphoramidite (1.4 g) as a colorless foam having the following structure:

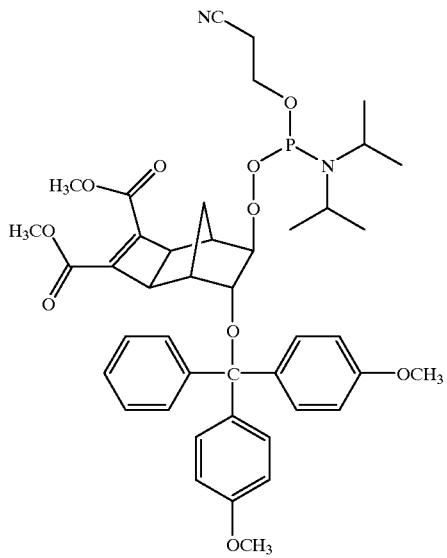

¹H NMR (500 MHz) DMSO δ (ppm) 7.38–6.80 (m, 13H, aromatic), 3.92 (m, 1H, OCH), 3.82 (m, 1H, OCH), 3.72 & 3.71 (s, 6H, 2×OCH₃ for 2 diastereomers), 3.630 & 3.629 (s, 3H, OCH₃ for 2 diastereomers), 3.353 & 3.347 (s, 3H, OCH₃ for 2 diastereomers), 2.96 (m, 1H, CH-1 or 6), 2.82 (m, 1H, CH-6 or 1), 2.72 (m, 4H, 2×CH₂), 2.26 (m, 1H, H-2 or 5), 2.18 (m, 1H, CH-5 or 2), 1.39 (m, 1H, CH₂), 1.19–1.05 (m, 12H, 4×CH₃), 0.80 (m, 1H, CH₂). ³¹P NMR (202 MHz) DMSO δ (ppm) 146.8, 146.4, 123.7. TLC Rf 0.56 (99:1 dichloromethane/methanol).

EXAMPLE 10

Synthesis of 1-(4,4'-dimethoxytrityl)-trans-1,2-cyclopentanediol-3-methylacetate-2-(N,N-diisopropylamino-2-cyanoethyl)phosphoramidite 2-Cyclopentene-1-acetic acid (2.35 g, 18.7 mmol) in diethyl ether (5 mL) was cooled on an ice/salt bath and treated with diazomethane (50 mL, 0.46 M) at 0° C. The mixture was concentrated to dryness to give 2-cyclopentene-1-methylacetate (3.1 g) as a colorless oil with the following structure:

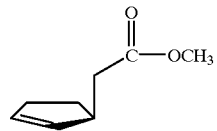

¹H NMR (500 MHz) DMSO δ (ppm) 5.74 (m, 1H, vinylic CH), 5.65 (m, 1H, vinylic CH), 3.58 (s, 3H, OCH₃), 2.95 (m, 1H, CH), 2.39–2.18 (m, 4H, CH₂), 1.98 (m, 1H, CH₂), 1.38 (m, 1H, CH₂), 1.65 (m, 2H, CH₂). TLC Rf 0.89 (9:1 dichloromethane/methanol), visualized with ammonium molybdate/sulfuric acid.

This material (1.5 g) was added dropwise to a mixture of 96% formic acid (5.6 mL, 150 mmol) and 30% hydrogen peroxide (0.5 mL, 15 mmol) that had been cooled on an ice/salt bath. The ice bath was removed and the mixture was stirred for 16 hours. The mixture was evaporated to dryness, co-evaporated with toluene, methanol, and hexane. This residue was dissolved in methanol (30 mL), Amberlite® IR-120 strongly acidic ion-exchange resin (3 g) was added, and the mixture was refluxed for 2 hours. The solid was filtered off and the filtrate evaporated to give crude trans-1,2-cyclopentanediol-3-methylacetate (1 g) as an oil having the following structure:

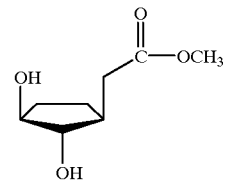

¹H NMR (500 MHz) DMSO δ (ppm) 4.90 (br s, 2H, OH), 4.57 (m, 1H), 4.04 (m, 1H), 3.57 (s, 3H, OCH₃), 2.91 (m, 1H), 2.78 (m, 1H) 2.22 (m, 1H), 2.03 (m, 1H, CH₂), 1.68 (m, 1H, CH₂), 1.53 (m, 1H, CH₂), 1.42 (m, 1H, CH₂).

This material (1 g, 6 mmol) in dry pyridine (20 mL) was treated with DMT chloride (2.4 g, 7.2 mmol), triethylamine (0.85 g, 8.4 mmol), and dimethylaminopyridine (37 mg, 0.3 mmol) and stirred at room temperature for 4 hours. The mixture was concentrated by rotary evaporation, dissolved in dichloromethane (200 mL) and poured into 5% aqueous sodium bicarbonate (200 mL). The layers were separated and the aqueous layer was extracted with dichloromethane (2×200 mL) and the combined organic layers were washed with saturated aqueous sodium chloride (250 mL) and dried over anhydrous sodium sulfate. The solid was filtered off and the filtrate was evaporated to dryness and coevaporated with toluene, methanol, hexane, and dichloromethane to give crude product (3.3 g) which was purified by column chromatography on silica gel (150 g) eluting with a gradient of dichloromethane/methanol (0 to 2%). The purities of the fractions were monitored by TLC and fractions containing the desired material (520 mg) were combined, evaporated to dryness and repurified by NP-HPLC eluting with isocratic dichloromethane. The purities of the fractions were monitored by TLC and fractions containing the pure material were combined and evaporated to dryness to give 1-(4,4'- dimethoxytrityl)-trans-1,2-cyclopentanediol-3-methyl acetate (260 mg) as a pale yellow oil having the following structure:

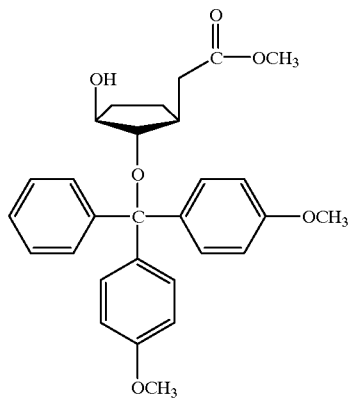

$^1$H NMR (500 MHz) DMSO δ (ppm) 7.47–6.83 (m, 13H, aromatic), 4.65 (d, 1H, J=5.5 Hz, OH), 3.73 (s, 6H, 2×OCH$_3$), 3.58 (m, 2H), 3.55 (s, 3H, OCH$_3$), 3.49 (m, 2H), 2.54 (m, 2H) 2.20 (m, 2H), 1.81 (m, 2H), 1.50 (m, 2H), 1.14 (m, 2H), 0.87 (m, 2H), 0.77 (m, 2H). TLC Rf 0.32 (9:1 trichloroethane/ethylacetate).

This DMT derivative (260 mg, 0.6 mmol) was dissolved in dry dichloromethane (5 mL) under nitrogen and treated with diisopropylethylamine (0.23 g, 1.8 mmol), and 2-cyanoethoxy-(N,N-diisopropylamino)chlorophosphine (0.21 g, 0.9 mmol). After stirring for 15 minutes the mixture was evaporated to dryness, dissolved in ethylacetate (75 mL), washed with 5% aqueous sodium bicarbonate (100 mL). The aqueous layer was extracted with ethylacetate (2×75 mL). The organic layers were washed with saturated aqueous sodium chloride (100 mL) and dried over anhydrous sodium sulfate. The solid was filtered off and the mixture evaporated to dryness to give crude product (540 mg) which was purified by NP-HPLC eluting with isocratic dichloromethane/hexane (6:4). The purities of the fractions were monitored by TLC and fractions containing pure material were combined and evaporated to dryness to give 1-(4,4'-dimethoxytrityl)-trans-1,2-cyclopentanediol-3-methyl acetate-2-(N,N-diisopropylamino-2-cyanoethyl)-phosphoramidite (105 mg/fast diastereomer & 144 mg/slow diastereomer) as a colorless oil having the following structure:

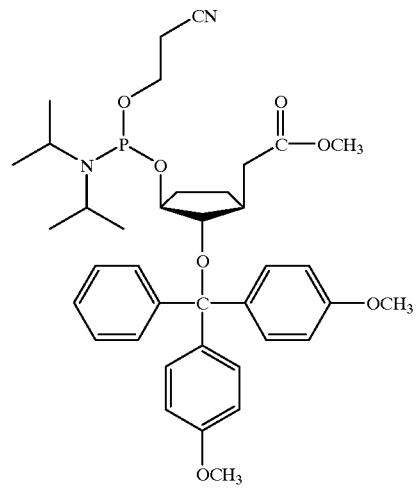

$^1$H NMR (500 MHz) DMSO fast δ (ppm) 7.43–6.86 (m, 13H, aromatic), 3.84 (m, 2H), 3.76 (m, 1H), 3.75 (m, 1H), 3.73 (s, 6H, 2×OCH$_3$), 3.57 (s, 3H, OCH$_3$), 3.56–3.45 (m, 5H), 2.63–2.62 (m, 1H), 2.61–2.58 (m, 2H), 2.56–2.53 (m, 1H), 2.39 (d, 1H, J=9.5 Hz), 2.38 (d, 1H, J=9.5 Hz), 2.14 (m, 2H), 1.69 (m, 3H), 1.32 (m, 3H, CH$_2$), 1.23 (m, 3H), 1.11 (d, 6H, J=6.8 Hz, 2×CH$_3$), 1.06 (d, 6H, J=6.8 Hz, 2×CH$_3$). $^{31}$P NMR (202 MHz) DMSO δ (ppm) 148.8 fast.

$^1$H NMR (500 MHz) DMSO slow δ (ppm) 7.43–6.84 (m, 13H, aromatic), 3.83–3.75 (m, 3H), 3.72 (s, 6H, 2×OCH$_3$), 3.65–3.59 (m, 2H), 3.57 (s, 3H, OCH$_3$), 3.56–3.45 (m, 4H), 2.72 (m, 2H), 2.69 (m, 1H), 2.64–2.52 (m, 3H), 2.41–2.34 (m, 2H), 2.15 (m, 2H), 1.66 (m, 3H), 1.24 (m, 5H), 1.14–0.98 (m, 12H, 4×CH$_3$). $^{31}$P NMR (202 MHz) DMSO δ (ppm) 148.3. TLC Rf 0.61 (9:1 trichloroethane/ethylacetate).

EXAMPLE 11

Synthesis of 2-(4,4'-dimethoxytrityl)-hydroxymethylphenol-1-(N,N-diisopropylamino-2-cyanoethyl)-phosphoramidite 2-Hydroxybenzyl alcohol (5 g, 40.3 mmol) in dry pyridine (100 mL) was treated with DMT chloride (16.4 g, 48.3 mmol), triethylamine (5.5 g, 54.5 mmol), and dimethylaminopyridine (244 mg, 2 mmol) and stirred at room temperature for 19 hours. The mixture was poured into 5% aqueous sodium bicarbonate (500 mL), extracted with dichloromethane (4×100 mL). The combined organic layers were washed with saturated aqueous sodium chloride (100 mL) and dried over anhydrous sodium sulfate. The solid was filtered off and the filtrate was evaporated to dryness to give the crude product (20 g) which was purified by column chromatography on silica gel (300 g) eluting with a gradient or 1,1,1-trichloroethane/ethyl acetate (0 to 2%). The purities of the fractions were monitored by TLC and fractions containing the desired material were combined and evaporated to dryness to give 2-(4,4'-dimethoxytrityl)-hydroxymethylphenol (25.7 g) as a pale yellow oil having the following structure:

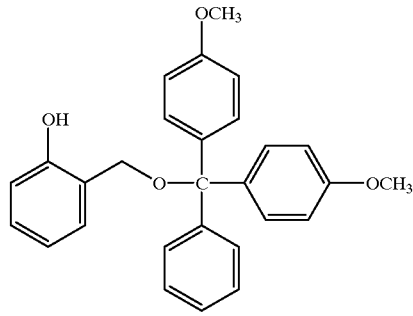

$^1$H NMR (500 MHz) DMSO δ (ppm) 9.39 (s, 1H, phenolic OH), 7.59–6.72 (m, 17H, aromatic), 4.01 (s, 2H, benzylic CH$_2$), 3.72 (s, 6H, 2×OCH$_3$), 3.68 (s, 3H, OCH$_3$). TLC Rf 0.68 (1,1,1-trichloroethane).

This DMT derivative (4 g, 10.5 mmol) was dissolved in dry dichloromethane (25 mL) under nitrogen and treated with diisopropylethylamine (6.7 g, 52 mmol), and 2-cyanoethoxy-(N,N-diisopropylamino)chlorophosphine (3.2 g, 13.5 mmol). After stirring for 1 hour, additional 2-cyanoethoxy-(N,N-diisopropylamino)-chlorophosphine (1.1 g, 4.2 mmol) was added and the mixture was stirred for 2 hours. Ethyl acetate (300 mL) and methanol (1 mL) were added and the mixture was washed with 10% aqueous sodium carbonate (2×200 mL), aqueous sodium chloride (2×200 mL), add the organic layers were dried over anhydrous sodium sulfate. The solid was filtered off and the filtrate was evaporated to dryness and coevaporated with toluene to give the crude product. This was purified column chromatography on silica gel (200 g) eluting with dichloromethane. The purities of the fractions were monitored by TLC and fractions containing pure material were combined and evaporated to dryness to give 2-(4,4'-dimethoxytrityl)-hydroxymethylphenol-1-(N,N-diisopropylamino-2-cyanoethyl)-phosphoramidite (4.2 g, 6.8 mmol) as an oil having the following structure:

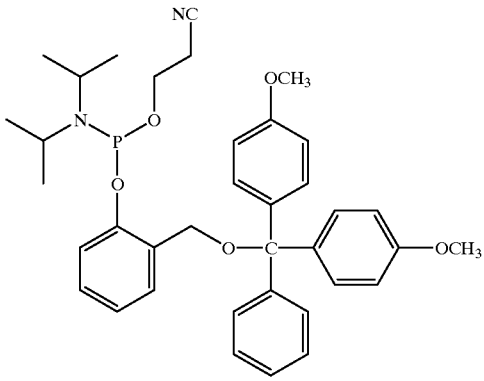

$^1$H NMR (500 MHz) DMSO δ (ppm) 7.75–6.75 (m, 17H, aromatic), 4.10 (m, 2H), 4.01 (s, 1H, benzylic CH$_2$), 3.72 (s, 6H, OCH$_3$), 3.71–3.60 (m, 2H), 3.49 (m, 2H), 2.69 (m, 2H), 1.09 (d, 6H, J=6.7 Hz, 2×CH$_3$), 0.90 (d, 6H, J=6.7 Hz, 2×CH$_3$). $^{31}$P NMR (202 MHz) DMSO δ (ppm) 145.2. TLC Rf 0.57, 0.49 (99:1 CH$_2$Cl$_2$/MeOH).

EXAMPLE 12

O$^1$-(2-Cyanoethyl-N,N-Diisopropyl-phosphoramidite)-O$^2$-(4,4'-Dimethoxytrityl)-2-Hydroxyethanol 2-Cyanoethyl-N,N-Diisopropylchlorophosphoramidite (0.68 mL, 0.04 mmol) was added dropwise to a stirred solution of O$^2$-(4,4'-dimethoxytrityl)-2-hydroxyethanol (1.3 g, 2.76 mmol) in anhydrous THF (15 mL) containing triethylamine (0.84 mL, 6.1 mmol). On addition, the mixture was stirred at RT for 30 min, and then filtered through a sintered glass funnel under nitrogen. The filtrate was evaporated under vacuum, and the residue dissolved in anhyrous benzene and then filtered. The filtrate was evaporated in vacuo, and the residue dissolved in an ethyl acetate-hexane mixture (3:7) and applied to a flash column. The product was eluted using 30% ethyl acetate in hexane containing 1% triethylamine, and homogenous fractions were combined and evaporated to give the product as an almost colorless oil, (1.53 g, 82%) having the following structure:

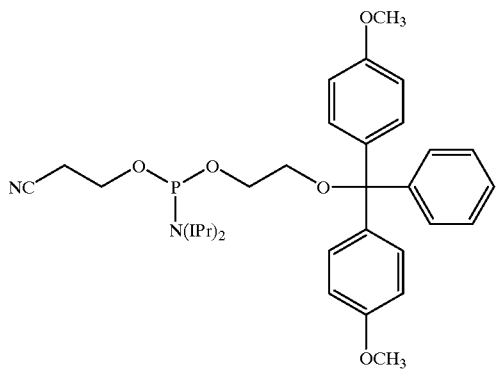

$^{31}$P NMR δ 145. $^1$H NMR δ 7.50–6.80(13H, m aromatic), 3.70(6H, s, OCH$_3$), 3.85–3.60(4H, m, CH$_2$ODMT+CH$_2$OP+ CH$_2$CH$_2$CN), 3.16(1H, m, CH$_2$CN), 3.06(1H, m, CH$_2$CN), 2.74(2H, m, CH(CH$_3$)$_2$), 1.13(12H, m, CH$_3$). Rf=0.35 30% Ethyl acetate in hexane.

EXAMPLE 13

O$^1$-(2-Cyanoethyl-N,N-Diisopropyl-phosphoramidite)-O$^2$-(4,4'-Dimethoxytrityl)-1,2-Dihydroxycyclopentane Dimethoxytrityl chloride (3.38 g, 10 mmol) was added in portions to a stirred solution of the cyclopentanol (5 g, 49 mmol) in anhydrous pyridine (300 mL) containing DMAP (20 mg). On addition, the mixture was left to stir at RT overnight after which the pyridine was removed under vacuum, and the residue adsorbed onto silica gel. This mixture was then applied to a flash silica gel column and the product eluted using 25% ethyl acetate in hexane. Homogenous fractions were combined and evaporated in vacuo, to give (±)-O$^2$-4,4'-dimethoxytrityl-1,2-dihydroxycyclopentane as a yellow solid. Rf=0.29 (25% Ethyl acetate in hexane).

2-Cyanoethyl-N,N-Diisopropylchlorophosphoramidite (1.4 mL, 6.24 mmol) was added dropwise to a stirred solution of the above DMT derivative (2.29 g, 5.67 mmol) in anhydrous THF (20 mL) containing triethylamine (1.56 mL, 11.34 mmol). On addition, the mixture was stirred at RT for 60 min, and then filtered through a scintered glass funnel under nitrogen. The filtrate was evaporated under vacuum, and the residue dissolved in anhydrous benzene and then filtered. The filtrate was evaporated in vacuo, and the residue dissolved in an ethyl acetate/hexane mixture (3:7) and applied to a flash column. The product was then eluted using 30% ethyl acetate in hexane containing 1% triethylamine, and homogenous fractions were combined and evaporated to give the product as an almost colorless oil, (1.84 g, 57%) having the following structure:

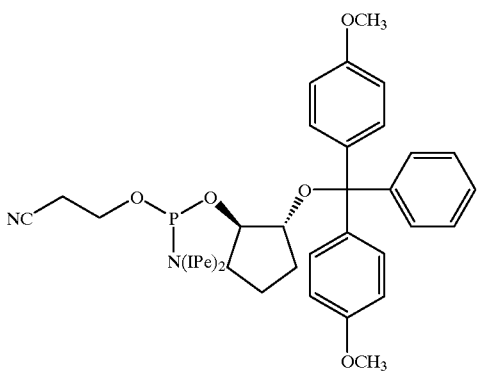

$^{31}$P NMR δ 147. $^1$H NMR δ 7.50–6.80(13H, m, aromatic), 3.93(1H, m, C_HOP), 3.82(1H, m, C_HODMT), 3.72(6H, m, OCH$_3$), 3.58(2H, m, C_H$_2$OP), 3.49(2H, m, C_H$_2$CN), 2.72 (1H, m, NC_H), 2.66(1H, m, NC_H), 1.88(1H, m, alicyclic), 1.52(1H, m, alicyclic), 1.41(1H, m, alicyclic), 1.21(1H, m, alicyclic), 1.06(12H, m, CH(C_H$_3$)$_2$), 0.92(1H, m, alicyclic), 0.82(1H, m, alicyclic). Rf=0.47 (30% Ethyl acetate in hexane).

EXAMPLE 14

O$^1$-(2-Cyanoethyl-N,N-Diisopropylphosphoramidite)-O$^2$-(4,4'-Dimethoxytrityl)-1,2-Dihydroxycyclo-octane Dimethoxytrityl chloride (3.76 g, 11.1 mmol) was added to a stirred solution of cis-1,2-dihydroxycyclooctane (8 g, 55.5 mmol) in anhydrous pyridine (300 mL) containing DMAP (20 mg). The reaction was left to stir at RT under nitrogen overnight. The reaction mixture was then evaporated under vacuum, and the residue adsorbed onto silica gel and applied to a silica gel flash column. The product was eluted using 30% ethyl acetate in hexane, and homogenous fractions combined and evaporated to give O$^2$-(4,4'-dimethoxytrityl)-cis-1,2-dihydroxycyclooctane as an almost colorless oil, (3.30 g, 67%).

$^1$H NMR δ 7.50–6.80 (13H, m, aromatic), 4.22 (1H, m, OH), 3.72 (6H, m, OCH$_3$), 3.46 (2H, m, CHOH+ CHODMT), 1.60–0.90 (12H, m, alicyclic). Rf=0.38 (30% Ethyl acetate in hexane).

2-Cyanoethyl-N,N-Diisopropylchlorophosphoramidite (0.54 mL, 2.4 mmol) was added dropwise to a stirred solution of the above DMT derivative (0.97 g, 2.18 mmol) in anhydrous THF (20 mL) containing triethylamine (0.63 mL, 4.59 mmol). On addition, the mixture was stirred at RT for 60 min, and then filtered through a sintered glass funnel under nitrogen. The filtrate was evaporated under vacuum, and the residue dissolved in anhyrous benzene and then filtered. The filtrate was evaporated in vacuo, and the residue dissolved in an ethyl acetate/hexane mixture (3:7) and applied to a flash column. The product was then eluted using 25% ethyl acetate in hexane containing 1% triethylamine, and homogenous fractions were combined and evaporated to give the title compound as an almost colorless oil, (1.07 g, 80%) with the following structure:

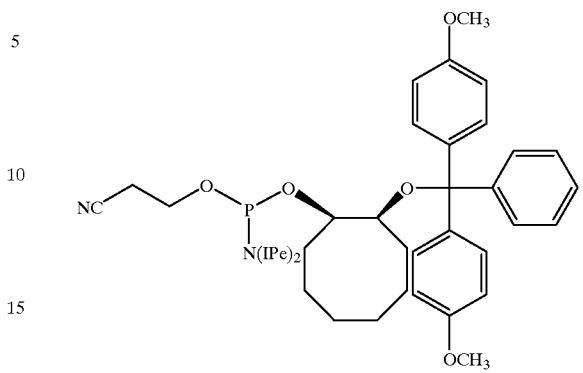

$^{31}$P NMR δ 145. $^1$H NMR δ 7.50–6.80 (13H, m, aromatic), 3.72 (6H, s, OCH$_3$), 3.63 (2H, m, CH$_2$OP), 3.48 (2H, m, CH$_2$CN), 2.68 (2H, m, NCH), 1.70–1.20 (12H, m, alicyclic), 1.10 (6H, m, CH(CH$_3$)$_2$), 1.00 (6H, m, CH(CH$_3$)$_2$). Rf=0.27 (25% Ethyl acetate in hexane).

EXAMPLE 15

O$^2$-(2-Cyanoethyl-N,N-Diisopropylphosphoramidite)-O$^3$-(4,4'-Dimethoxytrityl)-7-(2,3-Dihydroxypropyl) theophylline Dimethoxytrityl chloride (22.7 g, 67 mmol) was added in portions to a stirred solution of 7-(2,3-Dihydroxypropyl) theophylline (10 g, 61 mmol) in anhydrous pyridine (200 mL) containing DMAP (20 mg). The reaction was left to stir at RT under nitrogen overnight. The reaction mixture was then evaporated under vacuum, and the residue adsorbed onto silica gel and applied to a silica gel flash column. The product was eluted using 3% methanol in dichloromethane, and homogenous fractions combined and evaporated to give 7-(O$^3$-(4,4'-dimethoxytrityl)-2,3-dihydroxypropyl) theophylline as an almost colorless oil (14.4 g, 51%).

$^1$H NMR δ 7.91(1H, s, H8), 7.50–6.80(13H, m, aromatic), 5.28(1H, d, CH_OH), 4.47(1H, d of d, NC_H$_2$), 4.16(1H, d of d, NC_H$_2$), 4.04(1H, m, C_HOH), 3.72(6H, s, OC_H$_3$), 3.40 (3H, s, NCH$_3$), 3.22(3H, s, NCH$_3$), 3.00(1H, m, C_H$_2$ODMT), 2.87(1H, m, C_H$_2$ODMT). Rf=0.29 (3% Methanol in dichloromethane).

2-Cyanoethyl-N,N-Diisopropylchlorophosphoramidite (4.6 mL, 20 mmol) was added dropwise to a stirred solution of the above DMT derivative (5.0 g, 9 mmol) in anhydrous THF (40 mL) containing triethylamine (2.7 mL, 19 mmol). On addition, the mixture was stirred at RT for 60 min, and then filtered through a sintered glass funnel under nitrogen. The filtrate was evaporated under vacuum, and the residue dissolved in anhydrous benzene and then filtered. The filtrate was evaporated in vacuo, and the residue dissolved in an ethyl acetate/hexane mixture (3:7) and applied to a flash column. The product was then eluted using 35% ethyl acetate in hexane containing 1% triethylamine, and homogenous fractions were combined and evaporated to give the title compound as a powder, (3.9 g, 57%) with the following structure:

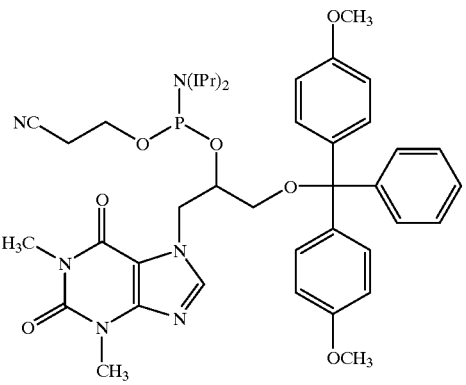
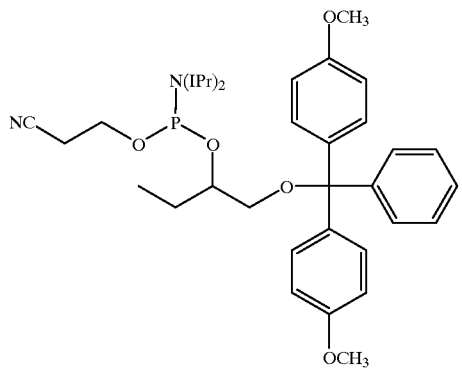

$^{31}$P NMR δ 149. $^1$H NMR δ 7.99 (1H, s, H8), 7.50–6.80 (13H, m, aromatic), 4.50 (2H, m, N$_7$CH$_2$), 4.38 (1H, m, CHOP), 3.72 (6H, s, OCH$_3$), 3.51 (2H, m, OCH$_2$), 3.42 (2H, m, CH$_2$CN), 3.40 (3H, s, NCH$_3$), 3.22 (3H, s, NCH$_3$), 3.18 (1H, m, CH$_2$ODMT), 3.10 (1H, m, CH$_2$ODMT), 2.55 (2H, m, NCH), 1.05 (6H, d, CHCH$_3$), 0.97 (6H, d, CHCH$_3$). Rf=0.34, 0.16 (50% Ethyl acetate in hexane).

EXAMPLE 16

(±)-O$^2$-(2-Cyanoethyl-N,N-Diisopropylphosphoramidite)-O$^1$-(4,4'-Dimethoxytrityl)-1,2-Dihydroxybutane 4,4'-Dimethoxytrityl chloride (10.33 g, 30.5 mmol) was added in portions to a stirred solution of 1,2-butanediol (2.5 g, 27.7 mmol) in anhydrous pyridine (200 mL) containing DMAP (1.7 g). The mixture was stirred at RT under nitrogen overnight. The solution was then evaporated under vacuum, and the residue adsorbed onto silica gel and applied to a silica gel flash column which was eluted using 10% ethyl acetate in hexane. Homogenous fractions were combined and evaporated to give (±)-O$^1$-(4,4'-dimethoxytrityl)-1,2-dihydroxybutane as an almost colorless oil, (8.15 g, 75%).

$^1$H NMR δ 7.50–6.80 (13H, m, aromatic), 4.59 (1H, d, OH), 3.73 (6H, s, OCH$_3$), 3.53 (1H, d of d, CHOH), 2.91 (1H, t, CH$_2$ODMT), 2.78 (1H, t, CH$_2$ODMT), 1.55 (1H, m, CH$_2$CH$_3$), 1.29 (1H, m, CH$_2$CH$_3$), 0.8 (3H, t, CH$_3$). Rf=0.2 (10% Ethyl acetate in hexane).

2-Cyanoethyl-N,N-Diisopropylchlorophosphoramidite (0.94 mL, 4.2 mmol) was added dropwise to a stirred solution of the above DMT derivative (1.5 g, 3.8 mmol) in anhydrous THF (20 mL) containing triethylamine (1.12 mL, 8.4 mmol). On addition, the mixture was stirred at RT for 7 h., and was then filtered through a sintered glass funnel under nitrogen. The filtrate was evaporated under vacuum, and the residue dissolved in anhyrous benzene and then filtered. The filtrate was evaporated in vacuo, and the residue dissolved in an ethyl acetate hexane mixture (3:7) and applied to a flash column. The product was then eluted using 20% ethyl acetate in hexane containing 1% triethylamine, and homogenous fractions were combined and evaporated to give the product as a viscous oil, (1.0 g, 44%) with the following structure:

$^{31}$P NMR δ 148.5. $^1$H NMR δ 7.50–6.80(13H, m, aromatic), 3.82(1H, m, OCH), 3.71(6H, s, OCH$_3$), 3.53(2H, m, CH$_2$CN), 2.97(1H, m, CH$_2$ODMT), 2.80(1H, m, CH$_2$ODMT), 2.60(1H, m, NCH), 1.67(1H, m, CH$_3$CH$_2$), 1.51(1H, m, CH$_3$CH$_2$), 1.12(12H, m, CH(CH$_3$)$_2$), 0.78(3H, m, CH$_2$CH$_3$). Rf=0.16 20% Ethyl acetate in hexane.

EXAMPLE 17

(±)-O$^2$-(2-Cyanoethyl-N,N-Diisopropylphosphoramidite)-O$^1$-(4,4'-Dimethoxytrityl)-3,3-Dimethyl-1,2-Dihydroxybutane 4,4'-Dimethoxytrityl chloride (9.4 g, 27.7 mmol) was added in portions to a stirred solution of freshly distilled 3,3 dimethyl-1,2-dihydroxybutanediol (3 g, 25.4 mmol.) in anhydrous pyridine (200 mL) containing DMAP (0.31 g). The mixture was stirred at RT under nitrogen overnight. The solution was then evaporated under vacuum, and the residue adsorbed onto silica gel and applied to a silica gel short path column. The product was eluted using 2 L of 10% ethyl acetate followed by 1 L of 20% ethyl acetate in hexane, and finally 1 L of 30% ethyl acetate in hexane. Homogenous fractions were combined and evaporated to give (±)-O$^1$-(4, 4'-dimethoxytrityl)-3,3-dimethyl-1,2-dihydro xybutane as an almost colorless oil, (6.03 g, 56.5%).

$^1$H NMR δ 7.50–6.70(13H, m aromatic), 4.70(1H, d, OH), 3.72(6H, s, OCH$_3$), 3.32(1H, t, CHOH), 2.93(2H, m, CH$_2$), 0.72(9H, s, CH$_3$). Rf=0.37 (20% Ethel acetate in hexane).

2-Cyanoethyl-N,N-diisopropylchlorophosphoramidite (1.81 mL, 8.1 mmol) was added dropwise to a stirred solution of the above DMT derivative (2.27 g, 5.4 mmol) in anhydrous THF (50 mL) containing triethylamine (1.6 mL, 11.3 mmol). On addition, the mixture was stirred at RT overnight, and was then filtered through a sintered glass funnel under nitrogen. The filtrate was evaporated under vacuum, and the residue dissolved in anhydrous benzene and then filtered. The filtrate was then evaporated in vacuo, and the residue dissolved in an ethyl acetate/hexane mixture (3:7) and applied to a flash column. The product was eluted using 30% ethyl acetate in hexane containing 1% triethylamine, and homogenous fractions were combined and evaporated to give the title compound as a viscous oil, (1.89 g, 56%) having the following structure:

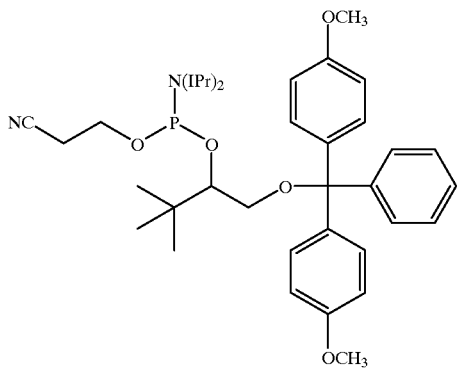

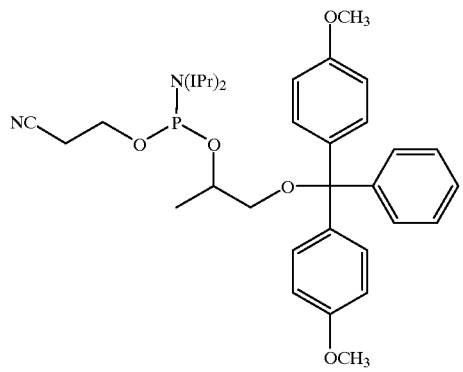

$^{31}$P NMR δ 149. $^1$H NMR δ 7.60–6.80 (13H, m, aromatic), 3.82 (1H, m, C<u>H</u>OP), 3.65 (2H, m, OC<u>H</u>$_2$), 3.63 (2H, m, C<u>H</u>$_2$CN), 3.19 (1H, d of d, C<u>H</u>$_2$ODMT), 3.08 (1H, d of d, C<u>H</u>$_2$ODMT), 2.79 (1H, m, NC<u>H</u>), 2.67 (1H, m, N C<u>H</u>), 1.15 (12H, m, CH(C<u>H</u>$_3$)$_2$), 0.78 (9H, m, (C<u>H</u>$_3$)$_3$). Rf=0.13 (20% Ethyl acetate in hexane).

EXAMPLE 18

(±)-O$^2$-(2-Cyanoethyl-N,N-Diisopropylphosphoramidite)-O$^1$-(4,4'-Dimethoxytrityl)-1,2-Dihydroxypropane 4,4'-Dimethoxytrityl chloride (7.42 g, 21.9 mmol) was added in portions to a stirred solution of 1,2-propanediol (1.52 g, 20.0 mmol) in anhydrous pyridine (200 mL) containing DMAP (0.28 g). The mixture was stirred at RT under nitrogen overnight. The solution was then evaporated under vacuum, and the residue adsorbed onto silica gel and applied to a silica gel flash column. The product was eluted using 20% ethyl acetate in hexane, and homogenous fractions were combined and evaporated to give (±)-O$^1$-(4,4'-dimethoxytrityl)-1,2-dihydroxypropane as an almost colorless oil (3.1 g, 41%).

$^1$H NMR δ s 7.50–6.80 (13H, m, aromatic), 4.6 (1H, d, CHO<u>H</u>), 3.78 (1H, m, C<u>H</u>OH), 3.66 (6H, s, OCH$_3$), 2.91 (1H, t, CH$_2$), 2.68 (1H, t, CH$_2$). Rf=0.25 (20% Ethyl acetate in hexane).

2-Cyanoethyl-N,N-Diisopropylchlorophosphoramidite (1.36 mL, 6.1 mmol) was added dropwise to a stirred solution of the above DMT derivative (2.1 g, 5.6 mmol) in anhydrous THF (50 mL) containing triethylamine (1.63 mL, 11.7 mmol). On addition, the mixture was stirred at RT overnight, and was then filtered through a sintered glass funnel under nitrogen. The filtrate was evaporated under vacuum, and the residue dissolved in anhyrous benzene and then filtered. The filtrate was evaporated in vacuo, and the residue dissolved in an ethyl acetate/hexane mixture (3:7) and applied to a flash column. The product was then eluted using 20% ethyl acetate in hexane containing 1% triethylamine, and homogenous fractions were combined and evaporated to give the title compound as a viscous oil, (1.0 g, 31%) having the following structure:

$^{31}$P NMR δ 147. $^1$H NMR δ 7.50–6.70 (13H, m, aromatic), 4.03 (1H, m, CHOP), 3.72 (6H, s, OCH$_3$), 3.65 (2H, m, OCH$_2$), 3.58 (2H, m, CH$_2$CN), 3.05 (1H, m, CH$_2$ODMT), 2.85 (1H, m, CH$_2$ODMT), 2.77 (1H, m, NCH), 2.64 (1H, m, NCH), 1.15 (12H, m, NCH(CH$_3$)$_2$). Rf=0.28, 0.33 (20% Ethyl acetate in hexane).

EXAMPLE 19

(±)-O$^2$-(2-Cyanoethyl-N,N-Diisopropylphosphoramidite)-O$^1$-(4,4'-Dimethoxytrityl)-3-(3-Indolyl)-1,2-Dihydroxy propane 4,4'-Dimethoxytrityl chloride (1.7 g, 5.0 mmol) was added in portions to a stirred solution of (±)-3-(3-indolyl)-1,2 dihydroxypropane (0.87 g, 4.6 mmol) in anhydrous pyridine (150 mL) containing DMAP (0.28 g.). On addition, the solution was left to stir at RT overnight under nitrogen, after which the mixture was evaporated under vacuum. The residue was then adsorbed onto silica gel, and this mixture applied to a silica gel short path column and the product eluted using 1% methanol in dichloromethane. Homogenous fractions were combined, and evaporated in vacuo to give the (±)-O$^1$-(4,4'-dimethoxytrityl)-3-(3-indolyl)-1,2 dihydroxypropane as an oil (0.5 g, 22%).

$^1$H NMR δ 7.60–6.75 (18H, m, aromatic), 4.64 (1H, d, ex., O<u>H</u>), 3.92 (1H, m, C<u>H</u>OH), 3.72 (6H, s, OC<u>H</u>$_3$), 2.94 (3H, m, C<u>H</u>$_2$-ind.+C<u>H</u>$_2$—OH), 2.72 (1H, m, C<u>H</u>$_2$OH). Rf=0.25 (1% Methanol in dichloromethane).

2-Cyanoethyl-N,N-diisopropylchlorophosphoramidite (0.18 mL, 0.81 mmol) was added dropwise to a stirred solution of the above DMT derivative (0.4 g, 0.74 mmol) in anhydrous THF (25 mL) containing triethylamine (0.22 mL, 1.55 mmol). On addition, the mixture was stirred at RT overnight., and then filtered through a sintered glass funnel under nitrogen. The filtrate was evaporated under vacuum, and the residue dissolved in anhydrous benzene and then filtered. The filtrate was evaporated in vacuo, and the residue dissolved in an ethyl acetate/hexane mixture (3:7) and applied to a flash column. The product was eluted using 50% ethyl acetate in hexane containing 1% triethylamine, and homogenous fractions were combined and evaporated to give the product as a viscous oil, (0.224 g, 41%) having the following structure:

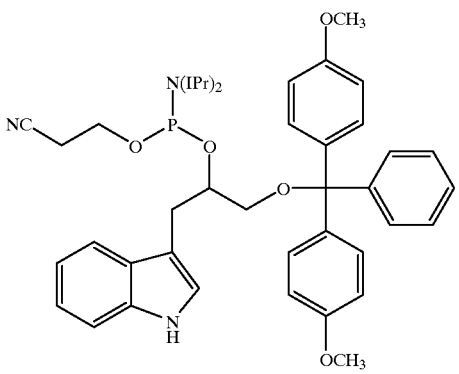

$^{31}$P NMR δ 148. $^{1}$H NMR δ 7.50–6.70 (18H, m, aromatic), 4.24 (1H, m, C<u>H</u>OH), 3.72 (6H, m, OC<u>H</u>$_{3}$), 3.70–3.42 (4H, m, C<u>H</u>$_{2}$CN+C<u>H</u>$_{2}$OP), 3.18–2.90 ( C<u>H</u>$_{2}$ODMT+CH$_{2}$-ind), 1.28–0.93 (12H, m, CH(C<u>H</u>$_{3}$)$_{2}$). Rf=0.47 (20% Ethyl acetate in hexane).

EXAMPLE 20

(±)-O$^{1}$-(2-Cyanoethyl-N,N-Diisopropylphosphoramidite)-O$^{2}$-(4,4'-Dimethoxytrityl)-N-Acetyl-2-Amino-4-(1,2-Dihydroxyethyl)-1,3-Thiazole A solution of ethyl 2-amino-4-thiazolglyoxylate (10 g, 50 mmol) in anhydrous THF (150 mL) was added dropwise to a suspension of lithium aluminum hydride (1.9 g) in anhydrous THF (200 mL), and the mixture stirred under nitrogen at RT for 1 h. Excess ethyl acetate was then added to destroy residual reductant, after which an excess of Glauber's Salt was added and the resultant suspension stirred at RT for 40 min. The slurry was then filtered, and the filtrate evaporated in vacuo, and then dissolved in methanol and adsorbed onto silica gel. This mixture was then applied to a flash silica column, and the product eluted using 10% methanol in dichloromethane. Homogenous fractions were combined and evaporated under vacuum to give (±)-2-amino-4-(1,2-dihydroxyethyl)-1,3-thiazole product as a pale orange colored solid, (2.6 g, 32.5%) with the following structure:

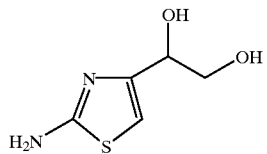

$^{1}$H NMR δ 6.74 (2H, s, N<u>H</u>$_{2}$), 6.28 (1H, s, aromatic), 4.92 (1H, broad, OH), 4.48 (1H, broad, OH), 4.34 (1H, m, C<u>H</u>OH), 3.60 (1H, d of d, C<u>H</u>$_{2}$OH), 3.38 (1H, m, C<u>H</u>$_{2}$OH). Rf=0.43 (30% Methanol in dichloromethane).

Acetic anhydride (4.5 mL, 47.4 mmol) was added to a solution of the above aminothiazole (2.3 g, 14.4 mmol) in anhydrous pyridine (30 mL) and the solution stirred under nitrogen at room temperature overnight. The mixture was then evaporated under vacuum, and the residue dissolved in ethly acetate. This solution was washed successively with 2M hydrochloric acid, saturated sodium bicarbonate solution, and then brine. The mixture was then dried over anhydrous sodium sulfate, filtered and the filtrate evaporated under reduced pressure. The residue was triturated with ether, after which the product separated as a tan colored solid which was collected by filtration, giving (±)-N$^{2}$,O,O-triacetyl-2-amino-4-(1,2-dihydroxyethyl)-1,3-thiazole as a powder, (1.08 g, 37%).

$^{1}$H NMR δ 7.14 (1H, s, aromatic), 5.96 (1H, m, CHOAc), 4.42 (1H, m, CH$_{2}$OAc), 4.33 (1H, m, C<u>H</u>$_{2}$OAc), 2.12 (3H, s, C<u>H</u>$_{3}$CO), 2.07 (3H, s, C<u>H</u>$_{3}$CO), 1.98 (3H, s, C<u>H</u>$_{3}$CONH). Rf=0.48 (10% Methanol in dichloromethane).

The above triacetylthiazole derivative (1.0 g, 3.7 mmol.) was suspended in methanol and 0.1 M sodium hydroxide solution (20 mL) was added in a single portion. The reaction mixture was stirred at room temperature and the reaction carefully monitored by TLC (10% methanol in dichloromethane). The reaction was stopped after 40 min by neutralizing the mixture using 2M hydrochloric acid in an ice bath. The resultant mixture was evaporated to dryness under vacuum, and the residue dissolved in a mixture of dichloromethane and methanol and then adsorbed onto silica gel. This material was applied to a flash silica column, and the product eluted using 15% methanol in dichloromethane. Homogenous fractions were combined and evaporated in vacuo to give (±)-N-acetyl-2-amino-4-(1,2-dihydroxyethyl)-1,3-thiazole as a tan colored powder (0.475 g, 69%).

$^{1}$H NMR δ 6.88 (1H, s, aromatic), 5.12 (1H, d, OH), 4.53 (1H, m, CH<u>OH</u>), 3.66 (1H, m, CH$_{2}$), 3.47 (1H, m, CH$_{2}$), 2.11 (3H, s, C<u>H</u>$_{3}$CO). Rf=0.22 (10% Methanol in dichloromethane).

The N-acetyl-derivatized thiazole derivative from the above reaction (0.915 g, 2.7 mmol.) was added in a single portion to a stirred solution of N-acetyl-2-amino-4-(1,2-dihydroxyethyl)-1,3-thiazole in anhydrous pyridine (20 mL) containing DMAP (20 mg). The resultant mixture was then left to stir at room temperature under nitrogen for 3 h, and was then evaporated under vacuum to give an orange colored oil. This material was dissolved in dichloromethane and adsorbed onto silica gel and then applied to a silica flash column. The product was eluted using 3% methanol in dichloromethane, and homogenous fractions combined and evaporated in vacuo to give an off-white foam of (±)-O$^{2}$-(4,4'-dimethoxytrityl)-N-acetyl-2-amino-4-(1,2-dihydroxyethyl)-1,3-thiazole (800 mg, 66%).

$^{1}$H NMR δ 7.44–6.80 (14H, m, aromatic), 5.42 (1H, d, OH), 4.79 (1H, m, C<u>H</u>OH), 3.73 (6H, s, OC<u>H</u>$_{3}$), 3.18 (1H, m, C<u>H</u>$_{2}$ODMT), 3.12 (1H, m, C<u>H</u>$_{2}$ODMT). Rf=0.34 (5% Methanol in dichloromethane).

2-Cyanoethyl-N,N-diisopropylchlorophosphoramidite (1.0 mL, 4.48 mmol) was added dropwise to a stirred solution of the above DMT derivative (1.0 g, 2.04 mmol) in anhydrous THF (45 mL) containing triethylamine (1.2 mL, 8.56 mmol). On addition, the mixture was stirred at RT for 4 h, and then filtered through a sintered glass funnel under nitrogen. The filtrate was evaporated under vacuum, and the residue dissolved in anhyrous benzene and then filtered. The filtrate was evaporated in vacuo, and the residue dissolved in an ethyl acetate hexane mixture (3:7) and applied to a flash column. The product was then eluted using 50% ethyl acetate in hexane containing 1% triethylamine, and homogenous fractions were combined and evaporated to give the title compound as a viscous oil, (0.224 g, 41%) with the following structure:

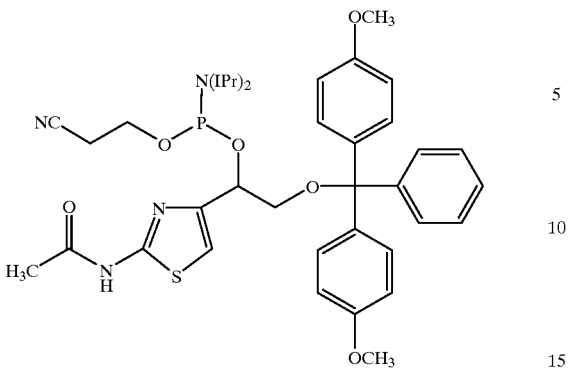

$^{31}$P NMR δ 149. $^1$H NMR δ 12.09 (1H, s, NH), 7.50–6.7 (14H, m, aromatic), 4.96 (1H, m, C<u>H</u>OP), 3.72 (6H, s, OC<u>H</u>$_3$), 3.62 (4H, m, C<u>H</u>$_2$OP+C<u>H</u>$_2$CN), 3.30 (1H, m, CH$_2$ODMT), 3.09 (1H, m, C<u>H</u>$_2$ODMT), 2.06 (3H, s, C<u>H</u>$_3$CO), 1.25–1.04 (12H, m, CH(C<u>H</u>$_3$)$_2$). Rf=0.52, 0.58 (50% Ethyl acetate in hexane).

EXAMPLE 21

O$^5$-(2-Cyanoethyl-N,N-Diisopropylphosphoramidite)-O$^1$-(4,4'-Dimethoxytrityl)-1,2,3,4-Tetrahydro-1,5-Dihydroxynaphthalene Dimethoxytrityl chloride (11.35 g, 33.5 mmol) was added to a stirred solution of 1,5-dihydroxy-1,2,3,4-tetrahydronaphthalene (5 g, 30.5 mmol) in pyridine (100 mL) containing DMAP (200 mg), and the resultant mixture was stirred for 2 h at room temperature under nitrogen. The reaction mixture was then poured into water and the product extracted with ethyl acetate. The extracts were washed with brine, dried over anhydrous sodium sulfate, filtered, and the filtrate evaporated in vacuo. The residue was then adsorbed onto silica gel, and the mixture applied to a silica gel short path column and the product eluted using 30% ethyl acetate in hexane. Homogenous fractions were combined and evaporated in vacuo to give O$^1$-(4,4'-dimethoxytrityl)-1,2,3,4-tetrahydro-1,5-dihydroxy naphthalene as an off-white foam, (5.52 g, 38%).

$^1$H NMR δ 9.01(1H, s, OH), 7.50–6.50 (16H, m, aromatic), 4.21 (1H, m, CHO<u>H</u>), 3.72 (6H, s, OC<u>H</u>$_3$), 2.60 (1H, m, C<u>H</u>$_2$-aromatic), 2.34 (1H, m, C<u>H</u>$_2$- aromatic), 1.88 (1H, m, alicyclic), 1.37 (1H, m, alicyclic), 1.28 (1H, m, alicyclic), 1.23 (1H, m, alicyclic). Rf=0.17 (30% Ethyl acetate in Hexane).

2-Cyanoethyl-N,N-diisopropylchlorophosphoramidite (0.56 mL, 2.5 mmol) was added dropwise to a stirred solution of the above DMT derivative (1.0 g, 2.3 mmol) in anhydrous THF (10 mL) containing diisopropylethylamine (0.88 mL, 5.1 mmol). On addition, the mixture was stirred at RT for 1 h, and was then filtered through a sintered glass funnel under nitrogen. The filtrate was evaporated under vacuum, and the residue dissolved in anhydrous benzene and then filtered. The filtrate was evaporated in vacuo, and the residue dissolved in an ethyl acetate/hexane mixture (3:7) and applied to a flash column. The product was then eluted using 30% ethyl acetate in hexane containing 1% triethylamine, and homogenous fractions were combined and evaporated to give the title compound as a viscous oil (0.92 g, 63%), having the following structure:

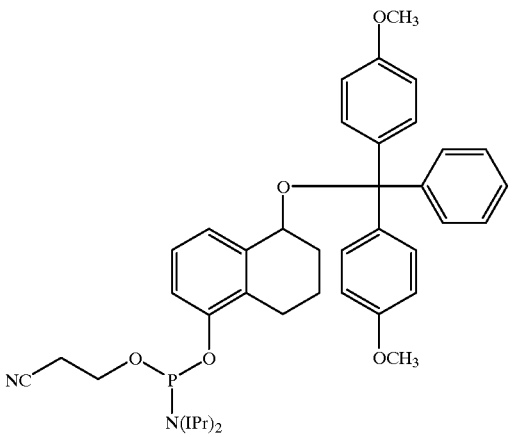

$^{31}$P NMR δ 145.6. $^1$H NMR δ 7.50–6.80 (16H, m, aromatic), 4.23 (1H, m, C<u>H</u>OP), 3.93–3.60 (10H, m, OC<u>H</u>$_3$+ C<u>H</u>$_2$OP+C<u>H</u>$_2$CN), 2.80 (2H, m, NC<u>H</u>), 2.70 (1H, m, benzylic C<u>H</u>), 2.42 (1H, m, benzylic C<u>H</u>), 1.88 (1H, m, alicyclic), 1.42 (1H, m, alicyclic), 1.31 (1H, m, alicyclic), 1.09 (13H, m, alicyclic+CH(C<u>H</u>$_3$)$_2$). Rf=0.42(30% Ethyl acetate in hexane).

EXAMPLE 22

Synthesis of 5'-O-(4,4'-dimethoxytrityl)-diol-triethylammonium-H-phosphonates

The DMT derivatives from examples 1 to 21 are dissolved in dry dichloromethane and added a flask over 10 minutes containing imidazole (15 equivalents), phosphorous trichloride (4.3 equivalents), triethylamine (29 equivalents), and dry dichloromethane cooled in an ice bath. The reaction mixture is stirred for 30 minutes at 0° C., the ice bath is removed and the mixture is stirred for an additional 30 minutes. Water is added and this mixture was stirred for 10 minutes. The layers are separated and the aqueous layer is extracted with chloroform. The combined organic layers are evaporated and then co-evaporated twice with toluene. The crude material is purified by column chromatography on silica gel eluting with a gradient of dichloromethane/methanol (0 to 30%). The purities of the fractions are monitored by thin layer chromatography (TLC) and fractions containing pure material are combined and evaporated to dryness. The resulting material is dissolved in dichloromethane and washed with 0.1 M triethylammonium bicarbonate. The aqueous layer is backwashed once with dichloromethane and the combined organic layers are evaporated to dryness to give the H-phosphonate monomer.

EXAMPLE 23

Synthesis of 5'-O-(4,4'-dimethoxytrityl)-1,2-dideoxy-D-ribose-3'-H-phosphonate

5'-(4,4'-dimethoxytrityl)-1,2-dideoxy-D-ribose (5.6 g, 13.4 mmol) was treated according to the protocol used in example 22 to give 5'-O-(4,4'-dimethoxytrityl)-1,2-dideoxy-D-ribose-3'-H-phosphonate (6.3 g) as a colorless foam having the following structure:

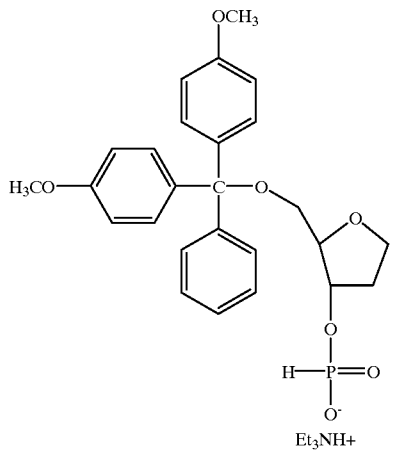

$^{31}$P NMR (202 MHz) DMSO δ (ppm) 0.61 (doublet of doublets, $J_{P-H}$=578 Hz, $J_{P-O-C-H}$=9.1 Hz). TLC Rf=0.37 (8:2 dichloromethane/methanol/0.1% triethylamine).

EXAMPLE 24

Synthesis of 1-(4,4'-dimethoxytrityl)-3-(4-methoxyphenoxy)1,2-propanediol-2-H-phosphonate 1-(4,4'-Dimethoxytrityl)-3-(4-methoxyphenoxy)-1,2-propanediol (3 g, 6 mmol) was treated according to the protocol used in example 22 to give 1-(4,4'-dimethoxytrityl)-3-(4-methoxyphenoxy-1,2-propanediol-2-H-phosphonate (0.65 g) as a colorless oil having the following structure:

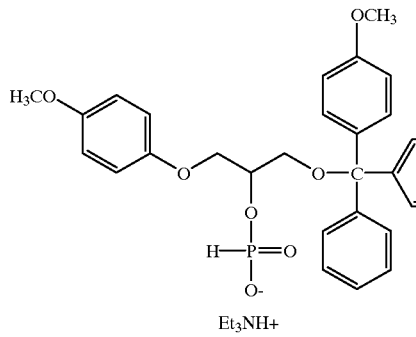

$^{31}$P NMR (202 MHz) DMSO δ (ppm) 1.5 (doublet of doublets, $J_{P-H}$=586 Hz, $J_{P-O-C-H}$=10.7 Hz). TLC Rf=0.26 (9/1 dichloromethane/methanol).

EXAMPLE 25

Synthesis of 1-(4,4'-dimethoxytrityl)-3-(diethylamino)-1,2-propanediol-2-H-phosphonate 1-(4,4'-Dimethoxytrityl)-3-(diethylamino)-1,2-propanediol (2.7 g, 6 mmol) was treated according to the protocol used in example 22 to give 1-(4,4'-dimethoxytrityl)-3-(diethylamino)-1,2-propanediol-2-H-phosphonate (4.1 g) as an oil having the following structure:

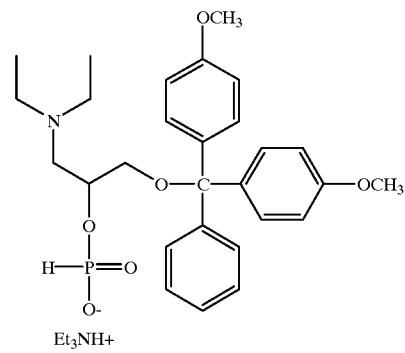

$^{31}$P NMR (202 MHz) DMSO δ (ppm) 5.2 (dd, $J_{P-H}$=601 Hz, $J_{P-O-C-H}$=10.7 Hz). TLC Rf 0.26 (9:1 dichloromethane/methanol).

EXAMPLE 26

Synthesis of 4,4'-dimethoxytrityl-trans-9,10-ethanoanthracene-11,12-dimethanol-H-phosphonate 4,4'-Dimethoxytrityl-trans-9,10-ethanoanthracene-11,12-dimethanol (1.64 g, 2.9 mmol) was treated according to the protocol used in example 22 to give 4,4'-dimethoxytrityl-trans-9,10-ethanoanthracene-11,12-dimethanol-H-phosphonate (1.8 g) as a white foam having the following structure:

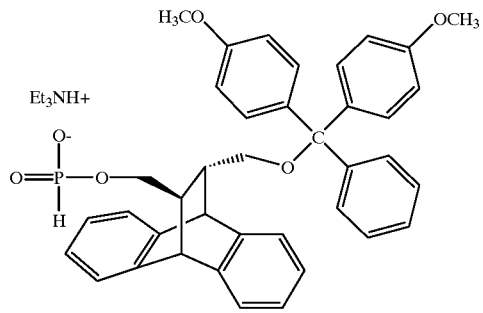

$^{31}$P NMR (202 MHz) DMSO δ (ppm) 1.6 ($J_{P-H}$=613 Hz). TLC Rf=0.09 (dichloromethane/0.5% triethylamine).

EXAMPLE 27

Synthesis of 2-(4,4'-dimethoxytrityl)-2,6-bis-hydroxymethylpyridine-6-H-phosphonate 2-(4,4'-Dimethoxytrityl)-2,6-bis-hydroxymethylpyridine (7.0 g, 15.8 mmol) was treated according to the protocol used in example 22 to give 2-(4,4'-dimethoxytrityl)-2,6-bis-hydroxymethylpyridine-6-H-phosphonate (8 g) as a yellow oil having the following structure:

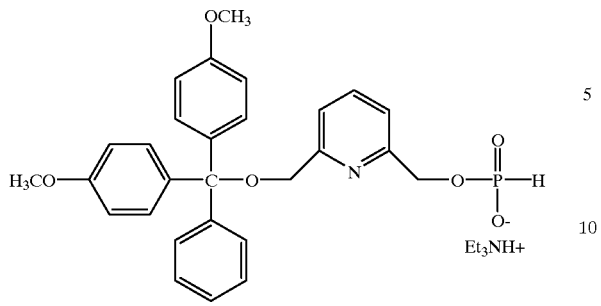

$^{31}$P NMR (202 MHz) DMSO δ (ppm) 1.65 (doublet of triplets, $J_{P-H}$=584 Hz, $J_{P-O-CH2}$=9.1 Hz). TLC Rf 0.08 (9:1 dichloromethane/methanol/0.1% triethylamine).

EXAMPLE 28

Synthesis of 7-(4,4'-dimethoxytrityl)-trans-7,8-dihydroxy-dimethyl-exo-tricyclononene[4.2.1.0$^{2,5}$] nona-3-ene-3,4-dicarboxylate-8-H-phosphonate 7-(4,4'-Dimethoxytrityl)-trans-7,8-dihydroxy-dimethyl-exo-tricyclononene [4.2.1.0$^{2,5}$]nona-3-ene-3,4-dicarboxylate (3.5 g, 6.1 mmol) was treated according to the protocol used in example 22 to give 7-(4,4'-dimethoxytrityl)-trans-7,8-dihydroxy-dimethyl-exo-tricyclononene[4.2.1.0$^{2,5}$]nona-3-ene-3,4-dicarboxylate-8-H-phosphonate (4.8 g) as a white foam having the following structure:

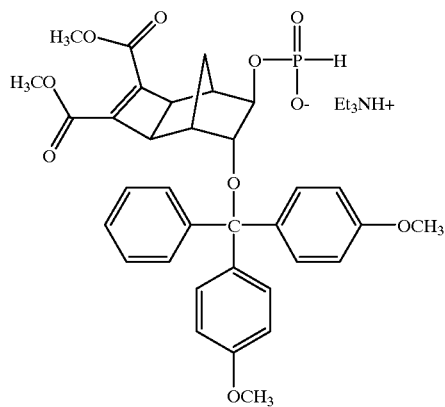

$^{31}$P NMR (202 MHz) DMSO δ (ppm) 0.66 ($J_{P-H}$=613 Hz). TLC Rf 0.12 (9:1 dichloromethane/methanol/0.1% triethylamine).

EXAMPLE 29

Synthesis of (4,4'-dimethoxytrityl)-hydroquinone-bis-(hydroxyethyl)-ether-H-phosphonate (4,4'-Dimethoxytrityl)-hydroquinone-bis-(hydroxyethyl)-ether (2.2 g, 4.4 mmol), prepared according to the protocol used in example 4, was treated according to the protocol used in example 22 to give (4,4'-dimethoxytrityl)-hydroquinone-bis-(hydroxyethyl)-ether-H-phosphonate (2.5 g) as a white sticky solid having the following structure:

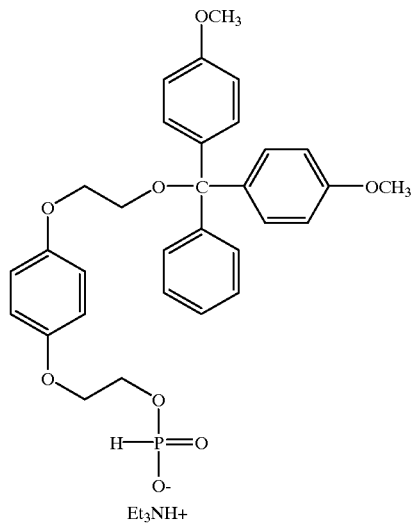

$^{31}$P NMR (202 MHz) DMSO δ (ppm) 1.9 ($J_{P-H}$=578 Hz). TLC Rf 0.09 (9:1 dichloromethane/methanol/0.1% triethylamine).

EXAMPLE 30

Synthesis of (4,4'-dimethoxytrityl)-N,N-bis-(2-hydroxyethyl)-isonicotinamide-H-phosphonate (4,4'-dimethoxytrityl)-N,N-bis-(2-hydroxyethyl)-isonicotinamide (10.2 g, 19.9 mmol), prepared according to the protocol used in example 4, was treated according to the protocol used in example 22 to give (4,4'-dimethoxytrityl)-N,N-bis-(2-hydroxyethyl)-isonicotinamide-H-phosphonate (10.5 g) as a white foam having the following structure:

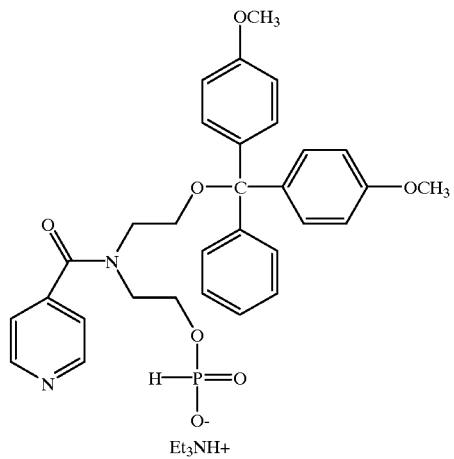

$^{31}$P NMR (202 MHz) DMSO δ (ppm) 1.55 (1H, doublet of triplets, $J_{P-H}$=583 Hz, $J_{P-O-CH2}$=7.7 Hz), 1.98 (1H, doublet of triplets, $J_{P-H}$=583 Hz, $J_{P-O-CH2}$=9.1 Hz). TLC Rf 0.06 (9:1 dichloromethane/methanol/0.1% triethylamine).

EXAMPLE 31

Synthesis of 3-(4,4'-dimethoxytrityl)-2-amino-1-phenyl-1,3-propanediol-H-phosphonate 3-(4,4'-dimethoxytrityl)-2-amino-1-phenyl-1,3-propanediol (8.0 g, 14.1 mmol), prepared according to the protocol used in example 4, was treated according to the protocol used in example 22 to give 3-(4,4'-dimethoxytrityl)-2-amino-1-phenyl-1,3-propanediol-H-phosphonate (7.1 g) as a white foam having the following structure:

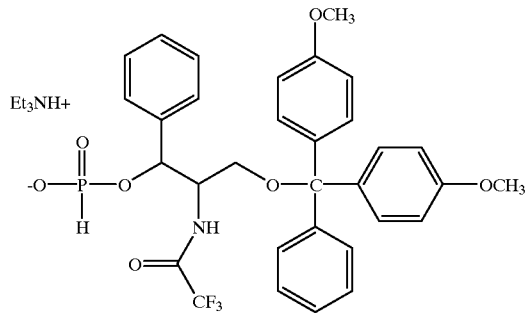

$^{31}$P NMR (202 MHz) DMSO δ (ppm) 0.66 (doublet of doublets, $J_{P-H}$=594 Hz, $J_{P-O-CH2}$=12.1 Hz). TLC Rf 0.11 (9:1 dichloromethane/methanol/0.1% triethylamine).

EXAMPLE 32

Synthesis of (4,4'-dimethoxytrityl)-1,4-bis-(hydroxyethyl)-piperazine-H-phosphonate (4,4'-dimethoxytrityl)-1,4-bis-(hydroxyethyl)-piperazine (10.2 g, 21.3 mmol), prepared according to the protocol used in example 4, was treated according to the protocol used in example 22 to give (4,4'-dimethoxytrityl)-1,4-bis-(hydroxyethyl)-piperazine-H-phosphonate (9.1 g) as a white foam having the following structure:

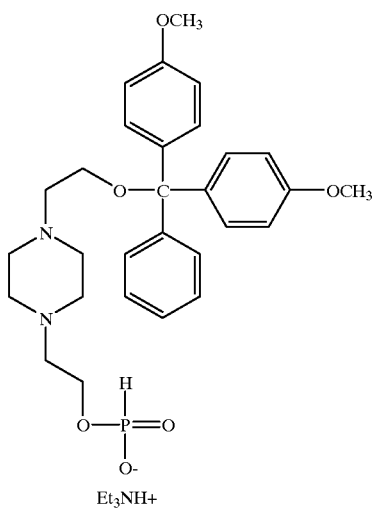

$^{31}$P NMR (202 MHz) DMSO δ (ppm) 4.3 (doublet of triplets, $J_{P-H}$=595 Hz, $J_{P-O-CH2}$=13.7 Hz). TLC Rf 0.11 (8:2 dichloromethane/methanol/0.1% triethylamine).

EXAMPLE 33

Synthesis of (4,4'-dimethoxytrityl)-ethylene glycol-H-phosphonate (4,4'-dimethoxytrityl)-ethylene glycol (2.9 g, 7.96 mmol), prepared according to the protocol used in example 4, was treated according to the protocol used in example 22 to give (4,4'-dimethoxytrityl)-ethylene glycol-H-phosphonate (3.8 g) as a yellow oil having the following structure:

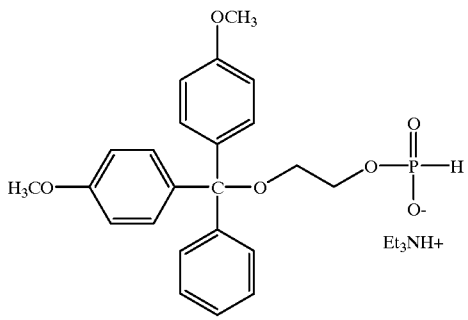

$^{31}$P NMR (202 MHz) DMSO δ (ppm) 2.0 ($J_{P-H}$=580 Hz). TLC Rf 0.09 (95:5 dichloromethane/methanol/0.5% triethylamine).

EXAMPLE 34

Synthesis of 1-(4,4'-dimethoxytrityl)1-S-1,2-propanediol-H-phosphonate 1-(4,4'-dimethoxytrityl)-1,2-propanediol (2.3 g, 6.0 mmol), prepared according to the protocol used in example 4, was treated according to the protocol used in example 22 to give 1-(4,4'-dimethoxytrityl)-1,2-propanediol-H-phosphonate (1.75 g) as a yellow gum having the following structure:

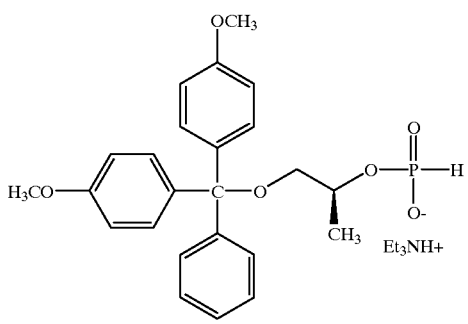

$^{31}$P NMR (202 MHz) DMSO δ (ppm) 1.7 ($J_{P-H}$=616 Hz). TLC Rf 0.04 (95:5 dichloromethane/methanol/0.5% triethylamine).

EXAMPLE 35

Synthesis of 1-(4,4'-dimethoxytrityl)-1,2-dihydroxy-3-R-butene-H-phosphonate 1-(4,4'-dimethoxytrityl)-1,2-dihydroxy-3-butene (4.4 g, 11.2 mmol), prepared according to the protocol used in example 4, was treated according to the protocol used in example 22 to give 1-(4,4'-dimethoxytrityl)-1,2-dihydroxy-3-butene-H-phosphonate (4.2 g) as a yellow gum having the following structure:

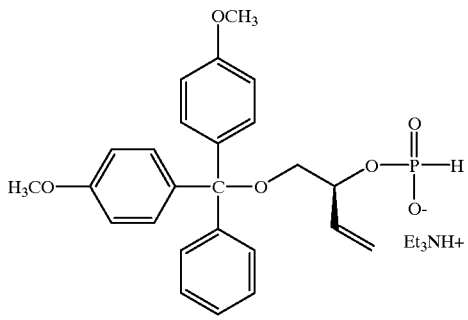

$^{31}$P NMR (202 MHz) DMSO δ (ppm) 8.17 ($J_{P—H}$=703 Hz). TLC Rf 0.13 (3:7 ethylacetate/hexane/0.5% triethylamine).

EXAMPLE 36

Synthesis of 3-(4,4'-dimethoxytrityl)-1-R-phenyl-1,3-propanediol-H-phosphonate 3-(4,4'-dimethoxytrityl)-1-phenyl-1,3-propanediol (2.5 g, 5.5 mmol), prepared according to the protocol used in example 4, was treated according to the protocol used in example 22 to give 3-(4,4'-dimethoxytrityl)-1-phenyl-1,3-propanediol-H-phosphonate (2.3 g) as a yellow foam having the following structure:

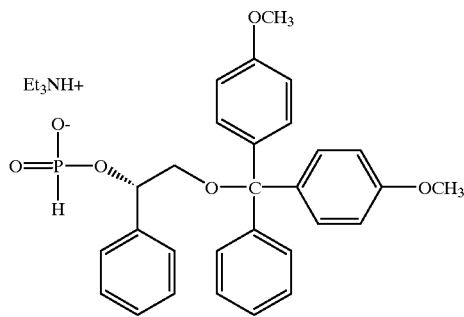

$^{31}$P NMR (202 MHz) DMSO δ (ppm) −1.7 ($J_{P—H}$=585 Hz). TLC Rf 0.084 (94:6 dichloromethane/methanol/0.5% triethylamine).

EXAMPLE 37

Synthesis of (4,4'-dimethoxytrityl)-2,3-dihydroxypropyl-theophylline-H-phosphonate (4,4'-dimethoxytrityl)-2,3-dihydroxypropyl-theophylline (1.9 g, 3.5 mmol), prepared according to the protocol used in example 4, was treated according to the protocol used in example 22 to give (4,4'-dimethoxytrityl)-theophylline-H-phosphonate (2.6 g) as a white foam having the following structure:

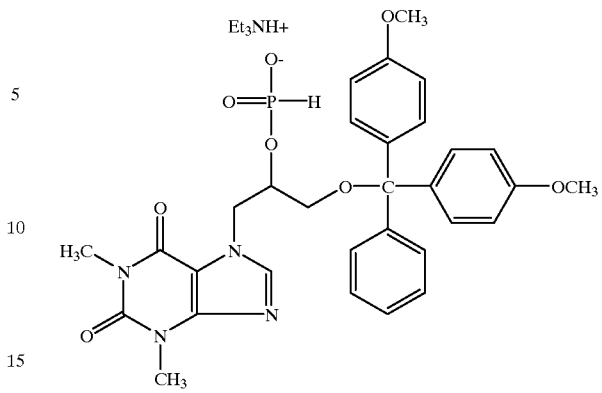

$^{31}$P NMR (202 MHz) DMSO δ (ppm) 0.76 (doublet of doublets, $J_{P—H}$=584 Hz, $J_{P—O—CH}$=8.5 Hz)). TLC Rf 0.34 (94:6 dichloromethane/methanol/0.5% triethylamine).

EXAMPLE 38

Synthesis of (4,4'-dimethoxytrityl)-pilocarpine-H-phosphonate (4,4'-dimethoxytrityl)-pilocarpine (1.2 g, 1.8 mmol), prepared according to the protocol used in example 4, was treated according to the protocol used in example 22 to give (4,4'-dimethoxytrityl)-pilocarpine-H-phosphonate (1.5 g) as a pale yellow foam having the following structure:

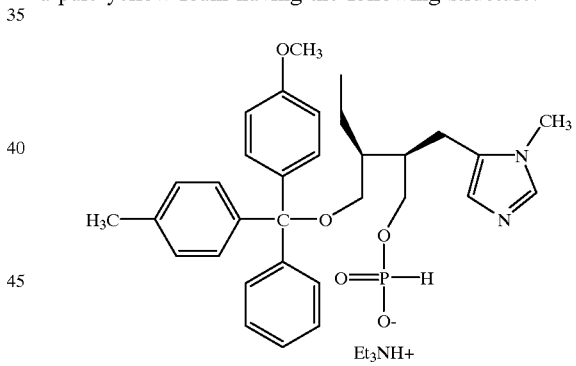

$^{31}$P NMR (202 MHz) DMSO δ (ppm) 1.8 ($^{J}$p-H=573 Hz). TLC Rf 0.122 (95:5 dichloromethane/methanol/1% triethylamine).

EXAMPLE 39

Synthesis of (4,4'-dimethoxytrityl)-1S,2S,3R,5S-(+)-pinanediol-H-phosphonate (4,4'-dimethoxytrityl)-1S,2S,3R,5S-(+)-pinanediol (2.51 g, 5.36 mmol), prepared according to the protocol used in example 4, was treated according to the protocol used in example 22 to give (4,4'-dimethoxytrityl)-1S,2S,3R,5S-(+)-pinanediol-H-phosphonate (1.8 g) as a pale yellow foam having the following structure:

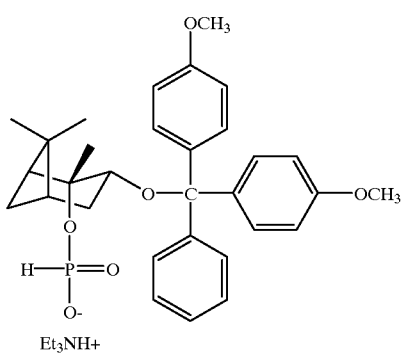

$^{31}$P NMR (202 MHz) DMSO δ (ppm) −1.7 ($J_{P-H}$=585 Hz). TLC Rf 0.234 (95:5 dichloromethane/methanol/0.5% triethylamine).

EXAMPLE 40

Synthesis of (4,4'-dimethoxytrityl)-thiomicamine-trifluoroacetamide-H-phosphonate (4,4'-dimethoxytrityl)-thiomicamine-trifluoroacetamide (3.6 g, 6.0 mmol), prepared according to the protocol used in example 4, was treated according to the protocol used in example 22 to give (4,4'-dimethoxytrityl)-thiomicamine-trifluoroacetamide-H-phosphonate (3.0 g) as a pale yellow foam having the following structure:

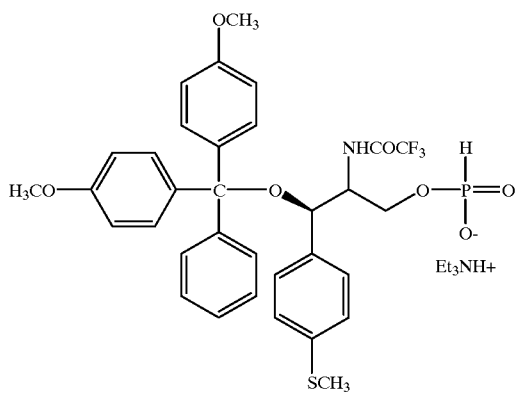

$^{31}$P NMR (202 MHz) DMSO δ (ppm) −1.7 ($J_{P-H}$=585 Hz). TLC Rf 0.234 (95:5 dichloromethane/methanol/0.5% triethylamine).

EXAMPLE 41

Synthesis of (4,4'-dimethoxytrityl)-pyridoxine-R-phosphonate (4,4'-dimethoxytrityl)-pyridoxine (4.57 g, 9.69 mmol), prepared according to the protocol used in example 4, was treated according to the protocol used in example 22 to give (4,4'-dimethoxytrityl)-pyridoxine-H-phosphonate (3.9 g) as a white foam having the following structure:

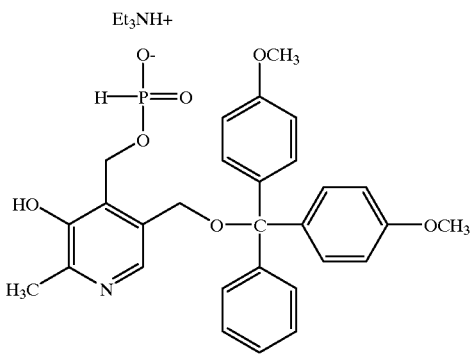

$^{31}$P NMR (202 MHz) DMSO δ (ppm) 1.9 ($J_{P-H}$=587 Hz). TLC Rf 0.33 (8:2 dichloromethane/methanol/0.1% triethylamine).

EXAMPLE 42

Synthesis of a Tetrameric Phosphorus Ester

Samples of the monomers from examples 15, 7, 12 and 5 were separately diluted in anhydrous acetonitrile to give a 0.2 M solution of each. These solutions were used in a standard amidite syntheses on an automated DNA synthesizer using the 1 μmol phosphoramidite cycle with an extended coupling time of 5 min. The oligomer was synthesized on a thymidine-derivatized solid support that had been initially derivatized with the chemical phosphorylation reagent (2-cyanoethoxy)-2-(2'-O-4,4'-dimethoxytrityloxyethylsulfonyl)ethoxy-N,N'-diisopropylaminophosphine. After the addition of each of the monomers to the column, added in the order specified above, the efficiency of the coupling was checked by monitoring of the trityl colors from each cycle, and was determined to be in excess of 95% throughout all of the coupling steps. After the addition of the monomers, deoxycytidine phosphoramidite was added for labeling purposes. The column was then treated with concentrated ammonium hydroxide for 4 h at 55° C. and the ammonia removed by bubbling the solution with nitrogen for 20 min. The solution was lyophilized, and the residue dissolved in water and purified on a C18 HPLC column using a gradient of acetonitrile (solvent B)/triethylammonium acetate, pH 7 (solvent A). Gradient: 8–20% B over 24 min, then 20–40% B over 10 min. The material eluting at 14.75 min was lyophilized to give an oligomer with the following structure:

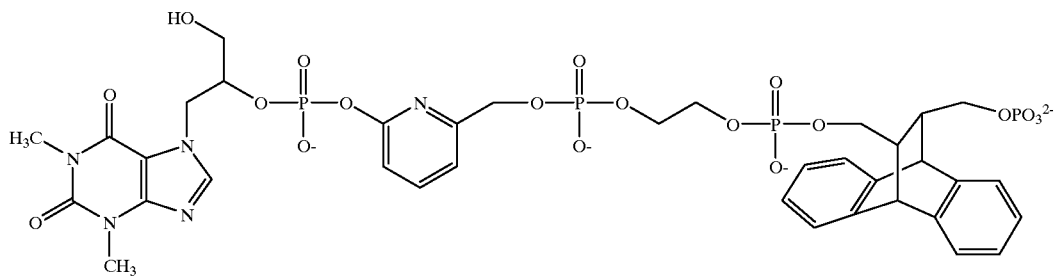

EXAMPLE 43

Synthesis of a Fluorescein-Labeled Pentamer Library

Samples of the monomers from examples 1–10 were separately diluted in anhydrous acetonitrile to give 2 mL of a 0.2 M solution of each. These solutions were used in a standard amidite syntheses on three Applied Biosystems 394 Automated DNA synthesizers using the 1 μmol phosphoramidite cycle with an extended coupling time of 5 min for each. The library was synthesized on ten columns each loaded with 10 mg of 100 μm thymidine-derivatized controlled pore glass support that had been derivatized with the chemical phosphorylation reagent (2-cyanoethoxy)-2-(2'-O-4,4'-dimethoxytrityl-oxyethylsulfonyl)ethoxy-N,N'-diisopropyl-aminophosphine. After the addition of each of the monomers to their specified columns the efficiency of the coupling was checked by monitoring of the trityl colors from each synthesis, and was determined to be in excess of 90% throughout all of the coupling steps. After each synthesis cycle, the resins were removed from the columns and pooled and divided using the isopycnic slurry method. The synthesis columns were then weighed to ensure an even division of the resin between the columns, the variation of which was determined to be less than 5% throughout the four pooling and dividing steps. After the addition of the fifth amidite, the oligomers in each of the ten columns were fluoresceinated using fluorescein 6-FAM amidite (Applied Biosystems, Foster City, Calif.). The resin from each column was then removed, and treated with concentrated ammonium hydroxide for 4 h at 55° C. The resultant suspensions were filtered and the ammonia removed from the filtrate by bubbling the solutions with nitrogen for 20 min. The ten solutions were then lyophilyzed and the residues dissolved in water and purified over an OPC cartridge (Applied Biosystems) using the standard procedure as provided by the manufacturer. The products from the purification were then analyzed by electrophoresis on a non-denaturing polyacrylamide gel. Each of the ten products ran as a single band, with almost the same mobility as a pentameric deoxyoligonucleotide. The library was then assembled by mixing all of these solutions and lyophilizing the resultant mixture.

EXAMPLE 44

Synthesis of a $^{32}$P-Labeled Trimer Phosphoramidate Library

Samples of the monomers from examples 23, 27, 29, 32–37 and 39 were separately diluted in 1:1 anhydrous acetonitrile/pyridine to give a 0.12 M solution of each. These solutions were used in two automated DNA synthesizers using a modified H-phosphonate cycle with an extended coupling time of 5 minutes for each monomer. The library was synthesized on 10 columns each loaded with 60 mg of long chain alkylamine controlled pore glass (37–70 μm, 44 umol/g), that had been derivatized with dimethoxytrityl-thymidine. Each column was initially reacted with the chemical phosphorylating reagent (2-cyanoethoxy)-2-(2'-O-4,4'-dimethoxytrityloxyethylsulfonyl)ethoxy-N,N'-diisopropylaminophosphine using the standard phosphoramidite procedure. Each of the 10 monomers was then coupled to its specified column, monomer one to column one, monomer two to column two, etc., up to monomer 10 to column 10. The efficiency of each coupling was checked by monitoring the trityl colors from each synthesis, and was determined to be in excess of 90% throughout all of the coupling steps. After addition of the 10 monomers, the resins were then removed from the columns and pooled and divided using the isopycnic slurry method. The synthesis columns were weighed to ensure an even division of the resin among the columns. After a second addition of all 10 monomers as previously described, followed by a second pool-and-divide procedure, the non-nucleotide H-phosphonate linkages were converted to phosphoramidate linkages using the following oxidation procedure with each column being oxidized with one of the amines listed below:

1. 2-(2-Aminoethyl)pyridine,
2. 1-(2-Aminoethyl)piperidine,
3. 2-(3,4-Dimethyloxyphenyl)ethylamine,
4. 4-(2-Aminoethyl)-morpholine,
5. 1-(3-Aminopropyl)-2-pyrrolidinone,
6. 2-(3-chlorophenyl)ethylamine,
7. 4-Bromophenethylamine,
8. N-(3-trifluoromethyl)phenylpiperazine,
9. 3,3-Diphenylpropylamine,
10. Thiomorpholine,
11. 1-(2-Pyridyl)piperazine,
12. Hexamethyleneimine,
13. cis-2,6-Dimethylmorpholine,
14. 1-(4-fluorophenyl(piperazine,
15. 4-Fluorophenethylamine,
16. 3,5-Dimethylpiperidine.

A 10% solution of each amine was prepared individually in carbon tetrachloride and the H-phosphonate linkages of the oligomers were then oxidized to phosphoramidates using the freshly prepared solution of the required amine for 10 minutes. The amine solutions were then flushed from the columns and the supports were washed extensively with acetonitrile. The supports were removed from the columns and pooled and divided as described above. A second round of monomer addition followed by pooling, dividing and amine addition was carried out, followed by addition of thymidine-H-phosphonate at the last step to provide an attachment site for the $^{32}$P label. The supports were then removed from the columns and treated with concentrated ammonium hydroxide for 5.5 hours at 55° C. The resultant suspensions were filtered and the ammonia removed from the filtrates by bubbling the solutions with nitrogen for 20 minutes. The sixteen solutions then were lyophilized, redissolved in water and purified by reversed-phase HPLC using a gradient of 5–100% acetonitrile in TEAA, 0.1 M, pH 7. The products from these purifications were combined and resultant mixture was lyophilized to give the oligomeric phosphoramidate library which was then labeled with $^{32}$P by a conventional method using T4 polynucleotide kinase.

EXAMPLE 45

Synthesis of a Disulfide-Bridged Phosphorus Ester Oligomer

The 3',5'-dithiol oligomer was synthesized on an Applied Biosystems Model 394 DNA synthesizer on a 1 μmol scale using 0.02 M solution of iodine for all of the oxidation steps. 1-O-Dimethoxytrityl-hexyl-disulfide-1'-[(2-cyanoethyl)-N, N-diisopropylphosphoramidite] (thiol modifier C6 S-S, Glen Research, Stirling, Va.) was directly coupled to a nucleoside residue anchored to a controlled pore glass solid support (i.e. a thymidine column) and the coupling time was extended to 15 min in this cycle and the following two phosphoramidite coupling cycles. The monomer phosphoramidites as specified in examples 2, 1, 3, 2, 3 and 1 were then incorporated sequentially in the exact order specified using a coupling time of 5 min for each. Fluorescein phosphoramidite (ClonTech Co.) was then added followed by the thiol modifier C6 S-S using a 15 min coupling time. Coupling efficiencies for the monomers averaged 88%, as determined by trityl assay.

After the synthesis and cleavage from the solid support, the solution was concentrated to a small volume and the tritylated oligomer was isolated by HPLC on a preparative C$_{18}$ column using a gradient of acetonitrile in 0.1 M triethylammonium acetate (TEAA) buffer (5–30% over 15 min then 30–55% over 30 min, then at 55% for 20 min). Fractions eluting at 47–51 min were evaporated to dryness and redissolved in 0.1 M TEAA buffer (pH 8.0, 0.5 mL). After addition of dithiothreitol (DTT, 10 mg), the resulting mixture was stirred under an argon blanket at room temperature for 4 hrs to cleave the disulfide bonds and liberate free thiol groups at both ends of the oligomer. The disulfide bond cleavage reaction was monitored by HPLC using a C$_{18}$ analytical column. The byproducts were removed by extraction with ethyl acetate (3×) and ether (2×) and the intermediate oligomer dithiol was purified by HPLC on a preparative C$_{18}$ column using a gradient of 2–20% acetonitrile in 0.1 M TEAA buffer over 15 min followed by 20–50% over 30 min, then 50–65% over 15 min. The fraction eluting between 30–35 min was evaporated to dryness, dissolved in triethylammonium acetate buffer pH 8.0 (1 mL) and oxidized with oxygen with stirring at room temperature for 1 day. The reaction mixture was analyzed by HPLC on a C$_{18}$ analytical column using a gradient of acetonitrile in 0.1 M TEAA buffer (5–30% over 10 min, then 15–50% over 23 min, then 50–80% over 7 min. The appropriate fractions were lyophilized to give a disulfide-bridged oligomer (HPLC retention time 24.0 min) with the following structure:

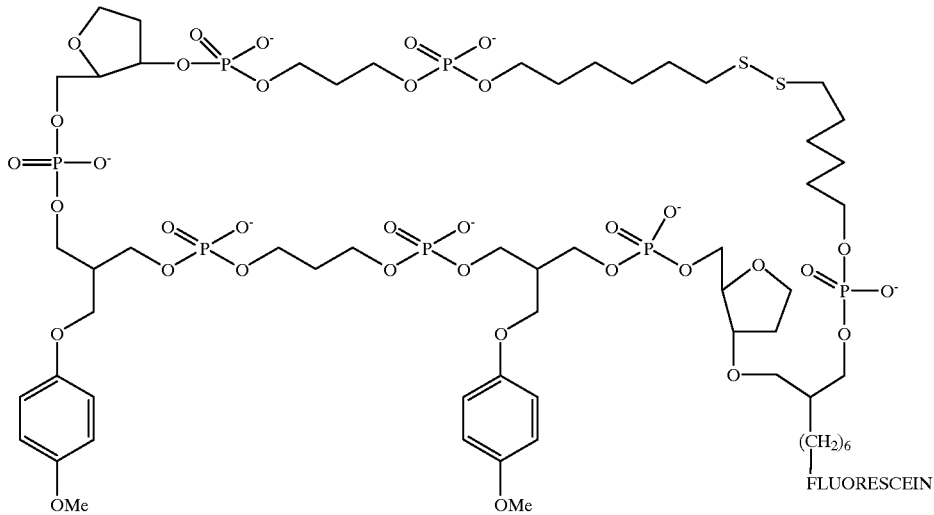

EXAMPLE 46

Serum Stability of a Non-nucleotide Oligomeric Phosphorus Ester

The H-phosphonate synthesis method was used to prepare a fluorescein-labeled pentamer with the following structure:

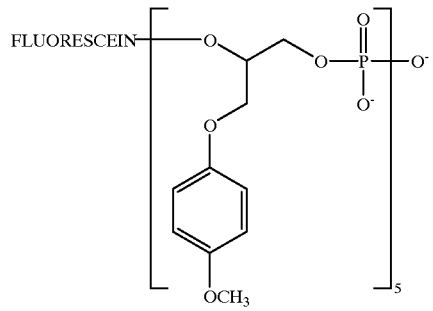

Portions (9.6 nmol) of this material in separate tubes were each dissolved in water (105 μL), added to human serum (500 μL) and incubated at 37°. At various time points, samples were filtered through a 0.45 μm filter and analyzed by ion exchange HPLC using a Dionex PA-100 column (4×250 mm). The column was eluted with a gradient of 25 mM Tris chloride, 1M ammonium chloride, pH 8 (buffer B) in 25 mM Tris chloride, pH 8 (buffer A), using 15–65% B over 19 min, then 65% B for 2 min, then 65–75% B over 2 min. The area under the peak corresponding to starting material was measured versus time to determine the degradation rate. By this method the $t_{1/2}$ was determined to be greater than 1 month. A 20-base oligodeoxynucleotide was used as a control, and under the same conditions, the $t_{1/2}$ for this oligonucleotide was determined to be 7 min.

EXAMPLE 47

Binding of a Library of Phosphorus Ester Oligomers to Protein Targets

The oligomeric library of Example 43 was screened against the target proteins IL-4 and IFNγ for high affinity ligands, using the COMPILE method as outlined in copending patent application "Determination and Identification of Active Compounds in a Compound Library," U.S. patent application Ser. No. 08/223,519. Binding reactions consisting of 2.5 μM oligomeric library and 1 μM target protein as well as a protein-minus control (data not shown) were prepared in a buffer containing 150 mM NaCl, 3 mM $MgCl_2$ and 25 mM Tris-HCl (pH 7.5). The reactions were equilibrated for 30 min at room temperature prior to centrifugation through Microcon-10 spin filtration units (M. Wt.cutoff=10,000). The M. Wt. cutoff of the filtration unit was selected to allow free passage of the oligomeric library members but not the target protein or the oligomeric molecules bound to it.

The centrifugation was adjusted to allow approximately 270 μL of the total reaction volume of 400 μL to flow through the membrane, resulting in the loss of approximately 67% of the unbound oligomeric library from the retained sample. The volume of the retained sample was brought up to the original 400 μL with buffer (containing 20% of the original target concentration to compensate for losses/inactivation of the target during the experiment) and the selection was repeated.

Figure 3:
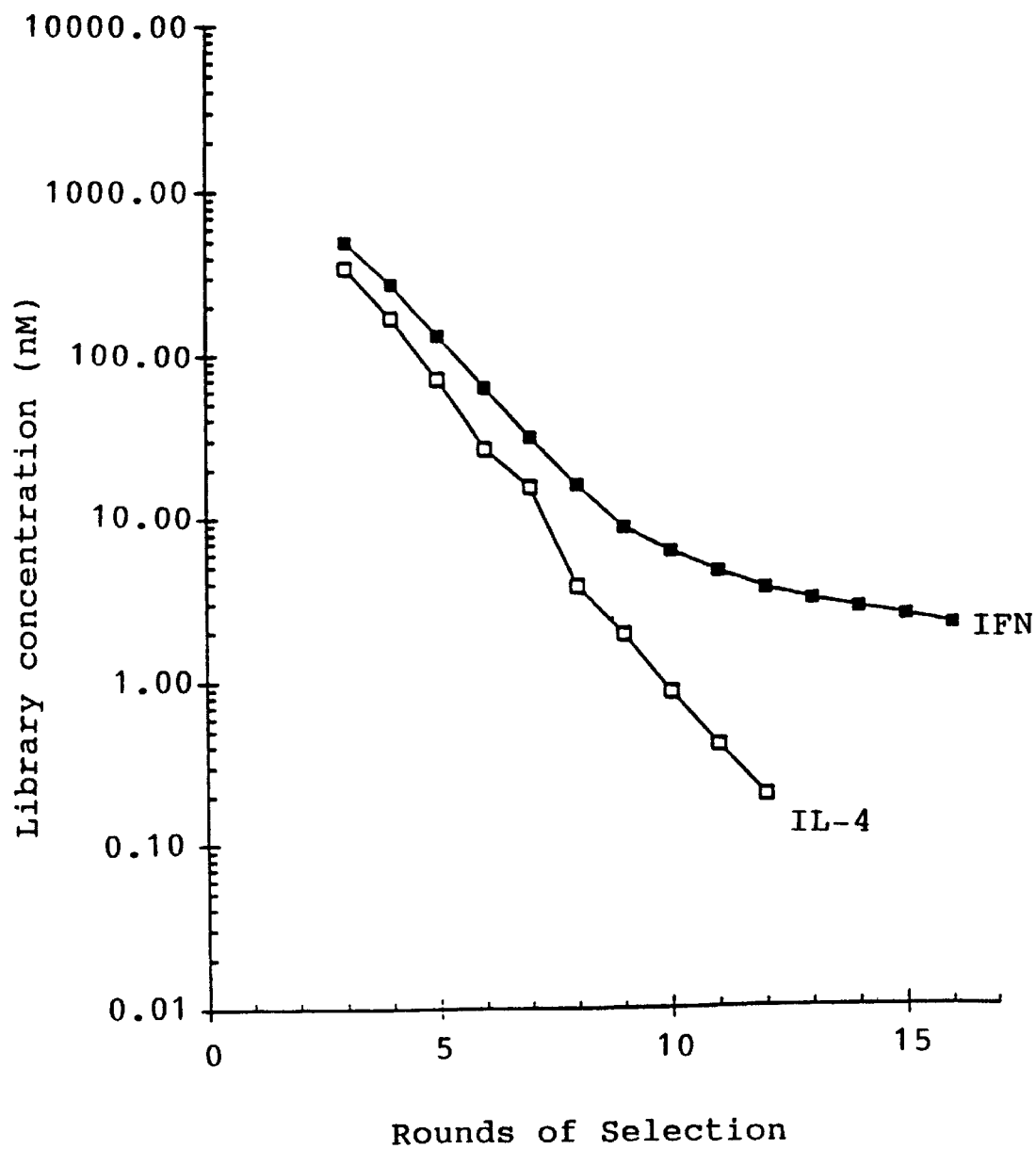
FIG. 3 shows the binding of a combinatorial library of non-nucleotide phosphorus ester oligomers to two protein targets.

The results of this serial selection are presented in FIG. 3. The concentration of the oligomeric library present in the retained fraction (as measured by fluorescence of the fluorescein tag incorporated into the library members) is plotted as a function of the rounds of selection—i.e. the number of dialysis-based separations. It should be noted here that any method of separation of target-bound library members from unbound library members, even separation not based on size, could have been chosen. Data are not presented for the first two rounds of selection since the library was in excess over target at that point, and we would not observe protein dependent retention of the library.

As shown in FIG. 3, the oligomeric library members are lost at approximately the same rate for both IL-4 and IFNγ (and for the protein-minus control—data not shown) over the first seven rounds of selection. At this point, however, the IFNγ reaction begins to retain a progressively larger fraction of the library whereas the IL-4 reaction fails to show such increased proportion of retention.

The progressive increase in the fraction of compounds retained at each round, as observed with the IFNγ reaction, is evidence of a subpopulation of the original library that binds to the target. This subpopulation is enriched with each successive round of selection due to selective retention of compounds in the library that bind to the target protein. From the target protein concentration and the curve shown in FIG. 3, it is possible to calculate that this subpopulation of IFNγ-binding oligomeric species is about 1% of the original mixture, and that it binds with Kd of approximately 250 nM.

EXAMPLE 48

Synthesis of 1-O-(4,4'-dimethoxytrityl)-1,2,3,4-tetrahydro-1,5-dihydroxynaphthalene-5-H-phosphonate 1-O-(4,4'-dimethoxytrityl)-1,2,3,4-tetrahydro-1,5-dihydroxynaphthalene (4.77 g, 10.2 mmol) was treated according to the protocol used in Example 22 to give 1-O-(4,4'-dimethoxytrityl)1,2,3,4-tetrahydro-1,5-dihydroxynaphthalene-5-H-phosphonate (4.7 g) as a colorless foam having the following structure:

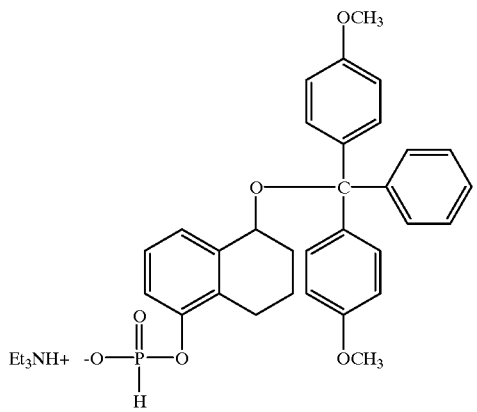

$^{31}$P NMR (202 MHz) DMSO d (ppm) −2.39 (doublet, JP—H=597 Hz). TLC Rf=0.19 (99:1 dichloromethane/methanol/0.1% triethylamine).

EXAMPLE 49

$^{32}$P Labeling of a Library of Non-Nucleotide Phosphorus Ester Oligomers

This label was introduced onto the terminal thymidine residue of a compound library using γ-$^{32}$P labeled adenosine-5'-triphosphate as the donor source and bacteriophage $T_4$ polynucleotide kinase as the enzyme. Conditions for labeling approximated those for labeling of an oligonucleotide (Sambrook et al). Purification was achieved by preparative polyacrylamide gel electrophoresis.

EXAMPLE 50

Preparation of 3-Acetylphenyl 2-Cyanoethyl N,N-diisopropyl Phosphoramidite (2)

To a stirred solution of 3'-hydroxyacetophenone (1, FIG. 1, 3 g, 22 mmol) in anhydrous $CH_2Cl_2$ (120 mL) and N,N-diisopropylethylamine (11.4 g, 88.1 mmol) was added O-(2-cyanoethyl)-N,N-diisopropylamino-chlorophosphoramidite (7.3 g, 30.9 mmol) dropwise over 8 min. The reaction mixture was stirred for 2 h at room temp and evaporated to dryness. The crude oil was partitioned between ethyl acetate (150 mL) and 5% aqueous sodium bicarbonate (150 mL) and the aqueous layer was extracted twice with ethyl acetate (100 mL). The combined organic layers were washed with saturated aqueous sodium chloride solution, dried over anhydrous sodium sulfate, and the solid removed by filtration. The solvents were removed by rotary evaporation and the crude yellow oil was adsorbed onto silica gel and applied to a silica gel flash column (16×10 cm) which was eluted from the column with hexane/ethyl acetate (5:1). Fractions containing pure material were combined and the solvents evaporated to give 2 as a clear liquid (4.8 g, 64%). $^1$H NMR 7.64 (1H, m), 7.52 (1H, m), 7.45 (1H, m), 7.28 (1H, m), 3.87 (2H, m), 3.71 (2H, m), 2.83 (2H, t,J=5.7 Hz), 2.55 (3H, s), 1.19 (6H, d, J=6.7 Hz), 1.11 (6H, d, J=6.7 Hz). Rf=0.19 (Hexane/Ethyl Acetate 5:1).

EXAMPLE 51

Tritium Labeling of a Model Compound

In this example the labeling group is attached to a thymidine residue attached to a solid support. Thymidine-5'-(m-acetylphenyl)phosphate (3a) was prepared on a DNA synthesizer using four 10 $\mu$mol cartridges with a modified 10 $\mu$mol phosphoramidite coupling cycle and 2×15 minute coupling times. A solution of 2 (0.2 M) in anhydrous acetonitrile was used as the coupling reagent. A portion of the solid support (25 $\mu$mol) was cleaved with 29% NH$_4$OH to give crude 3a (559 OD$_{260}$). This material was purified in 4 portions using a C4 reversed-phase HPLC column with a gradient of 5–35% acetonitrile in 0.1M TEAA pH 7 over 6 min and then to 45% acetonitrile over 20 min. Pure fractions were combined and evaporated to give pure 3a (424 OD$_{260}$) as white powder. 1H NMR 7.72 (1H, m), 7.64 (1H, m), 7.44 (1H, m), 7.40 (1H, m), 7.38 (1H, m, H-4), 6.33 (1H, m), 4.57 (1H, m), 4.32 (1H, m), 4.16 (2H, m), 3.18 (6H, q), 2.56 (3H, s), 2.33 (2H, m), 1.47 (3H, s), 1.26 (9H, t).

Electrospray MS: M− 439 (theory 439).

Sodium Borotritiide Reduction of 3a: To 0.5 $\mu$mol of 3a as a lyophilized foam in a screw-cap glass test tube was added sodium borotritiide (20 mCi, 0.31 $\mu$mol, American Radiolabeled Chemicals, Inc., St. Louis, Mo., specific activity 65 Ci/mmol) in 0.01 N aqueous sodium hydroxide solution (200 4 L) and the mixture was allowed to react for 2 h. Unlabeled sodium borohydride (0.024 mg, 0.63 $\mu$mol) in 0.01 N aqueous sodium hydroxide solution (200 $\mu$L of stock solution 2.4 mg/20 mL) was added and the mixture was allowed to 2.5 react an additional 2 h. The reaction mixture was loaded onto a Sep-Pak® C18 plus cartridge previously primed with acetonitrile (10 mL) and water (10 mL). The cartridge was washed with water (5×10 mL), then eluted with 6:4 methanol/water (v:v) (4×1 mL) followed by methanol (1 mL) and the methanolic fractions were evaporated to give the tritium labeled compound 4 (20 OD$_{260}$, 73 nmol, 86 $\mu$Ci, 4% radiochemical yield). Specific activity: 1.18 mCi/$\mu$mol.

EXAMPLE 52

Tritium Labeling of a Library of Non-Nucleotide Phosphorus Ester Oligomers

A library of non-nucleotide phosphorus ester oligomers was prepared and coupled to 3-acetylphenyl 2-cyanoethyl N,N-diisopropyl phosphoramidite (2) to produce a library 3b, possessing 3-acetylphenyl moiety at its terminus. To 0.5 $\mu$mol of this library of non-nucleotide phosphorus ester oligomers in a screw-cap glass test tube was added sodium borotritiide (20 mCi, 0.29 $\mu$mol, American Radiolabeled Chemicals, Inc., St. Louis, specific activity 70 Ci/mmol) in 0.01 N aqueous sodium hydroxide solution (200 $\mu$L) and the mixture was allowed to react for 2 hours. Sodium borohydride (0.024 mg, 0.63 $\mu$mol) in 0.01 N aqueous sodium hydroxide solution (200 gL of stock solution 2.4 mg/20 mL) was added and the mixture was allowed to react an additional 2 hours. The reaction mixture was loaded onto a Sep-Pak® C18 plus cartridge previously primed with acetonitrile (10 mL) and water (10 mL). The cartridge was washed with water (5×10 mL), then eluted with 6:4 methanol/water (v:v) (4×1 mL), methanol (1 mL) and the methanolic fractions were evaporated to give tritium labeled library 4b, 0.82 mCi, 5.7% radiochemical yield, specific activity 1.65 mCi/$\mu$mol.

EXAMPLE 53

Synthesis of a Library of Non-Nucleotide Phosphorus Ester Oligomers with Glycolic Amide Protecting Groups A. Synthesis of Dimethoxytrityl-glycolic acid (5)

Glycolic acid (1.27 g, 16.57 mmol) was treated with pyridine (50 mL) and dimethoxytrityl chloride (6.20 g, 18.22 mmol) and the resulting mixture was stirred at room temperature for 4 hours. The reaction mixture was concentrated, treated with 200 mL ethyl acetate and then extracted with water (3×150 mL). The organic layer was concentrated, redissolved in methanol/water and passed through a column of Dowex-AG5OX8 resin, pyridinium form (60 mL). The filtrate was collected and concentrated to yield 6.0 g of dimethoxytrityl-glycolic acid (5) as the pyridinium salt. This material was used for the next reaction without any further purification.

B. Synthesis of the solid support 7

Long chain alkylamine controlled pore glass (1.0 g, 200–400 mesh, 88.6 umol/g) was treated with 10% triethylamine in 80% aqueous ethanol (100 mL) and then washed extensively with acetonitrile and dried under high vaccum. The solid was suspended in anhydrous pyridine (5 mL) containing diisopropylcarbodiimide (150 ul, 1.0 mmol) and N-hydroxysuccinimide (58 mg, 0.5 mmol). The resulting mixture was shaken vigorously overnight at room temperature, and then filtered. The solid was washed with pyridine, dried under high vacuum and treated with acetic anhydride/pyridine/N-methylimidazole (1:5:1,7.0 mL, v/v) for 30 minutes at room temperature to acetylate unreacted amino groups. Loading of the DMT-glycolic acid (5) according to the dimethoxytrityl cation assay was 48 umol/g. The material obtained was washed with 5% dichloroacetic acid in dichloromethane (40 mL) on a glass filter funnel to remove the dimethoxytrityl group and then washed with CH2Cl$_2$ and dried under vacuum. A suspension of the dry solid support (2 g) in pyridine (2.5 mL) was treated with a solution of dimethoxytrityl-glycolic acid, (0.73 g, 1.6 mmol), triisopropyl sulfonyl chloride (0–44 g, 1.44 mmol) and N-methyl imidazole (115 $\mu$l, 1.44 mmol) in 1.3 mL of pyridine (1.3 mL) and the mixture was shaken at room temperature overnight and then filtered through sintered glass funnel. The support was treated with a mixture of acetic anhydride/pyridine/ N-methyl imidazole (1:5:1, 7.0 mL, v/v) for 30 minutes at room temperature. After filtration, the solid support was washed with pyridine, CH$_3$CN, CH$_2$Cl$_2$ and finally with diethyl ether and then dried under high vacuum. Loading of the DMT—glycolic acid according to the DMT-cation assay was 50 $\mu$mol/g.

C. Library Synthesis

The library is synthesized on 10 columns each loaded with 60 mg of modified solid support that had been derivatized with dimethoxytrityl-glycolic acid (50 umol/g). Each of the 10 monomer H-phosphonates is coupled to its specified support, monomer one to column one, monomer 2 to column 2, etc., up to monomer 10 to column 10. The efficiency of each coupling can be checked by monitoring the intensity of the trityl cation released from each coupling step. After addition of the monomers, the supports are removed from the columns and pooled and divided using the isopycnic slurry method, with acetonitrile as the solvent. The synthesis columns are weighed to ensure an even division of the resin among the columns. After addition of all 10 monomers as previously described, followed by a second pool-and-divide procedure, the non-nucleotide H-phosphonate linkages are converted to phosphoramidate linkages using the following oxidation procedure with each column being oxidized with one of the following amines: 2-(2-aminoethyl)pyridine, 1-(2-aminoethyl)piperidine, 2-(3, 4-dimethoxyphenyl)ethylamine, 4-(2-aminoethyl) morpholine, 1-(3-aminopropyl)-2-pyrolidinone, 2-(3-chlorophenyl)ethylamine, N-isopropyl-1-piperazine acetamide, N-(3-trifluoromethyl)phenylpiperazine, 3,3-diphenylpropylamine, thiomorpholine, 1-(2-pyridyl) piperazine, hexamethyleneimine, cis-2,6-dimethylmorpholine, 1-(4-fluorophenyl)piperazine, 4-fluorophenethylamine, 3,5-dimethylpiperidine. A 10% solution of each amine is prepared individually in carbon tetrachloride and the H-phosphonate moieties are oxidized to phosphoramidate on the DNA synthesizer using a fresh solution of the required amine for 14 minutes. The amine solutions are then flushed from the column and the supports are washed extensively with acetonitrile. The supports are removed from the columns and pooled and divided as described above. A second round of monomer addition followed by pooling, dividing and amine addition is carried out, followed by addition of the synthon required for introduction of the label (either fluorescein phosphoramidite, thymidine H-phosphonate or m-hydroxyacetophenone phosphoramidite). The supports are then removed from the columns and treated with concentrated ammonium hydroxide for 5.5 h at 55° C. The resultant suspensions are filtered and the ammonia removed from the filtrates by bubbling nitrogen through the solutions for 20 minutes. The sixteen solutions are then lyophilized, redissolved in water, purified by reversed-phase HPLC using a gradient of 5–100% acetonitrile in TEAA, 0.1 M, pH 7.0 and pooled to give the library.

EXAMPLE 54

Tritium Labeling of a Phosphoramidate Library via Reductive Methylation

A phosphoramidate library is prepared as synthesized above and after the last pool and divide step all 16 columns are opened and the solid supports are transfered to 16 screw capped glass tubes and suspended in ethylenediamine/$CH_3CN$ (500 $\mu$l, 2:1) for 2 hours at 55° C. After two hours the support is filtered and washed with absolute ethanol (2×500 $\mu$l). The filtrates are combined evaporated to dryness and purified by HPLC using a C4 reversed column to yield the desired sub-libraries. Each sub-library is suspended in 0.1 M HEPES, pH 7.5 (1 mL) and treated with tritium labeled $NaCNBH_3$ (3 equiv, 0.57 mg) and formaldehyde (3 equiv, 0.27 mg). After 3 hours at room temperature the reaction mixtures from each sub-library are loaded on Sep-Pak cartridges (C18, Waters). Each cartridge is washed initially with water (15 mL) and then with 50:50 $H_2O$/$CH_3OH$ (5 mL). The $H_2O$/methanol solutions are collected and freeze dried to yield labeled libraries having structure 10 which are further purified by HPLC using a C4 column with 5–80% acetonitrile in TEAA, 0.1 M, pH 7.0 as the eluant. Alternatively the libraries can be reduced using sodium borohydride instead of sodium cyanoborohydride. In this case each sub-library is suspended in 25 mM $Na_2B_4O_7$, pH 9.0 (1 mL) and initially treated with formaldehyde (10 equiv, 0.9 mg) for 30 minutes followed by $NaBH_4$ (3 equiv, 0.34 mg). After 5 hours the reaction mixture is loaded on Sep-Pak cartridge as is described above and the desired material is eluted using 50:50 $H_2O$/$CH_3OH$ (5 mL).

EXAMPLE 55

Synthesis of a Library of Non-Nucleotide Phosphorus Ester Oligomers in which A is an N-Linked Amino Acid Derivative The library is synthesized on 10 columns each loaded with 60 mg of modified solid support that had been derivatized with glycolic acid. Each of the 10 monomers is coupled to its specified column, monomer one to column one, monomer 2 to column 2, etc., up to monomer 10 to column 10. The efficiency of each coupling is checked by monitoring the intensity of the trityl cation released from each coupling step to be in excess of 90% throughout all of the coupling steps. After addition of the monomers, the resins are then removed from the columns and pooled and divided using the isopycnic slurry method, with acetonitrile as the solvent. The synthesis columns are weighed to ensure an even division of the resin among the columns. After addition of all 10 monomers as previously described, followed by a second pool-and-divide procedure, the nonnucleotide H-phosphonate linkages are converted to phosphoramidate linkage using the following oxidation procedure with each column being oxidized with one of the following aminoacid derivatives: L-methionine ethyl ester HCl, L-alanine methyl ester, L-valine ethyl ester HCl, L-phenylalanine methyl ester HCl, L-glutamic acid diethyl ester, L-tyrosine ethyl ester HCl. A 12% solution of each aminoacid derivative is prepared in DMF/$CCl_4$ (1:1, 5 mL) and the solution is treated with 1 equiv of triethylamine, filtered and the solution is used directly for oxidation of the H-phosphonate moieties. Oxidation is carried out on the DNA synthesizer using a 30 minute reaction time. The amino acid solutions are then flushed from the columns and the supports are washed extensively with acetonitrile. The supports are removed from the columns and pooled and divided as described above. A second round of monomer addition followed by pooling, dividing and addition of amino acid derivative is carried out, followed by addition of the synthon required for introduction of the label (either fluorescein phosphoramidite, dimethoxytritylthymidine H-phosphonate or m-hydroxyacetophenone phosphoramidite). The supports are then removed from the columns and treated with ethylenediamine in acetonitrile (1–5 mL, 2:1) for 1 hour at 55° C. The resultant suspensions are filtered and washed with ethanol (2×500 $\mu$l). The filtrates are combined, concentrated and then redissolved in water and purified by reversed-phase HPLC using a gradient of 5–100% acetonitrile in TEAA, 0.1 M, pH 7.0. The purified fractions are combined to give a library with the structure as follows:

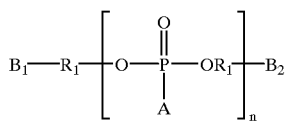

where $B_1$ is a labeling group, $B_2$ is a glycolic ethylenediamine amide, A is an N-linked amino acid ester, and $R_1$ and $R_2$ are derived from diols as previously described.

EXAMPLE 56

Binding of a Library of Phosphorus Ester Oligomers to Thrombin

A library of non-nucleotide phosphorus ester oligomers was screened against the target protein thrombin for high affinity ligands, using the COMPILE method as outlined in copending patent application "Determination and Identification of Active Compounds in a Compound Library," U.S. patent application Ser. No. 08/223,519. Binding reactions consisting of 100 μM oligomeric library and 1 μM target protein as well as a protein-minus control were prepared in a buffer containing 145 mM NaCl, 1.75 mM $MgCl_2$, 4 mM $Na_2HPO_4$, 1.35 mM KCl, 0.45 mM $CaCl_2$, 0.75 mM $KH_2PO_4$ and 12.5 mM Tris-HCl (pH 7.5). The reactions were equilibrated for 15–30 min at room temperature prior to centrifugation through Microcon-10 spin filtration units (M. Wt. cutoff=10,000). The M. Wt. cutoff of the filtration unit was selected to allow free passage of the oligomeric library members but not the target protein or the oligomeric molecules bound to it.

The centrifugation was adjusted to allow approximately 360 μL of the total reaction volume of 400 μL to flow through the membrane, resulting in the loss of approximately 90% of the unbound oligomeric library from the retained sample. The volume of the retained sample was brought up to the original 400 μL with buffer to which was added 20% of the original target concentration to compensate for losses/inactivation of the target during the experiment. After four rounds of selection the library was labeled with $^{32}P$ using T4 kinase followed by purification of the labeled library by forced dialysis. Approximately 38% of the $^{32}P$ counts were incorporated into the library. During subsequent rounds of selection the unincorporated counts flowed freely through the Microcon-10 membrane. To control for unincorporated counts retained, a "no library" sample was carried along with the library sample. The "no library" sample was identical to the library sample with the exception that no library was added to the reaction at the beginning of the selection.

Figure 4:
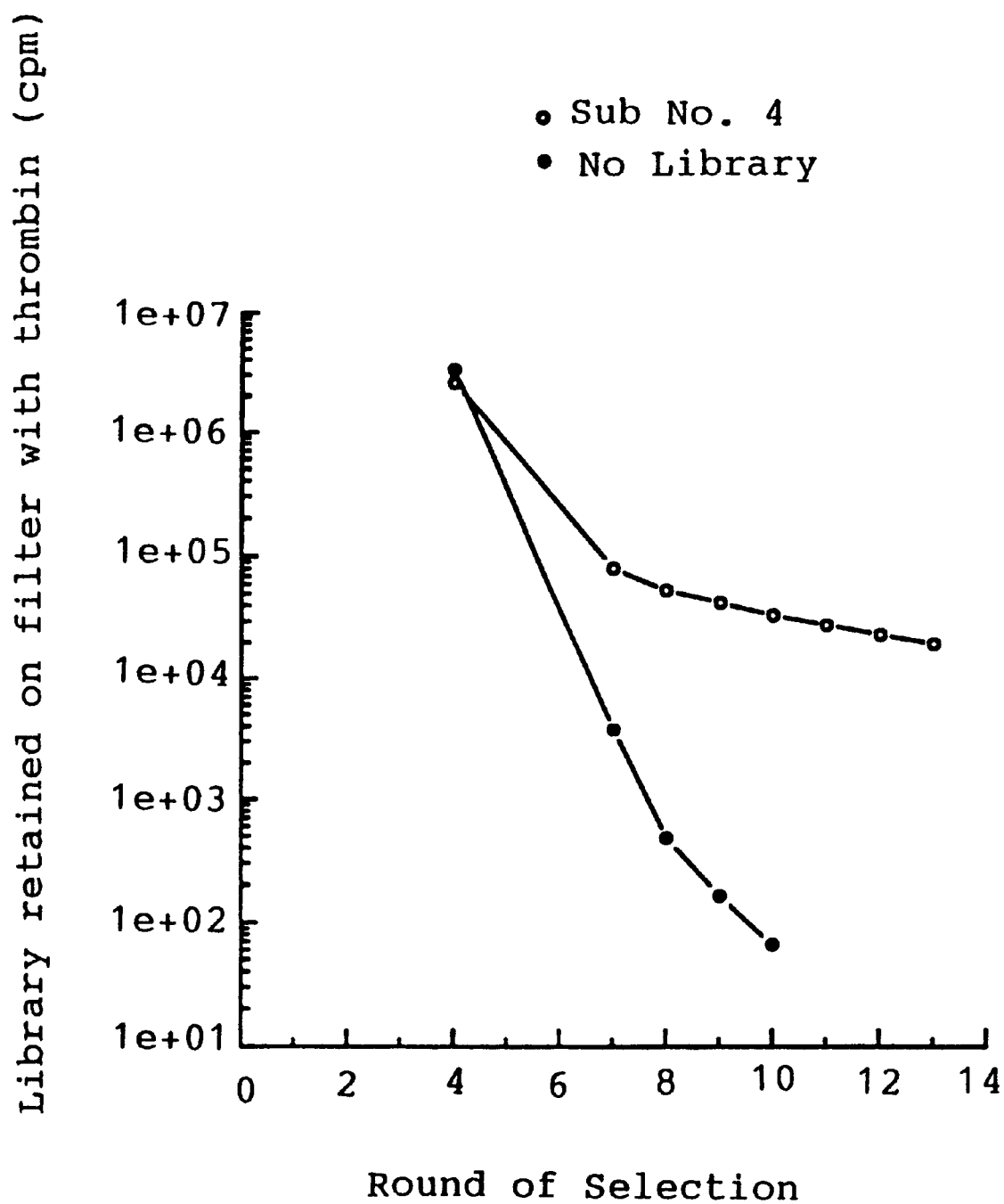
FIG. 4 shows the binding of a library of non-nucleotide phosphorus ester oligomers to thrombin.

The results of this serial selection are presented in FIG. 4. The concentration of the oligomeric library present in the retained fraction (as measured by counts due to the $^{32}P$ tag incorporated into the library members) is plotted as a function of the rounds of selection—i.e. the number of dialysis-based separations. Data are not presented for the first few rounds of selection since the library was labeled after four rounds of selection.

The progressive increase in the fraction of compounds retained at each round is evidence of a subpopulation of the original library that binds to the target. This subpopulation is enriched with each successive round of selection due to selective retention of compounds in the library that bind to the target protein. From the target protein concentration and the curve shown in FIG. 3, it is possible to estimate that this subpopulation of thrombin-binding oligomeric species is between 0.001 and 0.01% of the original mixture, and that it binds an apparent Kd below 100–500 nM.

EXAMPLE 57

Figure 5:
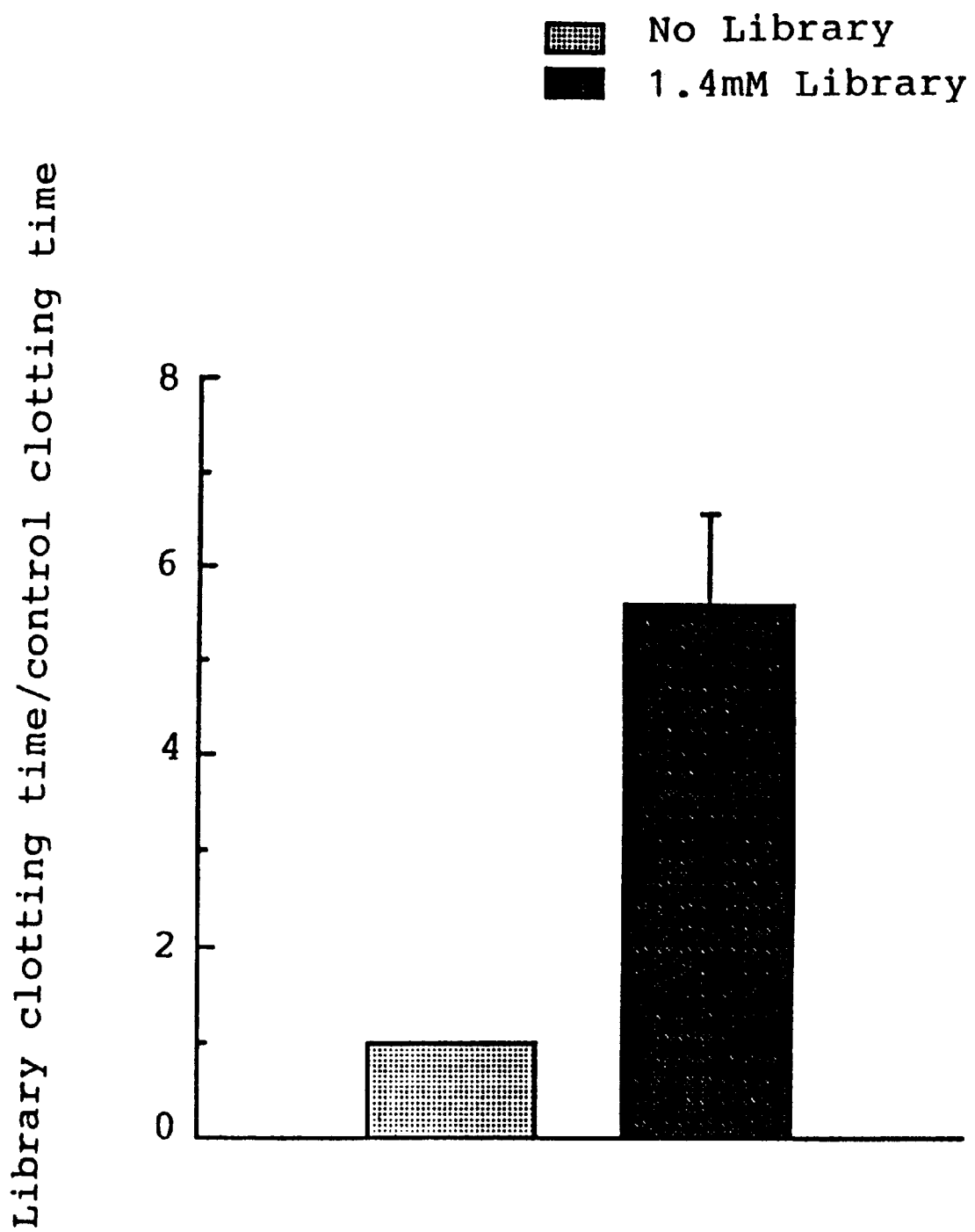
FIG. 5 shows the prolongation of clotting time for a library of non-nucleotide phosphorus ester oligomers as compared with a control in the absence of library.

Prolongation of the Thrombin Induced Clotting Time by a Library of Non-Nucleotide Phosphorus Ester Oligomers Libraries of non-nucleotide phosphorus ester oligomers were prepared as previously described and tested for their ability to inhibit thrombin activity as measured by an extension of the time for thrombin-catalyzed fibrin clot formation. The assay was performed as previously described by Bock et al. Human fibrinogen in 140 mM NaCl, 5 mM KCl, 1 mM $MgCl_2$, 1 mM $CaCl_2$, 20 mM Tris acetate, pH 7.4 (100 uL) was equilibrated at 37° C. for 1 min in the presence of the library of non-nucleotide phosphorus ester oligomers. Clotting reactions were initiated by the addition of human thrombin (100 uL in the same buffer preequilibrated to 37° C. for 1 min) to final concentrations of 2 mg/mL fibrinogen and 3 nM thrombin. The first indication of the clot was taken as the clotting time. Clot formation was usually complete within 5 sec of the first appearance of the clot. As shown in FIG. 5, the library substantially prolonged the thrombin induced clotting time as compared with control reactions without addition of library.

Figure 6:
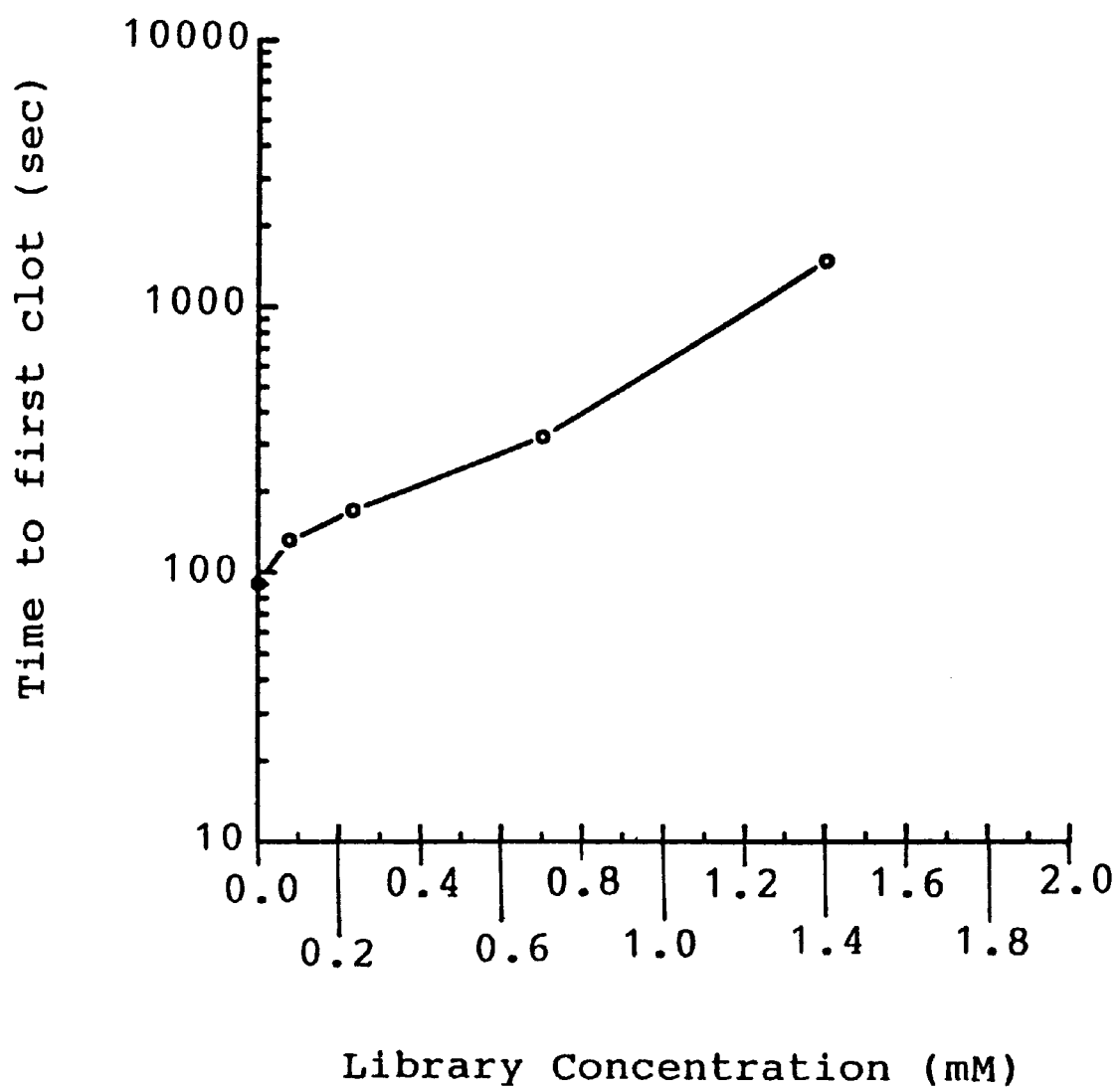
FIG. 6 shows the clotting time as a function of concentration of library of non-nucleotide phosphorus ester oligomers.

The inhibition of clotting was further investigated by carrying out the same clotting reaction using various concentrations of the library of non-nucleotide phosphorus ester oligomers. As shown in FIG. 6, clotting was strongly dose dependent.

LITERATURE CITED

Andrus et al., Tetrahedron Lett., 29: 861 (1988).
Beaucage et al., *Tetrahedron Letts.*, 22:1859–1862, (1981).
Bock et al., *Nature,* 355:564–566, (1992).
Bohacek et al., *JACS,* 116:5560–5571 (1994).
Cload and Schepartz, *JACS,* 113:6324–6326 (1991).
Durand et al., *Nucl. Acids Res.,* 18:6353–6359 (1990).
Ecker, Meeting, "Exploiting Molecular Diversity." San Diego, Calif., Jan 12–14 (1994).
Ecker et al., WO 93/04204 (1993).
Fontanel et al., *Nucleic. Acids Res.,* 22:2022–2027, 1994.
Furdon et al., Nuc. Ac. Res., 17:9193–9204 (1989).
Furka et al., *Int. J. Protein Res.,* 3 7:487–493 (1991).
Gallop et al., *Proc. Natl. Acad. Sci. USA,* 90:10700–10704 (1994).
Gallop et al *J. Med. Chem.,* 37:1233–1251 (1994).
Gordon et al., *J. Med. Chem.,* 37:1385–1401 (1994).
Grollman et al., *J. Biol. Chem.* 262:10171 (1987).
Hardy and Jaffe, *Chemical Abstracts,* 92:42894 (1980).
Hata et al., *Tetrahedron Lett.,* 26:935 (1986).
Hovinen et al., *Tetrahedron,* 50:7203–7218, 1994.
Lander, *Chem. & Biol.,* 1:73–78 (1994).
Leumann et al., *Helvetica Chemica Acta,* 79:481–510 (1993).
Matteucci et al., *JACS,* 115:9816–9817 (1993).
Ogilvie et al., *Tetrahedron Lett.,* 21:4149 (1980).
Richardson and Schepartz, *JACS,* 113:5109–5111 (1991).
Salunkhe et al., *JACS,* 114:8768–8772 (1992).
Sambrook et al., *Molecular Cloning, a Laboratory Manual 2nd edition;* p. 5.68, Cold Spring Harbor Laboratory Press: Cold Spring Harbor, N.Y., 1989.
Sase et al., *Chemical Abstracts,* 108:6181 (1988).
Seela and Kaiser, *Nucleic Acids Res.,* 15:3113 (1987).

Zuckerman et al., *J. Med. Chem.*, 37:2678–2685 (1994).

What is claimed is:

1. A phosphorus ester oligomer of monomeric units, which oligomer has the structure:

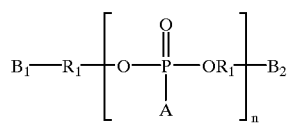

wherein

A is the same or different in each monomeric unit and each is independently selected from the group consisting of oxygen, sulfur, lower alkyl, substituted or unsubstituted alkylamino, substituted or unsubstituted arylamino and aminoalkyl;

$B_1$ and $B_2$ are the same or different and each is independently selected from hydrogen, lower alkyl, a labeling group, a protecting group, a phosphoramidyl or a phosphomonoesteryl;

$R_1$ is the same or different in each monomeric unit, and in at least one of the monomeric units, $R_1$ is independently selected from the group consisting of (i) a non-vicinal diol attached to a hydrogen bond donor functionality; (ii) a hydrogen bond acceptor selected from an ether; (iii) a non-vicinal diol attached to a hydrophobic functionality or a vicinal diol attached to an aliphatic or alicyclic hydrophobic functionality; (iv) a diol attached to a ring substituted anionic functionality; and (v) a cationic moiety attached to a non-vicinal or alicyclic diol, and $R_1$ is optionally substituted with a detectable label; and n is at least two.

2. The oligomer of claim 1 wherein the hydrogen bond donor is a hydroxyl, amide, imide or thiol group.

3. The oligomer of claim 1 wherein the hydrogen bond donor is a basic compound.

4. The oligomer of claim 3 wherein the basic compound is an amine moiety.

5. The oligomer of claim 1 wherein $R_1$ is a hydrogen bond acceptor which is an amine or ether moiety.

6. The oligomer of claim 1 wherein $R_1$ is a hydrophobic functionality selected from the group consisting of aromatic rings, alkanes, cycloalkanes and aromatic rings fused to cycloalkanes.

7. The oligomer of claim 6 wherein $R_1$ is a hydrophobic functionality selected from a substituted alkane, a 3,3-disubstituted 3-amino-1,2-propanediol, a substituted or unsubstituted alicyclic ring wherein the ring size is from 4–12, a substituted or unsubstituted hydroxyalkyl phenol and an alicyclic dicarboxylic acid.

8. The oligomer of claim 1 wherein the anionic functionality is an alicyclic dicarboxylic acid moiety.

9. The oligomer of claim 8 wherein the anionic functionality is a tricyclononene dicarboxylic acid moiety.

10. The oligomer of claim 1 wherein the anionic functionality is a cyclopentane acetic acid moiety.

11. The oligomer of claim 1 wherein the cationic functionality is selected from a substituted alkane and a 3,3-disubstituted 3-amino-1,2-propanediol.

12. The oligomer of claim 1 wherein in at least one of the monomeric units $R_1$ is an alicyclic or a polycyclic ring system.

13. The oligomer of claim 12 wherein the alicyclic ring system is a cyclopentane or cyclooctane ring.

14. The oligomer of claim 13 wherein the cyclopentane or cyclooctane ring system is substituted with at least one carboxylic acid moiety.

15. The oligomer of claim 12 wherein the polycyclic ring system is a bicyclic or tricyclic ring or is a polycyclic arene.

16. The oligomer of claim 15 wherein the bicyclic ring is a bicyclic alkane.

17. The oligomer of claim 16 wherein the bicyclic ring is bicycloheptane.

18. The oligomer of claim 15 wherein the tricyclic ring is an alkene.

19. The oligomer of claim 18 wherein the alkene is tricyclononene.

20. The oligomer of claim 15 wherein the polycyclic arene is diphenyl bicyclooctane.

21. The oligomer of claim 1 wherein A is selected from the group consisting of 2-(3,4-dimethyloxyphenyl) ethylamine, 3-aminopropionitrile, 4-fluorophenethylamine, 4-bromophenethylamine, aminomethylcyclopropane, 3,3-diphenylpropylamine, hexamethyleneimine, 2-(4-chlorophenyl)ethylamine, 2-thiophenemethylamine, and heptamethyleneimine.

22. The oligomer of claim 1 wherein A is an N-linked amino acid.

23. A phosphorus ester oligomer of monomeric units, which oligomer has the structure:

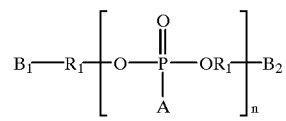

wherein

A is the same or different in each monomeric unit and each is independently selected from the group consisting of oxygen, sulfur, lower alkyl, substituted or unsubstituted alkylamino, substituted or unsubstituted arylamino and aminoalkyl;

$B_1$ and $B_2$ are the same or different and each is independently selected from hydrogen, lower alkyl, a labeling group, a protecting group, a phosphoramidyl or a phosphomonoesteryl;

$R_1$ is the same or different in each monomeric unit, and in at least one of the monomeric units is independently selected from:
   (i) an aliphatic alicyclic diol wherein the diol hydroxyl groups are non-vicinal or are substituted;
   (ii) an acyclic aliphatic diol having an amino group with at least one hydrogen substitution moiety;
   (iii) an alicyclic or polycyclic diol, optionally substituted with a carboxy or carboxyalkyl substituent;
   (iv) an aromatic ring or ring system having two substitutions independently selected from the group consisting of hydroxy or hydroxyalkyl;
   (v) $R_1$ is optionally substituted with a detectable label; and n is at least two.

24. The oligomer of claim 23 wherein n is 2–20.

25. The oligomer of claim 23 wherein A is selected from the group consisting of 2-(3,4-dimethyloxyphenyl) ethylamine, 3-aminopropionitrile, 4-fluorophenethylamine, 4-bromophenethylamine, aminomethylcyclopropane, 3,3-diphenylpropylamine, hexamethyleneimine, 2-(4-chlorophenyl)ethylamine, 2-thiophenemethylamine, and heptamethyleneimine.

26. The oligomer of claim 23 wherein A is an N-linked amino acid.

27. A non-nucleotide monomeric unit, having the structure:

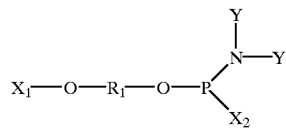

wherein
- $X_1$ is a protecting group;
- $X_2$ is a branched or unbranched lower alkyl group or a substituted or unsubstituted alkoxy group;
- Y is a branched or unbranched lower alkyl group; and
- $R_1$ is selected from the group consisting of (i) a non-vicinal diol attached to a hydrogen bond donor functionality; (ii) a hydrogen bond acceptor selected from an ether; (iii) a non-vicinal diol attached to a hydrophobic functionality or a vicinal diol attached to an aliphatic or alicyclic hydrophobic functionality; (iv) a diol attached to a ring substituted anionic functionality; and (v) a cationic moiety attached to a non-vicinal or alicyclic diol, and $R_1$ is optionally substituted with a detectable label.

28. The non-nucleotide monomeric unit of claim 27 wherein the anionic functionality is a cyclopentane acetic acid moiety.

29. The non-nucleotide monomeric unit of claim 27 wherein the cationic functionality is a 3,3-disubstituted 3-amino-1,2-propanediol.

30. The non-nucleotide monomeric unit of claim 27 wherein $R_1$ is:
   (i) an aliphatic acyclic diol wherein the diol hydroxyl groups are non-vicinal or are substituted;
   (ii) an acyclic aliphatic diol having an amino group with at least one hydrogen substitution moiety;
   (iii) an alicyclic or polycyclic diol, optionally substituted with a carboxy or carboxyalkyl substituent; or
   (iv) an aromatic ring or ring system having two substitutions independently selected from the group consisting of hydroxy or hydroxyalkyl;
   and in which $R_1$ is optionally substituted with a detectable label.

31. A non-nucleotide monomeric unit, having the structure:

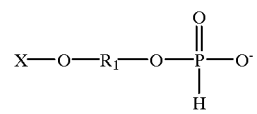

wherein
- X is a protecting group; and
- $R_1$ is selected from the group consisting of (i) a non-vicinal diol attached to a hydrogen bond donor functionality; (ii) a hydrogen bond acceptor selected from an ether; (iii) a non-vicinal diol attached to a hydrophobic functionality or a vicinal diol attached to an aliphatic or alicyclic hydrophobic functionality; (iv) a diol attached to a ring substituted anionic functionality; and (v) a cationic moiety attached to a non-vicinal or alicyclic diol, and $R_1$ is optionally substituted with a detectable label.

32. The non-nucleotide monomeric unit of claim 31 wherein the anionic functionality is a cyclopentane acetic acid moiety.

33. The non-nucleotide monomeric unit of claim 31 wherein the cationic functionality is a 3,3-disubstituted 3-amino-1,2-propanediol.

34. The non-nucleotide monomeric unit of claim 31 wherein $R_1$ is:
   (i) an aliphatic acyclic hydrocarbon diol wherein the diol hydroxyl groups are non-vicinal or are substituted;
   (ii) an acyclic aliphatic diol having an amino group with at least one hydrogen substitution moiety;
   (iii) an alicyclic or polycyclic diol, optionally substituted with a carboxy or carboxyalkyl substituent; or
   (iv) an aromatic ring or ring system having two substitutions independently selected from the group consisting of hydroxy or hydroxyalkyl;
   and $R_1$ is optionally substituted with a detectable label.

* * * * *